US012655111B2

(12) United States Patent
Geigle et al.

(10) Patent No.: US 12,655,111 B2
(45) Date of Patent: Jun. 16, 2026

(54) PHENAZINE-BASED COMPOUNDS

(71) Applicant: CMBLU Energy AG, Alzenau (DE)

(72) Inventors: Peter Geigle, Alzenau (DE); Jan Hartwig, Alzenau (DE); Eduard Baal, Offenbach (DE); Isabel Scheibel, Alzenau (DE); Evgeny Larionov, Hanau (DE); Olga Ekkert, Hanau (DE); Doris Neumann, Offenbach (DE); Christian Schneider, Aschaffenburg (DE)

(73) Assignee: CMBlu Energy AG, Alzenau (DE)

( * ) Notice: Subject to any disclaimer, the term of this patent is extended or adjusted under 35 U.S.C. 154(b) by 643 days.

(21) Appl. No.: 17/799,879

(22) PCT Filed: Feb. 22, 2021

(86) PCT No.: PCT/EP2021/054344

§ 371 (c)(1),
(2) Date: Aug. 15, 2022

(87) PCT Pub. No.: WO2021/165542

PCT Pub. Date: Aug. 26, 2021

(65) Prior Publication Data

US 2023/0095542 A1 Mar. 30, 2023

(30) Foreign Application Priority Data

Feb. 20, 2020 (WO) ................. PCT/EP2020/054568

(51) Int. Cl.
*C07D 241/16* (2006.01)
*H01M 8/18* (2006.01)

(52) U.S. Cl.
CPC ............ *C07D 241/16* (2013.01); *H01M 8/18* (2013.01); *H01M 2300/0025* (2013.01)

(58) Field of Classification Search
None
See application file for complete search history.

(56) References Cited

U.S. PATENT DOCUMENTS

| | | | | |
|---|---|---|---|---|
| 1,916,627 | A | 7/1933 | Mersch | |
| 1,963,383 | A | 6/1934 | Rogers | |
| 3,389,124 | A * | 6/1968 | Sparks | C09K 15/30 524/925 |
| 3,646,071 | A | 2/1972 | Frey et al. | |
| 4,124,606 | A | 11/1978 | Anello et al. | |
| 4,420,644 | A | 12/1983 | Huibers et al. | |
| 4,579,943 | A | 4/1986 | Kamide et al. | |
| 4,956,244 | A | 9/1990 | Shimizu et al. | |
| 5,002,634 | A | 3/1991 | Dimmel et al. | |
| 5,049,477 | A | 9/1991 | Nakamura et al. | |
| 5,723,675 | A | 3/1998 | Joo et al. | |
| 5,932,752 | A | 8/1999 | Keshavaraja et al. | |
| 5,944,953 | A | 8/1999 | Lavoie et al. | |
| 9,548,509 | B2 | 1/2017 | Anderson et al. | |
| 10,777,836 | B1 | 9/2020 | Wei et al. | |
| 11,008,284 | B2 | 5/2021 | Krawczyk et al. | |
| 11,225,756 | B2 | 1/2022 | Krawczyk et al. | |
| 11,450,854 | B2 | 9/2022 | Hartwig et al. | |
| 11,731,945 | B2 | 8/2023 | Geigle et al. | |
| 2004/0244925 | A1 | 12/2004 | Tarasenko | |
| 2007/0073076 | A1 | 3/2007 | Lewis et al. | |
| 2010/0086675 | A1 | 4/2010 | Berta et al. | |
| 2011/0144337 | A1 | 6/2011 | Santhosh et al. | |
| 2011/0268652 | A1 | 11/2011 | Machhammer et al. | |
| 2012/0045680 | A1 | 2/2012 | Dong et al. | |
| 2013/0079566 | A1 | 3/2013 | Lin | |
| 2013/0084482 | A1 | 4/2013 | Chang et al. | |
| 2013/0116424 | A1 | 5/2013 | Peterson et al. | |
| 2013/0232852 | A1 | 9/2013 | Peterson et al. | |
| 2013/0232853 | A1 | 9/2013 | Peterson et al. | |
| 2014/0028261 | A1 | 1/2014 | Esswein et al. | |
| 2014/0370403 | A1 | 12/2014 | Narayan et al. | |
| 2014/0370405 | A1 | 12/2014 | Zhang et al. | |
| 2015/0243991 | A1 | 8/2015 | Huskinson et al. | |
| 2016/0009621 | A1 | 1/2016 | Blair | |
| 2016/0013497 | A1 | 1/2016 | Jones et al. | |
| 2016/0032525 | A1 | 2/2016 | Kurple et al. | |
| 2016/0130752 | A1 | 5/2016 | Stigsson et al. | |
| 2016/0197371 | A1 | 7/2016 | Takechi | |
| 2017/0162916 | A1 | 6/2017 | Guarr et al. | |
| 2018/0079721 | A1 | 3/2018 | Armand et al. | |
| 2018/0097249 | A1 | 4/2018 | Narayan et al. | |
| 2018/0099917 | A1 | 4/2018 | Anthony et al. | |
| 2018/0366757 | A1 * | 12/2018 | Wei | C07D 241/46 |

(Continued)

FOREIGN PATENT DOCUMENTS

| | | |
|---|---|---|
| CN | 101475758 A | 7/2009 |
| CN | 102040483 A | 5/2011 |

(Continued)

OTHER PUBLICATIONS

Lange, A., Tavan, P., Schroder, D., Baumgartel, H.—The Electronic Spectra of Aminophenazines, Ber.Bunsenges.Phys.Chem.85, pp. 78-85, 1981 (Year: 1981).*
Nagai, K., Carter, B.J., Xu, J., Hecht, S.H.—DNA Cleavage by Oxygen Radicals Produced in the Absence of Metal Ions or Light, J. Am. Chem. Soc., 113, pp. 5099-5100, 1991 (Year: 1991).*
Martin, D.A., Tariq, A., Richards, B.D.O., Jose, G., Krasnikov,S.A., Kulak, A., Sergeeva, N.N.—White light induced colvalent modification of graphene using a phenazine dye, Chem. Commun., 2017, 53, pp. 10715-10718 (Year: 2017).*
Zamaratski, E., Chattopadhyaya, J.-Synthesis of Phenazine-tethered Arabino and Zylofuranosyl Oligonucleotide Conjugates: The Thermal Stability and Flourescence Properties of Their Duplexes (DNA-DNA & DNA-RNA) & Triplets, Tetrahedron 54 (1998) pp. 8183-8206 (Year: 1998).*

(Continued)

*Primary Examiner* — Anca Eoff
(74) *Attorney, Agent, or Firm* — Harness Dickey & Pierce P.L.C.

(57) ABSTRACT

The present invention relates to novel phenazine-based compounds and compositions comprising the same and their use as redox flow battery electrolytes.

37 Claims, 3 Drawing Sheets

(56) References Cited

U.S. PATENT DOCUMENTS

Figure 1:
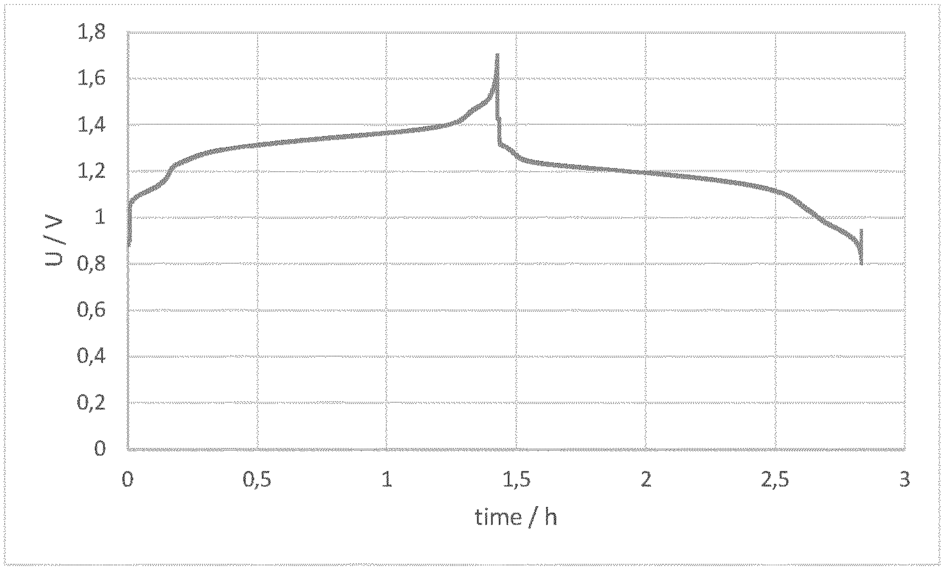

| | | | | |
|---|---|---|---|---|
| 2018/0375142 | A1* | 12/2018 | Zhang | H01M 8/023 |
| 2019/0152902 | A1 | 5/2019 | Krawczyk et al. | |
| 2019/0390405 | A1 | 12/2019 | Geigle et al. | |
| 2019/0393506 | A1 | 12/2019 | Hartwig et al. | |
| 2020/0014040 | A1 | 1/2020 | Kerker et al. | |
| 2020/0283380 | A1 | 9/2020 | Krawczyk et al. | |
| 2020/0373597 | A1 | 11/2020 | Perry et al. | |
| 2021/0020943 | A1 | 1/2021 | Hartwig et al. | |
| 2021/0024453 | A1 | 1/2021 | Hartwig et al. | |
| 2021/0083310 | A1 | 3/2021 | Perry et al. | |
| 2021/0276945 | A1 | 9/2021 | Krawczyk et al. | |
| 2022/0048869 | A1 | 2/2022 | Lee et al. | |
| 2023/0097730 | A1* | 3/2023 | Geigle | H01M 8/188 429/105 |
| 2023/0130406 | A1 | 4/2023 | Hartwig et al. | |
| 2023/0304221 | A1 | 9/2023 | Krawczyk et al. | |
| 2023/0411662 | A1* | 12/2023 | Ekkert | H01M 8/188 |
| 2024/0014409 | A1 | 1/2024 | Geigle et al. | |
| 2024/0014427 | A1 | 1/2024 | Ekkert et al. | |
| 2024/0222674 | A1* | 7/2024 | Geigle | H01M 8/188 |
| 2024/0270672 | A1 | 8/2024 | Geigle et al. | |
| 2024/0318382 | A1 | 9/2024 | Krawczyk et al. | |
| 2024/0356030 | A1 | 10/2024 | Hartwig et al. | |
| 2025/0263384 | A9 | 8/2025 | Geigle et al. | |

FOREIGN PATENT DOCUMENTS

| | | | | |
|---|---|---|---|---|
| CN | 103000924 | A | 3/2013 | |
| CN | 104005046 | A | 8/2014 | |
| CN | 103762377 | B | 3/2016 | |
| CN | 107425212 | A | 12/2017 | |
| EP | 3492628 | A1 | 6/2019 | |
| FR | 3030561 | A1 | 6/2016 | |
| GB | 1086522 | | 10/1967 | |
| GB | 1502275 | A | 3/1978 | |
| JP | S51100064 | A | 9/1976 | |
| JP | S51138666 | A | 11/1976 | |
| JP | S52144662 | A | 12/1977 | |
| JP | H01115068 | A | 5/1989 | |
| JP | H06260204 | A | 9/1994 | |
| JP | H9227499 | A | 9/1997 | |
| JP | 3813864 | B2 | 8/2006 | |
| JP | 2011057636 | A | 3/2011 | |
| JP | 2013254685 | A | 12/2013 | |
| JP | 2019503619 | A | 2/2019 | |
| RO | 76126 | A2 | 5/1981 | |
| SU | 1129204 | A1 | 12/1984 | |
| WO | 1998/013538 | A1 | 4/1998 | |
| WO | 2011111717 | A1 | 9/2011 | |
| WO | 2011131959 | A1 | 10/2011 | |
| WO | WO2011142838 | | 11/2011 | |
| WO | 2013131838 | A1 | 9/2013 | |
| WO | 2014081235 | A1 | 5/2014 | |
| WO | 2014204985 | A1 | 12/2014 | |
| WO | 2015048550 | A1 | 4/2015 | |
| WO | 2015148357 | A1 | 10/2015 | |
| WO | 2016144909 | A1 | 9/2016 | |
| WO | 2017174098 | A1 | 10/2017 | |
| WO | WO-2018152436 | A1 * | 8/2018 | A61P 31/06 |
| WO | WO2018231926 | | 12/2018 | |
| WO | WO2019240933 | | 12/2019 | |
| WO | 2020035549 | A2 | 2/2020 | |
| WO | WO2020035138 | | 2/2020 | |
| WO | 2020201405 | A1 | 10/2020 | |

OTHER PUBLICATIONS

Dilung, I.I., Granchak, V.M., Usacheva, M.N.—Scientific selection of photopolymerization initiators for information recording, Visnik Akademii Nauk Ukrains'koi RSR, (1984) (12), pp. 15-23 (Year: 1984).*

Charalambous, et al., "Deoxygenation of 2-Nitrosophenols and of their Metal Complexes with Triphenyphosphine. Sytnthesis of Phenzaines, Dihydrophenazines, Triphenyl(o-hydroxyphenylimino)phosphoranes and their Metal Complexes", Journal of The Chemical Society, Jan. 1, 1977 (Jan. 1, 1977), pp. 400-401, XP055781425.

Gao Xiaochun et al., AL: "Synthesis and anti cancer activity of some novel 2-phenazinamine derivatives", European Journal of Medicinal Chemistry, vol. 69, Nov. 1, 2013 (Nov. 1, 2013), pp. 1-9, XP5581485.

Laha J.K., et al.,: "Transition-Metal-Free Tandem Oxidative Removal of Benzylic Methylene Group by C—C and C—N Bond Cleavage Follwed by Intramolecular New Aryl C—N Bond Formation under Radical Conditions", Org. Lett. 2014, 16, 17, 4392-4395 Publication Date: Aug. 14, 2014.

Salomi B.S: et al., "Electrochemical studies of horseradish peroxidase covalently coupled with redox dyes", Biosensors and Bioelectronics, vol. 22, No. 8, Mar. 15, 2007 (Mar. 15, 2007), pp. 1825-1829, XP55781463.

Tabor, Daniel P: "Approaching saturation limits", Nature Energy volue 3, pp. 455-456 (2018).

Waters, W.A. et al.: "The reaction of phenazine with free benzyl radicals", J. Chem. Soc., 1959, 2085-2087, https://doi.org/10.1039/JR9590002085.

Yoshioka I., et al: "Studies on Phenazines. XXV. On the Bromination of 1-and 2-Methylphenazine by N-Bromosuccinimide.(1)", Chem Pharm Bull (Tokyo) 1964.

Intemational Search Report and Written Opinion received for International Application No. PCT/EP2021/054296 mailed on Mar. 16, 2021.

Non-Final Office Action from U.S. Appl. No. 17/799,877 dated Jul. 16, 2025.

International Search Report from corresponding PCT Application No. PCT/EP2021/087647 dated Apr. 11, 2022.

Written Opinion from corresponding PCT Application No. PCT/EP2021/087647 dated Apr. 11, 2022.

Sanchez-Diez, E., et al., "Redox flow batteries: Status and perspective towards sustainable stationary energy storage," Journal of Power Sources, 481: 1-23 (2020).

Zhou, M., et al., "Single-Molecule Redox-Targeting Reactions for a pH-Neutral Aqueous Organic Redox Flow Battery," Angew. Chem. Int. Ed., 59: 14286-14291 (2020).

Arai, G., and Onozuka, M., "The Reaction of 1, 4-Naphthoquinone-2-sulfonate with Sodium Sulfite," The Chemical Society of Japan, 12: 1899-1903, (1981).

Azarov, V.I., "Khimiya drevesiny i sinteticheskikh polimerov," Sankt-Petersburg, pp. 366-373 (1999).

Brauns, F.E., "Khimiya lignina," Moscow, pp. 558-570 (1964).

Denisov, E.T., and Metelitsa, D.I., "Oxidation of Benzene," Russ. Chem. Rev., 37 (656), 1968.

Dominguez-Ramos, A., et al., "Electrochemical Oxidation of Lignosulfonate: Total Organic Carbon Oxidation Kinetics," Ind. Eng. Chem. Res., 47(24): 9848-9853 (2008).

Dorn, Bv H. W., et al., "Certain Derivatives of the Ethers of Hydroxyhydroquinone," Journal of the American Chemical Society, 61: 144-147 (1939).

Duval, A., et al., "Fractionation of lignosulfonates: comparison of ultrafiltration and ethanol solubility to obtain a set of fractions with distinct properties," Holzforschung, 69(2): 127-134 (2015).

Fitzky, H.G., et al., "Paramagnetic electron resonance measurements fo short-lived, substituted p-benzosemiquinones," Photographische Korrespondenz, 103(4): 60-64 (1967).

Gierer, J., "Chemistry of delignification, Part 1: General concept and reactions during pulping," Wood Science and Technology, 19: 289-312 (1985).

Gierer, J., "Chemistry of delignification: Part 2: Reactions of lignins during bleaching," Wood Science and Technology, 20: 1-33 (1986).

Hu L., et al., "Methods to Improve Lignin's Reactivity as A Phenol Substitute and as Replacement for Other Phenolic Compounds: A Brief Review," Bio Resources, 6(3): 3515-3525 (2011).

Huber, G. W., et al., "Synthesis of Transportation Fuels from Biomass: Chemistry, Catalysts, and Engineering," Chemical Reviews, American Chemical Society, 106: 4044-4098 (2006).

International Search Report from PCT Application No. PCT/EP2018/053595 dated Jun. 12, 2018.

(56) References Cited

OTHER PUBLICATIONS

International Search Report from PCT Application No. PCT/EP2018/053596 dated May 3, 2018.
International Search Report from PCT Application No. PCT/EP2018/053597 dated May 8, 2018.
International Search Report from PCT Application No. PCT/EP2019/053602 dated Apr. 3, 2019.
International Search Report issued in PCT/EP2017/000461 dated Dec. 6, 2017.
International Search Report issued in PCT/EP2017/000462 issued Sep. 6, 2017.
Mark, H. B., and Atkin, C. L., "Electrode Reactions of Aromatica Compounds in Strong Acid Solutions," Analytical Chemistry, 36(3): 514-520 (1964).
Miyazawa, T., et al., "Highly regioselective propanoylation of dihydroxybenzenes mediated by Candida antarctica lipase B in organic solvents," Tetrahedron Letters, 49: 175-178 (2008).
Moodley, B. et al., "The electro-oxidation of lignin in Sappi Saiccor dissolving pulp mill effluent," 37(1): 33-40 (2011).
Office Action dated Mar. 20, 2020 issued in U.S. Appl. No. 16/091,436.
Office Action from corresponding Eurasian Patent Application No. 201892234 dated Sep. 10, 2019.
Office Action from corresponding Japanese Application No. 2019-503619 dated Feb. 8, 2022.
Office Action from corresponding U.S. Appl. No. 16/480,956 dated Aug. 17, 2021.
Office Action from corresponding U.S. Appl. No. 16/480,958 dated Aug. 23, 2021.
Restriction Requirement from U.S. Appl. No. 16/091,437 dated Jun. 15, 2020.
Smook, Gary A., "Handbook for Pulp and Paper Technologists," Angus Wilde Publications, 2nd edition, chapters 7 and 8 (1992).
Vandenberghe A., and Willems J.F., "Sulphonation of Alkylhydroquinones," Bull. Soc. Chim. Belges, 74(9-10): 397-406 (1965).
Weatherbee, C., et al., "A New Approach to Tertiary b-Chloroalkylamines. Synthesis of b-Chloroalkylaminomethylhydroquinones1", Journal of Organic Chemistry, 21(10): 1138-1141 (1956).
Wedege, K., et al., "Organic Redox Species in Aqueous Flow Batteries: Redox Potentials, Chemical Stabilitiy and Solubility," Scientific Reports, 6(1): 1-13 (2016).
Weetall, H. H., et al., "Biotechnology and Bioengineering—A Direct Fuel Cell for the Production of Electricity from Lignin," vol. 27, No. 7, p. 1-11 (1985).
Written Opinion from PCT Application No. PCT/EP2018/053595 dated Jun. 12, 2018.
Written Opinion from PCT Application No. PCT/EP2018/053596 dated May 3, 2018.
Written Opinion from PCT Application No. PCT/EP2018/053597 dated May 8, 2018.
Written Opinion from PCT Application No. PCT/EP2019/053602 dated Apr. 3, 2019.
Written Opinion issued in PCT/EP2017/000461 issued Dec. 6, 2017.
Written Opinion issued in PCT/EP2017/00462 issued on Sep. 6, 2017.
www.chem.uiuc.edu, "Oxidation of Phenols," (1999).
Xu, Ch. et al., "Lignin depolymerisation strategies: towards valuable chemicals and fuels," Chem Soc Rev. 43: 7485-7500 (2014).
Yang, B., et al., "An Inexpensive Aqueous Flow Battery for Large-Scale Electrical Energy Storage Based on Water-Soluble Organci Redox Couples," Journal of the Electrochemical Society, 161(9): A1371-A1380 (2014).
Zakzeski, J. et al., "The Catalytic Valorization of Lignin for the Production of Renewable Chemicals," Chem. Rev., 110: 3552-3599 (2010).
Zhang, S., et al., "An Organic Electroactive Material for Flow Batteries," Electrochimica Acta, 190: 737-743 (2016).
Zhou, Y. et al., "Methods To Improve Lignin's Reactivity as a Phenol Substitute and as Replacement for Other Phenolic Compounds: A Brief Review," BioResources, 6(3): 1-11 (2011).
Office Action from corresponding U.S. Appl. No. 16/480,958 dated Apr. 26, 2022.
Office Action from corresponding U.S. Appl. No. 16/484,301 dated Apr. 22, 2022.
Kaiho, A. et al., "Construction of the di(trimethylolpropane) cross linkage and the phenylnaphthalene structure coupled with selective ?-O-4 bond cleavage for synthesizing lignin-based epoxy resins with a controlled glass transition temperature," Green Chem., 18: 6526-6535 (2016).
Klein, I. et al., "Lignin depolymerization over Ni/C catalyst in methanol, a continuation: effect of substrate and catalyst loading," Catal. Sci. Technol., 5: 3242-3245 (2015).
Office Action issued in corresponding U.S. Appl. No. 16/480,958 dated Feb. 4, 2022.
Office Action issued in corresponding U.S. Appl. No. 16/480,958 dated Sep. 14, 2022.
Restriction Requirement issued in corresponding U.S. Appl. No. 16/484,301 dated Sep. 29, 2021.
Office Action issued in corresponding U.S. Appl. No. 16/484,301 dated Oct. 27, 2022.
Restriction Requirement issued in U.S. Appl. No. 16/968,732 dated Mar. 17, 2022.
Office Action issued in U.S. Appl. No. 16/968,732 dated Jun. 24, 2022.
Office Action issued in U.S. Appl. No. 16/968,732 dated Nov. 30, 2022.
Restriction Requirement issued in corresponding U.S. Appl. No. 16/480,956 dated Apr. 28, 2021.
Restriction Requirement issued in corresponding U.S. Appl. No. 16/091,436 dated Aug. 1, 2019.
Interview Summary issued in corresponding U.S. Appl. No. 16/091,436 dated Jun. 4, 2020.
Office Action issued in corresponding U.S. Appl. No. 16/091,437 dated Nov. 25, 2020.
Office Action issued in corresponding U.S. Appl. No. 16/091,437 dated May 4, 2021.
Yang et al., "High-Performance Aqueous Organic Flow Battery with Quinone-Based Redox Couples at Both Electrodes", Journal of The Electrochemical Society 163(7):A1442-A1449 (2016).
Search Report issued in corresponding EP Appln. No. EP22173705.9 dated Oct. 28, 2022.
Office Action issued in corresponding U.S. Appl. No. 16/967,898 dated Dec. 6, 2022.
Office Action issued in corresponding JP Appln. No. 2021-142062 dated Mar. 16, 2023.
Search Report issued in corresponding EP Appln. No. 22203539.6 dated Mar. 15, 2023.
Search Report issued in corresponding EP Appln. No. 22203648.5 dated Mar. 17, 2023.
Chowdhury Pankaj et al., "Aqueous Photoelectrochemical Reduction of Anthraquinone Disulfonate at Organic Polymer Films", Macromolecular Chemistry and Physics, 217(10):1119-1127 (2016).
Corby B. W. et al., "Clean-chemistry sulfonation of aromatics", J. Chem. Research (S), 26-327 (2002).
Abraham, Ignatious et al. "Recent Advances in 1,4-Benzoquinone Chemistry", Journal of the Brazilian Chemical Society, 22(3):385-421, XP93023984 (2011).
Cheng, Yu-Ting et al. "Production of targeted aromatics by using Diels-Alder classes of reactions with furans and olefins over ZSM-5", Green Chemistry, 14(11):3114-3125, XP055068442 (2012).
Gosselink, Richard et al. "Lignin as a renewable aromatic resource for the chemical industry (Thesis) ", 1-196, XP93023331 (2011).
Gosselink, Richard et al. "Lignin as a renewable aromatic resource for the chemical industry (Mini-symposium organized by Wageningen UR Lignin Platform)", Wageningen Contents, 1-26, XP055271803 (2011).
Iskhakova, Gulnara et al. "Diels-Alder reaction between naphthalene and N-phenylmaleimide under ambient and high pressure conditions", 1-10, XP93023886 (2005).

(56) References Cited

OTHER PUBLICATIONS

Kamm, Birgit et al. "International biorefinery systems", Pure & Applied Chemistry, 79(11): 1983-1997, XP93023254 (2007).
Kim Sungjin et al. "Synthesis of 2,5-Diaminoquinones by One-Pot Copper-Catalyzed Aerobic Oxidation of Hydroquinones and Addition Reaction of Amines", Advanced Synthesis and Catalysis, 351(16):2573-2578, XP93023976 (2009).
Lange, Jean-Paul et al. "Lignocellulose conversion: an introduction to chemistry process and economics", Biofuels, Bioproducts & Biorefining, 1(1):39-48, XP93023325 (2007).
McCarthy, Joseph et al. "Lignin Chemistry, Technology, and Utilization: A Brief History" In: Chemistry, Process Design, and Safety for the Nitration Industry /ACS /Symposium Series, American Chemical Society/Oxford University Press, US, 1-99, XP93023322 (1999).
Ochoa-Gomez, Jose et al. "Industria Quimica Basada en Biomasa implicaciones tecnologicas", 1-106, XP93023315 (2007).
Qi Song et al. "Hydrogenolysis of lignosulfonate into phenols over heterogeneous nickel. catalysts", Chemical Communications, 48(56): 7019-7021, XP055157001 (2012).
Shao, Dan et al. "Electrochemical oxidation of 1ignin by two typical electrodes: Ti/Sb-SnO2 and Ti/PbO2", Chemical Engeneering Journal, 244:288-295, XP93023751 (2014).
Tarasov, Dmitry et al. "Production of Lignosulfonate in NSSC-Based Biorefinery", Biotechnology Progress, 31(6):1508-1514, XP093023239 (2015).
CAS Registry No. 783281-80-1; 2-Naphthalenesulfonic acid, 1,4-dihydro-3-methoxy-1,4-dioxo-, (2004).
CAS Registry No. 745756-46-1; 2,7-Naphthalenedisulfonic acid, 1,4-dihydro-3-(1-methylethoxy)-1,4-dioxo-, (2004).
Chemical Abstracts Accession No. 2012:1705525 (CAPlus), (2012).
Chemical Abstracts Accession No. 1964:468988 (CAPlus), (1964).
Chemical Abstracts Accession No. 1963:66335 (CAPlus); (1962).
Examination Report from corresponding Australian Application No. 2017246493 dated May 3, 2023.
Notice of Allowance issued in corresponding U.S. Appl. No. 17/177,567 dated Sep. 21, 2022.
Huskinson et al., "A metal-free organic-inorganic aqueous flow battery," Nature, 505(7482):195-198 (2014).
Non-Final Office Action from U.S. Appl. No. 17/842,079 dated Nov. 24, 2023.
Non-Final Office Action from U.S. Appl. No. 18/197,415 dated Feb. 14, 2024.
Office Action from corresponding CA Appln. No. 3,017,989 dated Jun. 7, 2024.
Non-Final Office Action from U.S. Appl. No. 18/611,202 dated Sep. 29, 2024.
Bidman, T.A. (2004). Oxidation of 2-alkyl-5, 10-dihydrophenazines. Russ J Gen Chem 74: 1433-1434.
Wei, et al., (2016). A turn-on fluorescent chemosensor selectively detects cyanide in pure water and food sample, Tetrahedron letters, 57:2767-2771.
European Search Report received in corresponding European Patent Application No. 19 758 645.6 dated Aug. 28, 2023.
Goulet, M., et al. (2019). Extending the Lifetime of Organic Flow Batteries via Redox State Management, Journal of the Americal Chemical Society, 141:8014-8019.
International Search Report and Written Opinion received for International Application No. PCT/EP2020/083927 mailed on Aug. 2, 2021.
Hollas, et al., (2018). A biometrick high-capacity phenazine-based anolyte for acqueous organic redox fllow batteries, Nature Energy, 3: (6): 508-514.
Ninsberg et al. (2016). TEMPO/Phenazine Combi-Molecule: A redox-active material for symmetric acqueous redox-flow batteries, ACS Energy Letters, 1(5): 976-980.
International Search Report from corresponding PCT Application No. PCT/EP2020/083958 dated Sep. 7, 2021.
Written Opinion from corresponding PCT Application No. PCT/EP2020/083958 dated Sep. 7, 2021.
Search Report from corresponding PCT Application No. PCT/EP2021/085110 dated Jul. 13, 2022.
Opinion from corresponding PCT Application No. PCT/EP2021/085110 dated Jul. 13, 2022.
Wang, Y., et al., "One-step electrodeposition of polyaniline/nickel hexacyanoferrate/sulfonated carbon nanotubes interconnected composite films for supercapacitor," J. Solid State Electrochem, 19: 3157-3168 (2015).
Chalamala, B.R., et al., "Redox Flow Batteries: An Engineering Perspective," Proceedings of the IEEE, 102(6): 976-999 (2014).
International Search Report from PCT Application No. PCT/EP2021/062040 dated Feb. 9, 2022.
Written Opinion from PCT Application No. PCT/EP2021/062040 dated Feb. 9, 2022.
Viault, G., et al. (2011). Synthesis of a Focused Chemical Library Based on Derivatives of Embelin, a Natural Product with Proapoptotic and Anticancer Properties. Eur. J. Org. Chem., 2011(7): 1233-1241.
Nagase, Y., et al. (1954). Oxidation of Naphthols with Hydrogen Peroxide in Alkaline Media. Journal of the Pharmaceutical Society of Japan, 74(1): 9-13.
Ettel, V., et al. (1956). Oxidation of pyrocatechol. II. Oxidation in alkaline solution. Chemicke Listy Pro Vedu a Prumysl, Praha, Czechia, 51: 1153-1158.
Xiao, B., et al. (2008). Syntheses and structural characteristics of copper(II)-organic polymers based on N-heterocyclic ligands: A study on the importance of steric factors in the design of potent catalysts. Journal of Molecular Catalysis, 288(1-2): 42-51.
Non-Final Office Action from U.S. Appl. No. 18/036,557 dated Nov. 26, 2025.
Examination Report from Indian Application No. 202217043089 dated Nov. 13, 2025.
Non-Final Office Action from U.S. Appl. No. 18/031,751 dated Dec. 5, 2025.

* cited by examiner

| Phenazine | Charge plateau [V] | Discharge plateau [V] | RTE [%] | OCV [V] at SOC= 100% | Used voltage cut-offs [V] |
|---|---|---|---|---|---|
| II | 1,40-1,55 | 1,35-1,20 | 82 | 1,54 | 1,7-1,0 |

PHENAZINE-BASED COMPOUNDS

This application is a U.S. National Phase application under 35 U.S.C. § 371 of PCT/EP2021/054344, filed Feb. 22, 2021, which claims priority from and the benefit of PCT/EP2020/054568, filed Feb. 20, 2020, the specifications of which are hereby incorporated by reference in their entireties into the instant application.

In recent years, concerns resulting from environmental consequences of exploiting fossil fuels as the main energy sources have led to an increasing prominence of renewable-energy systems (e.g., solar- and wind-based systems). The intermittent nature of such renewable energy sources however makes it difficult to fully integrate these energy sources into electrical power grids and distribution networks. A solution to this problem are large-scale electrical energy storage (EES) systems, which are also vital for the smart grid and distributed power generation development. Another important application of EES is electrification of on-ground transportation, as the replacement of traditional combustion engines with hybrid, plug-in hybrid, and pure electric vehicles (EVs) allows for reduction of carbon emissions and fuel savings (Soloveichik G. L. Chem. Rev. 2015, 115, 11533-11558).

The U.S. Department of Energy has identified four major challenges to the widespread implementation of EES: cost, reliability and safety, equitable regulatory environments, and industry acceptance. The development of novel EES technologies capable of resolving these challenges is critical (Soloveichik G. L. Chem. Rev. 2015, 115, 11533-11558). Redox-flow batteries (RFBs)—first developed by NASA during the energy crisis of the 1970's and currently entering a period of renaissance—are among the most promising scalable EES technologies. RFBs are electrochemical systems that can repeatedly store and convert electrical energy to chemical energy and vice versa when needed. Redox reactions are employed to store energy in the form of a chemical potential in liquid electrolyte solutions which flow through a battery of electrochemical cells during charge and discharge. The stored electrochemical energy can be converted to electrical energy upon discharge with concomitant reversal of the opposite redox reactions.

RFBs usually include a positive electrode (cathode) and a negative electrode (anode) in separated cells and separated by an ion-exchange membrane, and two circulating electrolyte solutions, positive and negative electrolyte flow streams, generally referred to as the "catholyte" and "anolyte", respectively. Energy conversion between electrical energy and chemical potential occurs instantly at the electrodes, once the electrolyte solutions begin to flow through the cell. During discharge, electrons are released via an oxidation reaction from a high chemical potential state on the anode of the battery and subsequently move through an external circuit. Finally, the electrons are accepted via a reduction reaction at a lower chemical potential state on the cathode of the battery. Redox-flow batteries can be recharged by inversing the flow of the redox fluids and applying current to the electrochemical reactor.

The capacity and energy of redox flow batteries is determined by the total amount of redox active species for a set system available in the volume of electrolyte solution, whereas their current (power) depends on the number of atoms or molecules of the active chemical species that are reacted within the redox flow battery cell as a function of time. Redox-flow batteries thus have the advantage that their capacity (energy) and their current the (power) can be readily separated, and therefore readily up-scaled. Thus, capacity (energy) can be increased by increasing the number or size of the electrolyte tanks whereas the current (power) is controlled by controlling the number and size of the current collectors. Since energy and power of RFB systems are independent variables, RFBs are inherently well suitable for large applications, since they scale-up in a more cost-effective manner than other batteries. Moreover, RFBs provide a unique design flexibility as the required capacities for any application can be provided using tailor-made energy and power modules.

A well-established example of an RFB is the vanadium redox flow battery, which contains redox couples exclusively based on vanadium cations. Nevertheless, there is also a wide range of less commonly used inorganic flow cell chemistries, including the polysulfide-bromide battery (PSB). The wide-scale utilization of RFBs using inorganic redox materials is presently still limited by availability and costs of the redox materials. That holds even more so, whenever the redox materials are based on redox-active transition metals such as vanadium, and/or require precious-metal electro-catalysts. Toxicity (and associated health and environmental risks) of inorganic redox materials (such as vanadium salts or bromine) further limits applicability of inorganic RFBs for energy storage. That holds in particular when applying distributed, modular energy generation technologies that use (intermittent) "green power", such as wind, photovoltaic, or hydroelectric power. Also, the incorporated materials may constitute overheating, fire or explosion risks.

In view of the disadvantages of RFBs based on inorganic redox species, RFBs were envisaged with different organic compounds. Novel organic redox active species for large-scale use in redox flow batteries should preferably be inexpensive, with high solubility and redox potential, and exhibit fast electrode kinetics. In early 2014, Huskinson et al. developed a metal-free flow battery based on 9,10-anthraquinone-2,7-disulphonic acid (AQDS) (Huskinson et al. Nature 2014, 505, 195-198 and WO 2014/052682 A2). Yang et al. reported on an organic redox flow battery with 1,2-benzoquinone-3,5-disulfonic acid (BQDS) as the catholyte, while AQDS or anthraquinone-2-sulfonic acid (AQS) was used as the anolyte (Yang et al. J. Electrochem. Soc. 2014, 161, A1371-A1380). However, sheer volume of needed energy storage demands millions of tons of active materials. To date, only a smaller number of organic chemicals are produced worldwide at such a scale (e.g., methanol, acetic acid, and phenol). Based on scale and availability, the "ideal" redox flow battery for large-scale deployment should be aqueous and use highly soluble multi-electron (i.e. highly energy dense) redox active species that are readily available and inexpensive as electrolytes. Derivatized anthra- and benzoquinones suggested as electrolytes by Huskinson et al. and Yang et al. are commercially available; however, costly and elaborate manufacture of any of them severely limits their broad-range, large-scale employment.

In summary, despite recent advantages in the development of rechargeable batteries, a long-felt need exists for safe, inexpensive, easy-to-use, reliable and efficient technologies for energy storage that enables diversification of energy supply and optimization of the energy grid, including increased penetration and utilization of renewable energies. By to their unique ability to decouple power and capacity functions, redox flow batteries are at least in principle well suitable for large scale energy storage applications. However, development efforts have not yet achieved large-scale employment of RFBs.

Moreover, existing redox flow batteries suffer from the reliance on battery chemistries that result in high costs of active materials and system engineering, low cell and system performance (e.g. round trip energy efficiency), poor cycle life and toxicity. Thus, there remains a need for novel electroactive redox materials, which are readily available at low cost and exhibit reduced toxicity. Preferably, such electrolytes further provide for a high energy density, a high operating potential, increased cell output voltage and extended lifetime. Accordingly, there is a need in the art for improved redox flow battery chemistries and systems.

The present invention is directed to novel phenazine-based compounds, i.e. compounds having a phenazine ring skeleton characterized by specific substitution patterns, and their application as redox active components, especially for use as negolytes and for use in redox flow batteries (RFBs) containing these phenazines as a redox active species for at least one half-cell of the redox flow battery. The phenazine compounds of the present invention were found to be specifically advantageous as redox-active species due to their improved electrochemical performance, increased water solubility, stability under operation (longevity) and/or their accelerated oxidation/reduction kinetics. Their characteristics render the inventive compounds also suitable for use as a reduction agent.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the features of the present invention will be described. These features are described for specific embodiments. It should, however, be understood that they may be combined in any manner and in any number to generate additional embodiments. The variously described examples and preferred embodiments, should not be construed to limit the present invention to only explicitly described embodiments. This present description should be understood to support and encompass embodiments, which combine the explicitly described embodiments, with any number of the disclosed and/or preferred features. Furthermore, any permutations and combinations of all described features in this application shall be considered supported by the description of the present application, unless it is understood otherwise.

The present invention provides a substituted phenazine compound characterized by Formula (I)

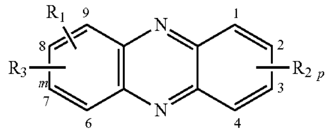

(oxidized state: I(a))

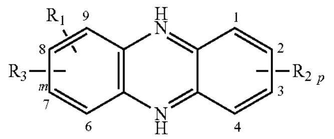

(reduced state: I(b))

wherein $R_1$ is selected from the group consisting of $R_d$, $R_b$—$R_c$, $R_d(R_c)_y$, $R_a$—$R_d$—$R_c$, $R_a$—$R_b$—$R_c$, $R_d$—$R_a$—$R_d$—$R_c$, $R_b$—$R_a$—$R_d$—$R_c$, $R_d$—$R_a$—$R_b$—$R_c$, $R_e(R_d$—$R_c)_2$, $N(R_b$—$R_c)_3X$, —$N(R_d$—$R_c)_3X$, $R_e(R_d$—$R_c)(R_b$—$R_c)$, $R_e(R_b$—$R_c)_2$ and $R_b$—$R_a$—$R_b$—$R_c$;

$R_2$ and $R_3$ are selected independently from each other from the group consisting of $R_a$—$R_b$—$R_c$, $R_a$—$R_d$—$R_c$, $R_b$—$R_c$, $R_d$—$R_c$, $R_b$—$R_a$—$R_b$—$R_c$, $R_d$—$R_a$—$R_b$—$R_c$, $R_d$—$R_a$—$R_d$—$R_c$, $R_b$—$R_a$—$R_d$—$R_c$, $R_e(R_b$—$R_c)_2$, $R_e$ $(R_d$—$R_c)_2$, $R_e$ $(R_d$—$R_c)(R_b$—$R_c)$, $R_b$—$R_e$ $(R_b$—$R_c)_z$, $R_d$—$R_e(R_b$—$R_c)_2$, $R_b$—$R_e(R_d$—$R_c)_z$, $R_d$—$R_e(R_d$—$R_c)_2$, $R_d$, $R_a$—$R_d$, —$N(R_b$—$R_c)_3X$, —$N(R_d$—$R_c)_3X$, $R_b$—$N(R_b$—$R_c)_3X$, $R_d$—$N(R_b$—$R_c)_3X$, $R_b$—$N(R_d$—$R_c)_3X$, and $R_d$—$N(R_d$—$R_c)_3X$;

wherein $R_a$ is selected from the group consisting of

—$SO_3$—, —$SO_2(NH)$—, —$(NH)SO_2$—, —$SO_2(NR_d)$—, —$(NR_d)SO_2$—, —$OSO_3$—, —$OSO_2(NH)$—, —$(NH)SO_2O$—, —$OSO_2NR_d$—, —$(NR_d)SO_2O$—, —$PO_3H$—, —$PO_2H(NH)$—, —$PO_2HNR_d$—, —$OPO_3H$—, —$OPO_2H(NH)$—, —$OPO_2HNR_d$—, —$CO_2$—, —$CO(NH)$—, —$(NH)CO$—, —$CONR_d$—, —$(NR_d)CO$—, —O—, —NH—, —$NR_d$—, -heteroaryl-, and -heterocyclyl-;

$R_b$ is selected from the group consisting of

—$CH_2C(OH)HR_d$—, —$R_d$—O—$R_d$—, —$R_d$—$(OC_2H_4)_n$—, and —$R_d$—$(OCH_2C(CH_3)H)_n$—;

$R_c$ is selected from the group consisting of

—H, —OH, —$OR_d$, —$OC(=O)R_d$, —$NH_2$, —$NH(R_d)$, —$N(R_d)_2$, —$N(R_d)_3X$, —$C(=O)NH_2$, —$C(=O)(NH)R_d$, —$C(=O)OH$, —$C(=O)R_b$—H, —$SO_3H$, —$SO_3R_d$, —$SO_2NH_2$, —$SO_2(NH)R_d$, —$OSO_3H$, —$OSO_3R_d$, —$OSO_2NH_2$, —$OSO_2(NH)R_d$, —$PO_3H_2$, —$PO_3HR_d$, —$PO_3(R_d)_2$, —$OPO_3H_2$, —$OPO_3HR_d$, —$OPO_3(R_d)_2$, -halogen, -aryl, —CHO, —CN, -heteroaryl, and -heterocyclyl; or two groups $R_c$ together form a bond or a group of formula —O—, —NH— or —$NR_d$—;

$R_d$ is selected from the group consisting of a linear or branched, saturated or unsaturated $C_1$-$C_9$ hydrocarbon group;

$R_e$ is selected from the group consisting of $PO_3$, $OPO_2$, and N;

or two of $R_1$, $R_2$ and/or $R_3$ being adjacent substituents on the phenazine ring system together form a cyclic system.

and wherein

X is selected from the group consisting of $Cl^-$, $Br^-$, $I^-$, and $\frac{1}{2}SO_4^{2-}$;

m is selected from any number of 0, 1, 2, and 3;

p is selected from any number of 0, 1, 2, 3, and 4;

y is selected from any number of 2, 3, 4, 5, and 6; and n is selected from any number of 1 to 50;

or a salt thereof.

The phenazine compound may be a cation such that the counter-ion of the salt is an anion which may be a halogenide, e.g. chloride, or sulfate, carbonate, $BF_4^-$, $PF_6^-$, $ClO_4^-$ or an organic counter-ion, e.g. acetate, etc. More preferably, the phenazine compound may be an anion such that the counter-ion of the salt is a cation which may be selected from an alkali metal, e.g. sodium, potassium, or an earth alkali metal, e.g. calcium or magnesium, iron, copper, zinc etc, preferably from an alkali metal or a combination of alkali metals.

In another specific embodiment $R^1$ may be defined as defined for $R^3$ according to formula (I). "Two of $R^1$, $R^2$ and/or $R^3$" is meant to either represent two $R^1$ or $R^2$ or $R^3$ being adjacent substituents on the phenazine ring system, thus together forming a cyclic (aromatic or non-aromatic) system. Or the two substituents may be selected from a combination of $R^1$ and $R^2$, $R^1$ and $R^3$ and $R^2$ and $R^3$.

According to a preferred embodiment the present invention provides a substituted phenazine compound as defined above, wherein $R_a$ of $R_a—R_d—R_c$ is selected from —NH—, —$SO_3$—, —$SO_2$(NH)—, —(NH)$SO_2$—, —$SO_2$($NR_d$)—, —($NR_d$)$SO_2$—, —$OSO_3$—, —$OSO_2$(NH)—, —(NH)$SO_2$O—, —$OSO_2NR_d$—, —($NR_d$)$SO_2$O—, —$PO_3$H—, —$PO_2$H(NH)—, —$PO_2HNR_d$—, —$OPO_3$H—, —$OPO_2$H(NH)—, —$OPO_2HNR_d$—, —(NH)CO— or —($NR_d$)CO—, and $R_c$ of $R_a—R_d—R_c$ is any substituent as defined other than —H, and $R_1$ is any substituent as defined other than $R_d$;

or $R_c$ of $R_e(R_b—R_c)_2$, $R_e(R_d—R_c)_2$, $R_e(R_d—R_c)(R_b—R_c)$ and $R_d(R_c)_y$ is any substituent as defined other than —H, and $R_1$ is any substituent as defined other than $R_d$.

According to a further preferred embodiment the present invention provides a substituted phenazine compound as defined above, wherein $R_1$ is selected from the group consisting of $R_b—R_c$, $R_d$ $(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, $R_e(R_d—R_c)_2$, $N(R_b—R_c)_3X$, —$N(R_d—R_c)_3X$, $R_e(R_d—R_c)(R_b—R_c)$, $R_e(R_b—R_c)_2$ and Rb-Ra-Rb-Rc;

$R^2$ and $R^3$ are selected independently from each other from the group consisting of $R_a—R_b—R_c$, $R_a—R_d—R_c$, $R_b—R_c$, $R_b—R_a—R_b—R_c$, $R_d—R_a—R_b—R_c$, $R_b—R_a—R_d—R_c$, $R_e(R_b—R_c)_2$, $R_e(R_d—R_c)_2$, $R_e(R_d—R_c)(R_b—R_c)$, $R_b—R_e(R_b—R_c)_2$, $R_d—R_e(R_b—R_c)_2$, $R_b—R_e(R_d—R_c)_2R_d$, —$N(R_b—R_c)_3X$, —$N(R_d—R_c)_3X$, $R_b—N(R_b—R_c)_3X$, and $R_b—N(R_d—R_c)_3X$;

wherein $R_a$ is selected from the group consisting of

—$SO_3$—, —$SO_2$(NH)—, —(NH)$SO_2$—, —$SO_2$($NR_d$)—, —($NR_d$)$SO_2$—, —$OSO_3$—, —$OSO_2$(NH)—, —(NH)$SO_2$O—, —$OSO_2NR_d$—, —($NR_d$)$SO_2$O—, —CO(NH)—, —(NH)CO—, —$CONR_d$—, —($NR_d$)CO—, —O—, —NH—, -heteroaryl-, and -heterocyclyl-;

$R_b$ is selected from the group consisting of

—$CH_2C(OH)HR_d$— and —$R_d$—$(OCH_2C(CH_3)H)_n$—;

$R_c$ is selected from the group consisting of

—H, —OH, —$OR_d$, —$NH_2$, —$NH(R_d)$, —$N(R_d)_2$, —$N(R_d)_3X$, —C(═O)$NH_2$, —C(═O)(NH)$R_d$, —C(═O)OH, —$SO_3$H, —$SO_3R_d$, —$SO_2NH_2$, —$SO_2$(NH)$R_d$, —$OSO_3$H, —$OSO_3R_d$, —$OSO_2NH_2$, —$OSO_2$(N H) $R_d$, and -halogen;

$R_d$ is selected from the group consisting of a linear or branched, saturated or unsaturated $C_1$-$C_9$ hydrocarbon group;

$R_e$ is selected from the group consisting of $PO_3$, $OPO_2$, and N;

and wherein

X is selected from the group consisting of $Cl^-$, $Br^-$, $I^-$, and $\frac{1}{2}SO_4^{2-}$;

m is selected from any number of 0, 1, 2, and 3;

p is selected from any number of 0, 1, 2, 3, and 4;

y is selected from any number of 2, 3, 4, 5, and 6; and n is selected from any number of 1 to 50.

According to another preferred embodiment the present invention provides a substituted phenazine compound as defined above, wherein $R^1$ is selected from the group consisting of $R_b—R_c$, $R_d(R_c)_y$, $R_a—R_b—R_c$, $R_b—R_a—R_d—R_c$, $R_d—R_a—R_b—R_c$, $R_b—R_a—R_b—R_c$, $R_a—R_d—R_c$, $R_e(R_d—R_c)_2$, $R_e(R_d—R_c)(R_b—R_c)$, $R_e(R_b—R_c)_2$, wherein $R_c$ in $R_d(R_c)_y$ and $R_e(R_d—R_c)_2$ is any substituent as defined other than H.

According to a further preferred embodiment the present invention provides a substituted phenazine compound as defined above, wherein $R^1$ is selected from the group consisting of $R_b—R_c$, $R_d$ $(R_c)_y$, $R_a—R_b—R_c$, $R_b—R_a—R_d—R_c$, $R_d—R_a—R_b—R_c$, and $R_b—R_a—R_b—R_c$.

According to another preferred embodiment the present invention provides a substituted phenazine compound as defined above, wherein $R_2$ and $R_3$ are selected independently from each other from the group consisting of $R_a—R_b—R_c$, $R_b—R_a—R_b—R_c$, $R_d—R_a—R_b—R_c$, $R_b—R_a—R_d—R_c$, $R_e(R_b—R_c)_2$, $R_e(R_d—R_c)_2$, $R_e(R_d—R_c)(R_b—R_c)$, $R_b—R_e(R_b—R_c)_2$, $R_d—R_e(R_b—R_c)_2$, $R_b—R_e(R_d—R_c)_2$, $R_d$, —$N(R_b—R_c)_3X$, and —$N(R_d—R_c)_3X$, with $R_2$ preferably being selected from $R_d$.

According to another preferred embodiment the present invention provides a substituted phenazine compound as defined above, wherein $R_a$ is selected from the group consisting of —$SO_3$—, —$SO_2$(NH)—, —(NH)$SO_2$—, —$OSO_3$—, —$OSO_2$(NH)—, —(NH)$SO_2$O—, —CO(NH)—, —(NH)CO—, —O—, and —NH—.

According to another preferred embodiment the present invention provides a substituted phenazine compound as defined above, wherein $R_b$ is selected from the group consisting of —$CH_2C(OH)HR_d$— and —$R_d$—$(OCH_2C(CH_3)H)_n$—.

According to another preferred embodiment the present invention provides a substituted phenazine compound as defined above, wherein $R_c$ is selected from the group consisting of —H, —OH, —$OR_d$, —$NH_2$, —$N(R_d)_2$, —$N(R_d)_3X$, C(═O)$NH_2$, C(═O)(NH)$R_d$, C(═O)OH, —$SO_3$H, —$OSO_3$H, and —$OSO_2$(NH)$R_d$, with $R_c$ preferably being selected from —H, —OH, —$SO_3$H and —C(═O)OH.

According to another preferred embodiment the present invention provides a substituted phenazine compound as defined above, wherein $R_d$ is selected from the group consisting of a linear or branched, saturated or unsaturated $C_1$-$C_5$ hydrocarbon group, preferably a linear, saturated $C_1$ to $C_5$ hydrocarbon group.

According to a further preferred embodiment the present invention provides a substituted phenazine compound as defined above, wherein $R_e$ is selected from N.

According to another preferred embodiment the present invention provides a substituted phenazine compound as defined above, wherein X is selected from the group consisting of $Cl^-$, and $\frac{1}{2}SO_4^{2-}$.

According to a further preferred embodiment the present invention provides a substituted phenazine compound as defined above, wherein m is selected from 0 or 1.

According to another preferred embodiment the present invention provides a substituted phenazine compound as defined above, wherein p is selected from any number of 0, 1, 2, and 3, in particular 1, 2 and 3.

According to a further preferred embodiment the present invention provides a substituted phenazine compound as defined above, wherein y is selected from 2 or 3.

According to another preferred embodiment the present invention provides a substituted phenazine compound as defined above, wherein n is selected from any number of 1 to 10 or 1 to 5.

According to a further preferred embodiment the present invention provides a substituted phenazine compound as defined above, wherein $R_1$ is selected from one or more of (i) to (ix)

(i) $R_d$, $R_b—R_c$, $R_d(R_c)_y$, $R_a—R_d—R_c$, $R_a—R_b—R_c$, $R_d—R_a—R_d—R_c$, $R_b—R_a—R_d—R_c$, and $R_b—R_a—R_b—R_c$;

(ii) $R_d$, $R_b—R_c$, $R_d(R_c)_y$, $R_a—R_d—R_c$, $R_a—R_b—R_c$, $R_d—R_a—R_d—R_c$, $R_b—R_a—R_d—R_c$, and $R_d—R_a—R_b—R_c$;

(iii) $R_d$, $R_b—R_c$, $R_d(R_c)_y$, $R_a—R_d—R_c$, $R_a—R_b—R_c$, $R_d—R_a—R_d—R_c$, $R_d—R_a—R_b—R_c$ and $R_b—R_a—R_b—R_c$;

(iv) $R_d$, $R_b—R_c$, $R_d(R_c)_y$, $R_a—R_d—R_c$, $R_a—R_b—R_c$, $R_b—R_a—R_d—R_c$, $R_d—R_a—R_b—R_c$ and $R_b—R_a—R_b—R_c$;

(v) $R_d$, $R_b—R_c$, $R_d(R_c)_y$, $R_a—R_d—R_c$, $R_d—R_a—R_d—R_c$, $R_b—R_a—R_d—R_c$, $R_d—R_a—R_b—R_c$, and $R_b—R_a—R_b—R_c$;

(vi) $R_d$, $R_b—R_c$, $R_d(R_c)_y$, $R_a—R_b—R_c$, $R_d—R_a—R_d—R_c$, $R_b—R_a—R_d—R_c$, $R_d—R_a—R_b—R_c$ and $R_b—R_a—R_b—R_c$;

(vii) $R_d$, $R_b—R_c$, $R_a—R_d—R_c$, $R_a—R_b—R_c$, $R_d—R_a—R_d—R_c$, $R_b—R_a—R_d—R_c$, $R_d—R_a—R_b—R_c$ and $R_b—R_a—R_b—R_c$;

(viii) $R_d$, $R_d(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, and $R_b—R_a—R_b—R_c$; or (ix) $R_b—R_c$, $R_d(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, and $R_b—R_a—R_b—R_c$.

Also preferred are substituted phenazine compounds as defined above, wherein $R_1$ is selected from one or more of (i) to (xi ii)

(i) $R_d$, $R_b—R_c$, $R_d(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, $R_b—R_a—R_b—R_c$, $R_e(R_d—R_c)_2$, $N(R_b—R_c)_3X$, $—N(R_d—R_c)_3X$, and $R_e(R_d—R_c)(R_b—R_c)$;

(ii) $R_d$, $R_b—R_c$, $R_d(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, $R_b—R_a—R_b—R_c$, $R_e(R_d—R_c)_2$, $N(R_b—R_c)_3X$, $N(R_d—R_c)_3X$, and $R_e(R_b—R_c)_2$, $R_d$, $R_b—R_c$, $R_d(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, $R_b—R_a—R_b—R_c$, $R_e(R_d—R_c)_2$, $N(R_b—R_c)_3X$, $R_e(R_d—R_c)(R_b—R_c)$, and $R_e(R_b—R_c)_2$;

(iii) $R_d$, $R_b—R_c$, $R_d(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, $R_b—R_a—R_b—R_c$, $R_e(R_d—R_c)_2$, $—N(R_d—R_c)_3X$, $R_e(R_d—R_c)(R_b—R_c)$, and $R_e(R_b—R_c)_2$;

(iv) $R_d$, $R_b—R_c$, $R_d(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, $R_b—R_a—R_b—R_c$, $N(R_b—R_c)_3X$, $—N(R_d—R_c)_3X$, $R_e(R_d—R_c)(R_b—R_c)$, and $R_e(R_b—R_c)_2$;

(v) $R_d$, $R_b—R_c$, $R_d$ $(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, $R_e$ $(R_d—R_c)_2$, $N(R_b—R_c)_3X$, $—N(R_d—R_c)_3X$, $R_e(R_d—R_c)(R_b—R_c)$, and $R_e(R_b—R_c)_2$;

(vi) $R_d$, $R_b—R_c$, $R_d(R_c)_y$, $R_a—R_d—R_c$, $R_a—R_b—R_c$, $R_d—R_a—R_d—R_c$, $R_b—R_a—R_d—R_c$, $R_b—R_a—R_b—R_c$, $R_e(R_d—R_c)_2$, $N(R_b—R_c)_3X$, $—N(R_d—R_c)_3X$, $R_e(R_d—R_c)(R_b—R_c)$, and $R_e(R_b—R_c)_2$;

(vii) $R_d$, $R_b—R_c$, $R_d(R_c)_y$, $R_a—R_d—R_c$, $R_a—R_b—R_c$, $R_d—R_a—R_d—R_c$, $R_d—R_a—R_b—R_c$, $R_b—R_a—R_b—R_c$, $R_e(R_d—R_c)_2$, $N(R_b—R_c)_3X$, $—N(R_d—R_c)_3X$, $R_e(R_d—R_c)(R_b—R_c)$, and $R_e(R_b—R_c)_2$;

(viii) $R_d$, $R_b—R_c$, $R_d(R_c)_y$, $R_a—R_d—R_c$, $R_a—R_b—R_c$, $R_b—R_a—R_d—R_c$, $R_d—R_a—R_b—R_c$, $R_b—R_a—R_b—R_c$, $R_e(R_d—R_c)_2$, $N(R_b—R_c)_3X$, $—N(R_d—R_c)_3X$, $R_e(R_d—R_c)(R_b—R_c)$, and $R_e(R_b—R_c)_2$, (ix) $R_d$, $R_b—R_c$, $R_d(R_c)_y$, $R_a—R_d—R_c$, $R_d—R_a—R_d—R_c$, $R_b—R_a—R_d—R_c$, $R_d—R_a—R_b—R_c$, $R_b—R_a—R_b—R_c$, $R_e(R_d—R_c)_2$, $N(R_b—R_c)_3X$, $—N(R_d—R_c)_3X$, $R_e(R_d—R_c)(R_b—R_c)$, and $R_e(R_b—R_c)_2$, (x) $R_d$, $R_b—R_c$, $R_d(R_c)_y$, $R_a—R_b—R_c$, $R_d—R_a—R_d—R_c$, $R_b—R_a—R_d—R_c$, $R_d—R_a—R_b—R_c$, $R_b—R_a—R_b—R_c$, $R_e(R_d—R_c)_2$, $N(R_b—R_c)_3X$, $—N(R_d—R_c)_3X$, $R_e(R_d—R_c)(R_b—R_c)$, and $R_e(R_b—R_c)_2$, (xi) $R_d$, $R_b—R_c$, $R_a—R_d—R_c$, $R_a—R_b—R_c$, $R_d—R_a—R_d—R_c$, $R_b—R_a—R_d—R_c$, $R_d—R_a—R_b—R_c$, $R_b—R_a—R_b—R_c$, $R_e(R_d—R_c)_2$, $N(R_b—R_c)_3X$, $—N(R_d—R_c)_3X$, $R_e(R_d—R_c)(R_b—R_c)$, and $R_e(R_b—R_c)_2$, (xii) $R_d$, $R_d(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, $R_b—R_a—R_b—R_c$, $R_e(R_d—R_c)_2$, $N(R_b—R_c)_3X$, $—N(R_d—R_c)_3X$, $R_e(R_d—R_c)(R_b—R_c)$, and $R_e(R_b—R_c)_2$; or (xiii) $R_b—R_c$, $R_d(R_c)_y$, $R_a—R_d—R_c$, $R_a—R_b—R_c$, $R_d—R_a—R_d—R_c$, $R_b—R_a—R_d—R_c$, $R_d—R_a—R_b—R_c$, $R_b—R_a—R_b—R_c$, $R_e(R_d—R_c)_2$, $N(R_b—R_c)_3X$, $—N(R_d—R_c)_3X$, $R_e(R_d—R_c)(R_b—R_c)$, and $R_e(R_b—R_c)_2$.

According to another preferred embodiment the present invention provides a substituted phenazine compound as defined above, wherein $R_1$ is selected from one or more of (i) to (xxxvi)

(i) Rd and Rb-Rc;

(ii) Rd and Rd(Rc)$_y$;

(iii) Rd and Ra-Rd-Rc;

(iv) Rd and Ra-Rb-Rc;

(v) Rd and Rd-Ra-Rd-Rc;

(vi) Rd and Rb-Ra-Rd-Rc;

(vii) Rd and Rd-Ra-Rb-Rc;

(viii) Rd and Rb-Ra-Rb-Rc;

(ix) Rb-Rc and Rd(Rc)$_y$;

(x) Rb-Rc and Ra-Rd-Rc;

(xi) Rb-Rc and Ra-Rb-Rc;

(xii) Rb-Rc and Rd-Ra-Rd-Rc;

(xiii) Rb-Rc and Rb-Ra-Rd-Rc;

(xiv) Rb-Rc and Rd-Ra-Rb-Rc;

(xv) Rb-Rc and Rb-Ra-Rb-Rc;
(xvi) $Rd(Rc)_y$ and Ra-Rd-Rc;
(xvii) $Rd(Rc)_y$ and Ra-Rb-Rc;
(xviii) $Rd(Rc)_y$ and Rd-Ra-Rd-Rc;
(xix) $Rd(Rc)_y$ and Rb-Ra-Rd-Rc;
(xx) $Rd(Rc)_y$ and Rd-Ra-Rb-Rc;
(xxi) $Rd(Rc)_y$ and Rb-Ra-Rb-Rc;
(xxii) Ra-Rd-Rc and Ra-Rb-Rc;
(xxiii) Ra-Rd-Rc and Rd-Ra-Rd-Rc;
(xxiv) Ra-Rd-Rc and Rb-Ra-Rd-Rc;
(xxv) Ra-Rd-Rc and Rd-Ra-Rb-Rc;
(xxvi) Ra-Rd-Rc and Rb-Ra-Rb-Rc;
(xxvii) Ra-Rb-Rc and Rd-Ra-Rd-Rc;
(xxviii) Ra-Rb-Rc and Rb-Ra-Rd-Rc;
(xxix) Ra-Rb-Rc and Rd-Ra-Rb-Rc;
(xxx) Ra-Rb-Rc and Rb-Ra-Rb-Rc;
(xxxi) Rd-Ra-Rd-Rc and Rb-Ra-Rd-Rc;
(xxxii) Rd-Ra-Rd-Rc and Rd-Ra-Rb-Rc;
(xxxiii) Rd-Ra-Rd-Rc and Rb-Ra-Rb-Rc;
(xxxiv) Rb-Ra-Rd-Rc and Rd-Ra-Rb-Rc;
(xxxv) Rb-Ra-Rd-Rc and Rb-Ra-Rb-Rc; or
(xxxvi) Rd-Ra-Rb-Rc and Rb-Ra-Rb-Rc, in particular, (ix) Rb-Rc and $Rd(Rc)_y$;
(xi) Rb-Rc and Ra-Rb-Rc;
(xiii) Rb-Rc and Rb-Ra-Rd-Rc;
(xiv) Rb-Rc and Rd-Ra-Rb-Rc;
(xv) Rb-Rc and Rb-Ra-Rb-Rc;
(xvii) $Rd(Rc)_y$ and Ra-Rb-Rc;
(xix) $Rd(Rc)_y$ and Rb-Ra-Rd-Rc;
(xx) $Rd(Rc)_y$ and Rd-Ra-Rb-Rc;
(xxi) $Rd(Rc)_y$ and Rb-Ra-Rb-Rc;
(xxviii) Ra-Rb-Rc and Rb-Ra-Rd-Rc;
(xxix) Ra-Rb-Rc and Rd-Ra-Rb-Rc;
(xxx) Ra-Rb-Rc and Rb-Ra-Rb-Rc;
(xxxiv) Rb-Ra-Rd-Rc and Rd-Ra-Rb-Rc;
(xxxv) Rb-Ra-Rd-Rc and Rb-Ra-Rb-Rc; or
(xxxvi) Rd-Ra-Rb-Rc and Rb-Ra-Rb-Rc.

According to a further preferred embodiment the present invention provides a substituted phenazine compound as defined above, wherein $R_1$ is selected from one or more of (i) to (xx)

(i) Rb-Rc, $Rd(Rc)_y$, and Ra-Rb-Rc;
(ii) Rb-Rc, $Rd(Rc)_y$, and Rb-Ra-Rd-Rc;
(iii) Rb-Rc, $Rd(Rc)_y$, and Rd-Ra-Rb-Rc;
(iv) Rb-Rc, $Rd(Rc)_y$, and Rb-Ra-Rb-Rc;
(v) Rb-Rc, Ra-Rb-Rc, and Rb-Ra-Rd-Rc;
(vi) Rb-Rc, Ra-Rb-Rc and Rd-Ra-Rb-Rc;
(vii) Rb-Rc, Ra-Rb-Rc and Rb-Ra-Rb-Rc;
(viii) Rb-Rc, Rb-Ra-Rd-Rc, and Rd-Ra-Rb-Rc;
(ix) Rb-Rc, Rb-Ra-Rd-Rc, and Rb-Ra-Rb-Rc;
(x) Rb-Rc, Rd-Ra-Rb-Rc, and Rb-Ra-Rb-Rc;
(xi) $Rd(Rc)_y$, Ra-Rb-Rc, and Rb-Ra-Rd-Rc;
(xii) $Rd(Rc)_y$, Ra-Rb-Rc, and Rd-Ra-Rb-Rc;
(xiii) $Rd(Rc)_y$, Ra-Rb-Rc, and Rb-Ra-Rd-Rc;
(xiv) $Rd(Rc)_y$ Rd-Ra-Rb-Rc, and Rb-Ra-Rb-Rc;
(xv) $Rd(Rc)_y$, Rb-Ra-Rd-Rc, and Rd-Ra-Rb-Rc;
(xvi) $Rd(Rc)_y$, Rb-Ra-Rd-Rc, and Rb-Ra-Rb-Rc;
(xvii) Ra-Rb-Rc, Rb-Ra-Rd-Rc, and Rd-Ra-Rb-Rc;
(xviii) Ra-Rb-Rc, Rb-Ra-Rd-Rc, and Rb-Ra-Rb-Rc;
(xix) Ra-Rb-Rc, Rb-Ra-Rd-Rc, and Rb-Ra-Rb-Rc; or
(xx) Rb-Ra-Rd-Rc, Rd-Ra-Rb-Rc, and Rb-Ra-Rb-Rc.

According to another preferred embodiment the present invention provides a substituted phenazine compound as defined above, wherein $R_1$ is selected from one or more of (xxiii) to (cviii)

(xxiii) Rd and Rb-Rc;
(xxiv) Rd and $Rd(Rc)_y$;
(xxv) Rd and Ra-Rd-Rc;
(xxvi) Rd and Ra-Rb-Rc;
(xxvii) Rd and Rd-Ra-Rd-Rc;
(xxviii) Rd and Rb-Ra-Rd-Rc;
(xxix) Rd and Rd-Ra-Rb-Rc;
(xxx) Rd and Rb-Ra-Rb-Rc;
(xxxi) Rd and $R_e(R_d—R_c)_2$;
(xxxii) Rd and $N(R_b—R_c)_3X$;
(xxxiii) Rd and $N(R_d—R_c)_3X$;
(xxxiv) Rd and $R_e(R_d—R_c)(R_b—R_c)$
(xxxv) Rd and $R_e(R_b—R_c)_2$
(xxxvi) Rb-Rc and $Rd(Rc)_y$;
(xxxvii) Rb-Rc and Ra-Rd-Rc;
(xxxviii) Rb-Rc and Ra-Rb-Rc;
(xxxix) Rb-Rc and Rd-Ra-Rd-Rc;
(xl) Rb-Rc and Rb-Ra-Rd-Rc;
(xli) Rb-Rc and Rd-Ra-Rb-Rc;
(xlii) Rb-Rc and Rb-Ra-Rb-Rc;
(xliii) Rb-Rc and $R_e(R_d—R_c)_2$;
(xliv) Rb-Rc and $N(R_b—R_c)_3X$;
(xlv) Rb-Rc and $N(R_d—R_c)_3X$;
(xlvi) Rb-Rc and $R_e(R_d—R_c)(R_b—R_c)$;
(xlvii) Rb-Rc and $R_e(R_b—R_c)_2$;
(xlviii) $Rd(Rc)_y$ and Ra-Rd-Rc;
(xlix) $Rd(Rc)_y$ and Ra-Rb-Rc;
(l) $Rd(Rc)_y$ and Rd-Ra-Rd-Rc;
(li) $Rd(Rc)_y$ and Rb-Ra-Rd-Rc;
(lii) $Rd(Rc)_y$ and Rd-Ra-Rb-Rc;
(liii) $Rd(Rc)_y$ and Rb-Ra-Rb-Rc;
(liv) $Rd(Rc)_y$ and $R_e(R_d—R_c)_2$;
(lv) $Rd(Rc)_y$ and $N(R_b—R_c)_3X$;
(lvi) $Rd(Rc)_y$ and $N(R_d—R_c)_3X$;
(lvii) $Rd(Rc)_y$ and $R_e(R_d—R_c)(R_b—R_c)$;
(lviii) $Rd(Rc)_y$ and $R_e(R_b—R_c)_2$;
(lix) Ra-Rd-Rc and Ra-Rb-Rc;
(lx) Ra-Rd-Rc and Rd-Ra-Rd-Rc;
(lxi) Ra-Rd-Rc and Rb-Ra-Rd-Rc;
(lxii) Ra-Rd-Rc and Rd-Ra-Rb-Rc;
(lxiii) Ra-Rd-Rc and Rb-Ra-Rb-Rc;
(lxiv) Ra-Rd-Rc and $R_e(R_d—R_c)_2$;
(lxv) Ra-Rd-Rc and $N(R_b—R_c)_3X$;
(lxvi) Ra-Rd-Rc and $N(R_d—R_c)_3X$;
(lxvii) Ra-Rd-Rc and $R_e(R_d—R_c)(R_b—R_c)$;
(lxviii) Ra-Rd-Rc and $R_e(R_b—R_c)_2$;
(lxix) Ra-Rb-Rc and Rd-Ra-Rd-Rc;
(lxx) Ra-Rb-Rc and Rb-Ra-Rd-Rc;
(lxxi) Ra-Rb-Rc and Rd-Ra-Rb-Rc;
(lxxii) Ra-Rb-Rc and Rb-Ra-Rb-Rc;
(lxxiii) Ra-Rb-Rc and $R_e(R_d—R_c)_2$;
(lxxiv) Ra-Rb-Rc and $N(R_b—R_c)_3X$;
(lxxv) Ra-Rb-Rc and $N(R_d—R_c)_3X$;
(lxxvi) Ra-Rb-Rc and $R_e(R_d—R_c)(R_b—R_c)$;
(lxxvii) Ra-Rb-Rc and $R_e(R_b—R_c)_2$;
(lxxviii)Rd-Ra-Rd-Rc and Rb-Ra-Rd-Rc;
(lxxix) Rd-Ra-Rd-Rc and Rd-Ra-Rb-Rc;
(lxxx) Rd-Ra-Rd-Rc and Rb-Ra-Rb-Rc;
(lxxxi) Rd-Ra-Rd-Rc and $R_e(R_d—R_c)_2$;
(lxxxii) Rd-Ra-Rd-Rc and $N(R_b—R_c)_3X$;
(lxxxii) Rd-Ra-Rd-Rc and $N(R_d—R_c)_3X$;
(lxxxiv) Rd-Ra-Rd-Rc and $R_e(R_d—R_c)(R_b—R_c)$ (lxxxv) Rd-Ra-Rd-Rc and $R_e(R_b—R_c)_2$
(lxxxvi) Rb-Ra-Rd-Rc and Rd-Ra-Rb-Rc;
(lxxxvii) Rb-Ra-Rd-Rc and Rb-Ra-Rb-Rc;
(lxxxviii) Rb-Ra-Rd-Rc and $R_e(R_d—R_c)_2$;
(lxxxix) Rb-Ra-Rd-Rc and $N(R_b—R_c)_3X$;
(xc) Rb-Ra-Rd-Rc and $N(R_d—R_c)_3X$;
(xci) Rb-Ra-Rd-Rc and $R_e(R_d—R_c)(R_b—R_c)$
(xcii) Rb-Ra-Rd-Rc and $R_e(R_b—R_c)_2$
(xciii) Rd-Ra-Rb-Rc and Rb-Ra-Rb-Rc,
(xciv) Rd-Ra-Rb-Rc and $R_e(R_d—R_c)_2$;
(xcv) Rd-Ra-Rb-Rc and $N(R_b—R_c)_3X$;
(xcvi) Rd-Ra-Rb-Rc and $N(R_d—R_c)_3X$;
(xcvii) Rd-Ra-Rb-Rc and $R_e(R_d—R_c)(R_b—R_c)$
(xcviii) Rd-Ra-Rb-Rc and $R_e(R_b—R_c)_2$
(xcix) $R_e(R_d—R_c)_2$ and $N(R_b—R_c)_3X$;
(c) $R_e(R_d—R_c)_2$ and $N(R_d—R_c)_3X$;
(ci) $R_e(R_d—R_c)_2$ and $R_e(R_d—R_c)(R_b—R_c)$;
(cii) $R_e(R_d—R_c)_2$ and $R_e(R_b—R_c)_2$,
(ciii) $N(R_b—R_c)_3X$ and $N(R_d—R_c)_3X$;
(civ) $N(R_b—R_c)_3X$ and $R_e(R_d—R_c)(R_b—R_c)$;
(cv) $N(R_b—R_c)_3X$ and $R_e(R_b—R_c)_2$;
(cvi) $N(R_d—R_c)_3X$ and $R_e(R_d—R_c)(R_b—R_c)$;
(cvii) $N(R_d—R_c)_3X$ and $R_e(R_b—R_c)_2$; or
(cviii) $R_e(R_d—R_c)(R_b—R_c)$ and $R_e(R_b—R_c)_2$;

in particular,

Rb-Rc and $Rd(Rc)_y$;
Rb-Rc and Ra-Rb-Rc;
Rb-Rc and Rb-Ra-Rd-Rc;
Rb-Rc and Rd-Ra-Rb-Rc;
Rb-Rc and Rb-Ra-Rb-Rc;
Rb-Rc and $R_e(R_d—R_c)_2$;
Rb-Rc and $N(R_b—R_c)_3X$;
Rb-Rc and $N(R_d—R_c)_3X$;
Rb-Rc and $R_e(R_d—R_c)(R_b—R_c)$;
Rb-Rc and $R_e(R_b—R_c)_2$;
$Rd(Rc)_y$ and Ra-Rb-Rc;
$Rd(Rc)_y$ and Rb-Ra-Rd-Rc;
$Rd(Rc)_y$ and Rd-Ra-Rb-Rc;
$Rd(Rc)_y$ and Rb-Ra-Rb-Rc;
$Rd(Rc)_y$ and $R_e(R_d—R_c)_2$;
$Rd(Rc)_y$ and $N(R_b—R_c)_3X$;
$Rd(Rc)_y$ and $N(R_d—R_c)_3X$;
$Rd(Rc)_y$ and $R_e(R_d—R_c)(R_b—R_c)$;
$Rd(Rc)_y$ and $R_e(R_b—R_c)_2$;
Ra-Rb-Rc and Rb-Ra-Rd-Rc;
Ra-Rb-Rc and Rd-Ra-Rb-Rc;
Ra-Rb-Rc and Rb-Ra-Rb-Rc;
Ra-Rb-Rc and $R_e(R_d—R_c)_2$;
Ra-Rb-Rc and $N(R_b—R_c)_3X$;
Ra-Rb-Rc and $N(R_d—R_c)_3X$;
Ra-Rb-Rc and $R_e(R_d—R_c)(R_b—R_c)$;
Ra-Rb-Rc and $R_e(R_b—R_c)_2$;
Rb-Ra-Rd-Rc and Rd-Ra-Rb-Rc;
Rb-Ra-Rd-Rc and Rb-Ra-Rb-Rc;
Rb-Ra-Rd-Rc and $R_e(R_d—R_c)_2$;
Rb-Ra-Rd-Rc and $N(R_b—R_c)_3X$;
Rb-Ra-Rd-Rc and $N(R_d—R_c)_3X$;
Rb-Ra-Rd-Rc and $R_e(R_d—R_c)(R_b—R_c)$;
Ra-Rb-Rc and $R_e(R_b—R_c)_2$;
Rd-Ra-Rb-Rc and Rb-Ra-Rb-Rc
Rd-Ra-Rb-Rc and $R_e(R_d—R_c)_2$;
Rd-Ra-Rb-Rc and $N(R_b—R_c)_3X$;
Rd-Ra-Rb-Rc and $N(R_d—R_c)_3X$;
Rd-Ra-Rb-Rc and $R_e(R_d—R_c)(R_b—R_c)$;
Rd-Ra-Rb-Rc and $R_e(R_b—R_c)_2$;
$R_e(R_d—R_c)_2$ and $N(R_b—R_c)_3X$;
$R_e(R_d—R_c)_2$ and $N(R_d—R_c)_3X$;
$R_e(R_d—R_c)_2$ and $R_e(R_d—R_c)(R_b—R_c)$;
$R_e(R_d—R_c)_2$ and $R_e(R_b—R_c)_2$;
$N(R_b—R_c)_3X$ and $N(R_d—R_c)_3X$;
$N(R_b—R_c)_3X$ and $R_e(R_d—R_c)(R_b—R_c)$;
$N(R_b—R_c)_3X$ and $R_e(R_b—R_c)_2$;
$N(R_d—R_c)_3X$ and $R_e(R_d—R_c)(R_b—R_c)$;
$N(R_d—R_c)_3X$ and $R_e(R_b—R_c)_2$; or
$R_e(R_d—R_c)(R_b—R_c)$ and $R_e(R_b—R_c)_2$.

According to another preferred embodiment the present invention provides a substituted phenazine compound as defined above, wherein $R_1$ is selected from one or more of (cviii) to (clxxxii)

(cviii) Rb-Rc, $Rd(Rc)_y$, and Ra-Rb-Rc;
(cix) Rb-Rc, $Rd(Rc)_y$, and Rb-Ra-Rd-Rc;
(cx) Rb-Rc, $Rd(Rc)_y$, and Rd-Ra-Rb-Rc;
(cxi) Rb-Rc, $Rd(Rc)_y$, and Rb-Ra-Rb-Rc;
(cxii) Rb-Rc, $Rd(Rc)_y$, and $R_e(R_d—R_c)_2$;
(cxiii) Rb-Rc, $Rd(Rc)_y$, and $N(R_b—R_c)_3X$;
(cxiv) Rb-Rc, $Rd(Rc)_y$, and $N(R_d—R_c)_3X$;
(cxv) Rb-Rc, $Rd(Rc)_y$, and $R_e(R_d—R_c)(R_b—R_c)$;
(cxvi) Rb-Rc, $Rd(Rc)_y$, and $R_e(R_b—R_c)_2$;
(cxvii) Rb-Rc, Ra-Rb-Rc, and Rb-Ra-Rd-Rc;
(cxviii) Rb-Rc, Ra-Rb-Rc and Rd-Ra-Rb-Rc;
(cxix) Rb-Rc, Ra-Rb-Rc and Rb-Ra-Rb-Rc;
(cxx) Rb-Rc, Ra-Rb-Rc and $R_e(R_d—R_c)_2$;
(cxxi) Rb-Rc, Ra-Rb-Rc and $N(R_b—R_c)_3X$;
(cxxii) Rb-Rc, Ra-Rb-Rc and $N(R_d—R_c)_3X$;
(cxxiii) Rb-Rc, Ra-Rb-Rc and $R_e(R_d—R_c)(R_b—R_c)$;
(cxxiv) Rb-Rc, Ra-Rb-Rc and $R_e(R_b—R_c)_2$;
(cxxv) Rb-Rc, Rb-Ra-Rd-Rc, and Rd-Ra-Rb-Rc;
(cxxvi) Rb-Rc, Rb-Ra-Rd-Rc, and Rb-Ra-Rb-Rc;
(cxxvii) Rb-Rc, Rb-Ra-Rd-Rc, and $R_e(R_d—R_c)_2$;
(cxxviii) Rb-Rc, Rb-Ra-Rd-Rc, and $N(R_b—R_c)_3X$;
(cxxix) Rb-Rc, Rb-Ra-Rd-Rc, and $N(R_d—R_c)_3X$;
(cxxx) Rb-Rc, Rb-Ra-Rd-Rc, and $R_e(R_d—R_c)(R_b—R_c)$;
(cxxxi) Rb-Rc, Rb-Ra-Rd-Rc, and $R_e(R_b—R_c)_2$;
(cxxxii) Rb-Rc, Rd-Ra-Rb-Rc, and Rb-Ra-Rb-Rc;
(cxxxiii) Rb-Rc, Rd-Ra-Rb-Rc, and $R_e(R_d—R_c)_2$;
(cxxxiv) Rb-Rc, Rd-Ra-Rb-Rc, and $N(R_b—R_c)_3X$;
(cxxxv) Rb-Rc, Rd-Ra-Rb-Rc, and $N(R_d—R_c)_3X$;
(cxxxvi) Rb-Rc, Rd-Ra-Rb-Rc, and $R_e(R_d—R_c)(R_b—R_c)$;
(cxxxvii) Rb-Rc, Rd-Ra-Rb-Rc, and $R_e(R_b—R_c)_2$;
(cxxxviii) $Rd(Rc)_y$, Ra-Rb-Rc, and Rb-Ra-Rd-Rc;
(cxxxix) $Rd(Rc)_y$, Ra-Rb-Rc, and Rd-Ra-Rb-Rc;
(cxl) $Rd(Rc)_y$, Ra-Rb-Rc, and Rb-Ra-Rd-Rc;
(cxli) $Rd(Rc)_y$, Ra-Rb-Rc, and $R_e(R_d—R_c)_2$;
(cxlii) $Rd(Rc)_y$, Ra-Rb-Rc, and $N(R_b—R_c)_3X$;
(cxliii) $Rd(Rc)_y$, Ra-Rb-Rc, and $N(R_d—R_c)_3X$;
(cxliv) $Rd(Rc)_y$, Ra-Rb-Rc, and $R_e(R_d—R_c)(R_b—R_c)$;
(cxlv) $Rd(Rc)_y$, Ra-Rb-Rc, and $R_e(R_b—R_c)_2$;
(cxlvi) $Rd(Rc)_y$ Rd-Ra-Rb-Rc, and Rb-Ra-Rb-Rc;
(cxlvii) $Rd(Rc)_y$ Rd-Ra-Rb-Rc, and $R_e(R_d—R_c)_2$;
(cxlviii) $Rd(Rc)_y$ Rd-Ra-Rb-Rc, and $N(R_b—R_c)_3X$;
(cxlix) $Rd(Rc)_y$ Rd-Ra-Rb-Rc, and $N(R_d—R_c)_3X$;
(cl) $Rd(Rc)_y$ Rd-Ra-Rb-Rc, and $R_e(R_d—R_c)(R_b—R_c)$;
(cli) $Rd(Rc)_y$ Rd-Ra-Rb-Rc, and $R_e(R_b—R_c)_2$;
(clii) $Rd(Rc)_y$, Rb-Ra-Rd-Rc, and Rd-Ra-Rb-Rc;
(cliii) $Rd(Rc)_y$, Rb-Ra-Rd-Rc, and Rb-Ra-Rb-Rc;
(cliv) $Rd(Rc)_y$, Rb-Ra-Rd-Rc, and $R_e(R_d—R_c)_2$;
(clv) $Rd(Rc)_y$, Rb-Ra-Rd-Rc, and $N(R_b—R_c)_3X$;
(clvi) $Rd(Rc)_y$, Rb-Ra-Rd-Rc, and $N(R_d—R_c)_3X$;
(clvii) $Rd(Rc)_y$, Rb-Ra-Rd-Rc, and $R_e(R_d—R_c)(R_b—R_c)$;
(clviii) $Rd(Rc)_y$, Rb-Ra-Rd-Rc, and $R_e(R_b—R_c)_2$;
(clix) Ra-Rb-Rc, Rb-Ra-Rd-Rc, and Rd-Ra-Rb-Rc;
(clx) Ra-Rb-Rc, Rb-Ra-Rd-Rc, and Rb-Ra-Rb-Rc;

(clxi) Ra-Rb-Rc, Rb-Ra-Rd-Rc, and Rb-Ra-Rb-Rc;
(clxii) Ra-Rb-Rc, Rb-Ra-Rd-Rc, and $R_e(R_d—R_c)_2$;
(clxiii) Ra-Rb-Rc, Rb-Ra-Rd-Rc, and $N(R_b—R_c)_3X$;
(clxiv) Ra-Rb-Rc, Rb-Ra-Rd-Rc, and $N(R_d—R_c)_3X$;
(clxv) Ra-Rb-Rc, Rb-Ra-Rd-Rc, and $R_e(R_d—R_c)(R_b—R_c)$;
(clxvi) Ra-Rb-Rc, Rb-Ra-Rd-Rc, and $R_e(R_b—R_c)_2$;
(clxvii) Rb-Ra-Rd-Rc, Rd-Ra-Rb-Rc, and Rb-Ra-Rb-Rc;
(clxviii) Rb-Ra-Rd-Rc, Rd-Ra-Rb-Rc and $R_e(R_d—R_c)_2$;
(clxix) Rb-Ra-Rd-Rc, Rd-Ra-Rb-Rc and $N(R_b—R_c)_3X$;
(clxx) Rb-Ra-Rd-Rc, Rd-Ra-Rb-Rc and $N(R_d—R_c)_3X$;
(clxxi) Rb-Ra-Rd-Rc, Rd-Ra-Rb-Rc and $R_e(R_d—R_c)(R_b—R_c)$;
(clxxii) Rb-Ra-Rd-Rc, Rd-Ra-Rb-Rc and $R_e(R_b—R_c)_2$;
(clxxiii) Rd-Ra-Rb-Rc, $R_e(R_d—R_c)_2$ and $N(R_b—R_c)_3X$;
(clxxiv) Rd-Ra-Rb-Rc, $R_e(R_d—R_c)_2$ and $N(R_d—R_c)_3X$;
(clxxv) Rd-Ra-Rb-Rc, $R_e(R_d—R_c)_2$ and $R_e(R_d—R_c)(R_b—R_c)$;
(clxxvi) Rd-Ra-Rb-Rc, $R_e(R_d—R_c)_2$ and $R_e(R_b—R_c)_2$;
(clxxvii) $R_e(R_d—R_c)_2$, $N(R_b—R_c)_3X$ and $N(R_d—R_c)_3X$;
(clxxviii) $R_e(R_d—R_c)_2$, $N(R_b—R_c)_3X$ and $R_e(R_d—R_c)(R_b—R_c)$;
(clxxix) $R_e(R_d—R_c)_2$, $N(R_b—R_c)_3X$ and $R_e(R_b—R_c)_2$;
(clxxx) $N(R_b—R_c)_3X$ and $N(R_d—R_c)_3X$ and $R_e(R_d—R_c)(R_b—R_c)$;
(clxxxi) $N(R_b—R_c)_3X$ and $N(R_d—R_c)_3X$ and $R_e(R_b—R_c)_2$; or
(clxxxii) $N(R_d—R_c)_3X$ and $R_e(R_d—R_c)(R_b—R_c)$ and $R_e(R_b—R_c)_2$.

According to another preferred embodiment the present invention provides a substituted phenazine compound as defined above,
wherein
$R_1$ is positioned at ring positions 7 or 8.

The integers p and m are typically defined to represent the number of substituents, i.e. the number of moieties other than —H, at the phenazine ring system characterizing the "substituted phenazine compound" as disclosed herein.

According to a further preferred embodiment the present invention provides a substituted phenazine compound as defined above,
wherein
p is 1 or 2 and, preferably, $R_2$ is positioned at ring positions 2 and/or 3.

According to another preferred embodiment the present invention provides a substituted phenazine compound as defined above,
wherein
m is 0 or 1 and, preferably, if m is 1, $R_3$ is positioned at ring positions 7 or 8.

According to a further preferred embodiment the present invention provides a substituted phenazine compound as defined above,
wherein
m is 1 and $R^3$ is positioned at ring positions 7 or 8,
$R_1$ is positioned at the other of ring positions 7 or 8; and
p is 2 and $R^2$ is positioned at ring positions 2 and 3.

According to another preferred embodiment the present invention provides a substituted phenazine compound as defined above,
wherein
m is 0;
$R_1$ is positioned at ring positions 7 or 8; and
p is 2 and $R^2$ is positioned at ring positions 2 and 3.

If $R_2$ and/or $R_3$ are $R_c$, $R_c$ can typically not be —H, as $R_2$ ($R_3$) needs to be a substituent, i.e. a moiety other than —H. Thus, $R_2$ is preferably one of —OH, —$SO_3H$, alkyl, in particular methyl, and C(═O)OH. Alternatively, $R_2$ is preferably one of —OH, —$SO_3H$, and C(═O)OH or one of —$SO_3H$, and C(═O)OH. $R_3$ is typically one of —OH and a member of the group as defined for $R_1$. Also, p and m are typically defined such that they refer to the number of moieties other than —H, i.e. to the number of substituents replacing —H at the phenazine ring system, thereby resulting in the "substituted phenazine compound" as disclosed herein.

Preferably, the substituted phenazine compound of the present invention may be characterized by m being 1 and $R_3$ being identical with $R_1$, wherein $R_1$ and $R_3$ may preferably be positioned at positions 7 and 8. Alternatively, p may preferably be 0, m may preferably be 1, and $R_1$ and $R_3$ may more preferably be identical.

According to one embodiment, the substituted phenazine compound is defined by $R_1$, wherein $R_1$ may be selected from the group consisting of —OH, —OR, —$NH_2$, —$NHR_x$, —$NR_xR_y$, and —N(H)C(═O)$R_x$, wherein $R_x$ and $R_y$ may be selected from an unsubstituted or a substituted $C_{1-4}$ alkyl, preferably an unsubstituted or a substituted $C_{1-3}$ alkyl, more preferably an unsubstituted or a substituted methyl or unsubstituted or a substituted ethyl. The substituent of the alkyl chain may preferably be selected from the group consisting of —C(═O)OH, ═O, —$SO_3H$, —OH, substituted or unsubstituted phenyl, and —$NH_2$. The substituent $R_1$ may preferably be positioned at ring position 7 or 8. $R_2$ and $R_3$ may be as disclosed herein. More specifically, $R_1$ may be selected from —OR, —$NHR_x$, —N(H)C(═O)$R_x$ and —$NR_xR_y$, with $R_x$ and $R_y$ as defined herein.

$R_x$ and $R_y$ may also represent a substituted or unsubstituted $C_{1-4}$ alkyl chain with one heteroatom replacing one carbon atom of its alkyl chain; the heteroatom may be selected from N, O and S. The substituents of the alkyl chain may be selected as defined above for $R_x$ and $R_y$.

According to a further embodiment, the substituted phenazine compound may be defined by $R_1$ being selected from the group consisting of —$OR_x$, —$NHR_x$, —$NR_xR_y$ and —N(H)C(═O)$R_x$, preferably —$OR_x$, —N(H)C(═O)$R_x$, and —$NR_xR_y$, more preferably —$OR_x$ and —$NR_xR_y$ wherein $R_x$ and $R_y$ are selected from an unsubstituted or a substituted $C_{1-4}$ alkyl. Preferably, $R_x$ and $R_y$ may be defined by an unsubstituted or a substituted $C_{1-3}$ alkyl, more preferably an unsubstituted or a substituted methyl or unsubstituted or a substituted ethyl. The substituent may preferably be selected from the group consisting of C(═O)OH, ═O, —$SO_3H$, —OH, substituted or unsubstituted phenyl, and —$NH_2$. Also, preferably, $R_1$ may be positioned at ring position 7 or 8. $R_2$ and $R_3$ may be selected as disclosed herein.

$R_2$ may be selected for substituted phenazine compound of the present invention from the group consisting of —H, —OH, —$SO_3H$, $C_{1-4}$ alkyl, in particular methyl, and —C(═O)OH. At least one $R_2$ may preferably be selected from —$SO_3H$ or —C(═O)OH, in particular —$SO_3H$, more preferably positioned at ring position 2 and/or 3.

$R_3$ may be selected from the group consisting of —H, —OH, a $C_{1-4}$ alkyl, preferably methyl, and a member of the group as disclosed herein for $R_1$ herein. More specifically, at least one or one $R_3$ is methyl or —OH. It is also disclosed that the phenazine compound may be characterized by a structure wherein at least one or, in particular one $R_3$ corresponds to the substituent as defined for $R_1$. Thereby, the phenazine compound may contain at least two identical substituents which are represented by $R_1$ and $R_3$. $R_3$ at ring position 7 or 8 may specifically be selected from —OH. $R_1$ at the other of ring positions 7 or 8 may be —OH as well or as defined for $R_1$ herein.

According to another embodiment, the substituted phenazine compound may be characterized by $R_1$ being selected from —$OR_x$, —$NH_2$, —$NHR_x$, and —$NR_xR_y$. $R_x$ and $R_y$ may be selected from an unsubstituted or a substituted $C_{1-4}$ alkyl, preferably an unsubstituted or a substituted $C_{1-3}$ alkyl, more preferably an unsubstituted or a substituted methyl or an unsubstituted or substituted ethyl. The substituent may be selected from the group consisting of —C(=O)OH, —$SO_3H$, —OH, =O, substituted or unsubstituted phenyl, and —$NH_2$. The phenazine ring substituent $R_1$ may be positioned at ring position 7 or 8. Thereby, p may be 1 or 2 and $R_2$ may be selected from methyl, —$SO_3H$ or —C(=O)OH, preferably —$SO_3H$. In case p being 1, the substituent may be positioned at ring position 2 or 3, in case p being 2, the substituents may be positioned at ring positions 2 and 3 or 1 and 3. $R_3$ may be selected from —OH or identical with $R_1$ and positioned at the other of ring positions 7 or 8, which is not substituted by $R_1$.

According to another embodiment, the substituted phenazine compound defines for $R_1$—$NR_xR_y$, wherein $R_x$ may be a substituted $C_{1-4}$alkyl, preferably methyl or ethyl. $R_y$ may be an unsubstituted $C_{1-4}$alkyl, preferably methyl. Alternatively, the embodiment defines $R_1$, preferably at ring position 7 or 8, as being selected from —OR, wherein $R_x$ may be a substituted $C_{1-4}$ alkyl, preferably a substituted ethyl or $C_3$ alkyl. $R_2$ and $R_3$ may be selected as disclosed herein.

Preferably, the substituted phenazine compound of the present invention may be characterized by one of the above defined substituents for $R_1$, which comprise $R_x$ or $R_y$, in particular $R_x$, wherein $R_x$ or $R_y$ may be a substituted $C_{1-4}$alkyl, wherein the substituent may be a terminal substituent. Alternatively or additionally, the $R_x$ or $R_y$, in particular $R_x$, may be chosen such that a substituted $C_{1-4}$alkyl may be characterized by a substituent being selected from —C(=O)OH and —$SO_3H$. According to another embodiment, the substituted phenazine compound is characterized such that $R_1$ may be —N(H)C(=O)$R_x$, wherein $R_x$ may preferably be selected from a substituted methyl or ethyl, in particular ethyl. The substituent may specifically be selected from —C(=O)OH and —$SO_3H$. It may also be foreseen that the substituent may preferably be a terminal substituent, i.e. a substituent located at the carbon atom of $R_x$ being most distant from the phenazine ring system. In particular, $R_1$ and $R_3$ may be identical such that $R_3$ represents the same substituent as $R_1$, e.g. located at ring positions 7 and 8. $R_2$ and $R_3$ may be selected as disclosed herein.

Preferably, the substituted phenazine compound of the present invention may exhibit for p 2, i.e. two $R_2$ are foreseen not being —H, wherein $R_2$ may be selected from —$SO_3H$ and methyl.

According to a further preferred embodiment the present invention provides a substituted phenazine compound as defined above, wherein $R_1$ is selected from the group consisting of —$N(CH_3)$—$CH_2$—C(=O)OH, —N—($CH_3$)—$(CH_2)_2$—C(=O)OH, —$N(CH_3)$—$CH_2$—$SO_3H$, —$N(CH_3)$—$(CH_2)_2$—$SO_3H$, —N(H)—$CH_2$-Aryl, in particular —N(H)—$CH_2$-Phenyl, —N(H)—$(CH_2)_2$-Aryl, in particular —N(H)—$(CH_2)_2$-Phenyl, —N(H)—$CH_2$—OH, —N(H)—$(CH_2)_2$—OH; —N(H)—$CH_3$, —N(H)—$C_2H_5$, —O—$CH_3$, —O—$C_2H_5$, —O—$CH_2$—$SO_3H$, —O—$(CH_2)_2$—$SO_3H$, —O—$(CH_2)_3$—$SO_3H$, —O—$CH_2$—CH(OH)—$CH_2$—$SO_3H$, —O—$CH_2$—CH(OH)—$CH_2$—OH, —O—$CH_2$—CH(OH)—$CH_2$—C(=O)OH, —N(H)C(=O)—$(CH_2)_2$—C(=O)OH, —N(H)C(=O)—$(CH_2)_2$—$SO_3H$, and —O—$CH_2$—CH(OH)—$CH_2$—$NH_3^+$.

According to another preferred embodiment the present invention provides a substituted phenazine compound as defined above, wherein $R_2$ is selected from the group consisting of —H, —OH, —$SO_3H$ and —C(=O)OH.

According to another preferred embodiment the present invention provides a substituted phenazine compound as defined above, wherein $R_3$ is selected from the group consisting of —H, —OH and a member selected from the group consisting of —$N(CH_3)$—$CH_2$—C(=O)OH, —N—($CH_3$)—$(CH_2)_2$—C(=O)OH, —$N(CH_3)$—$CH_2$—$SO_3H$, —$N(CH_3)$—$(CH_2)_2$—$SO_3H$, —N(H)—$CH_2$-Aryl, in particular —N(H)—$CH_2$-Phenyl, —N(H)—$(CH_2)_2$-Aryl, in particular —N(H)—$(CH_2)_2$-Phenyl, —N(H)—$CH_2$—OH, —N(H)—$(CH_2)_2$—OH; —N(H)—$CH_3$, —N(H)—$C_2H_5$, —O—$CH_3$, —O—$C_2H_5$, —O—$CH_2$—$SO_3H$, —O—$(CH_2)_2$—$SO_3H$, —O—$(CH_2)_3$—$SO_3H$, —O—$CH_2$—CH(OH)—$CH_2$—$SO_3H$, —O—$CH_2$—CH(OH)—$CH_2$—OH, —O—$CH_2$—CH(OH)—$CH_2$—C(=O)OH and —O—$CH_2$—CH(OH)—$CH_2$—$NH_3^+$.

According to a further preferred embodiment, the phenazine compounds are selected from the group consisting of 7,8-di hydroxy-3-methylphenazine-2-sulfonic acid, 7,8-dihydroxy-4-methylphenazine-2-sulfonic acid, 8-hydroxy-7-(methylamino)phenazine-2-sulfonic acid, 7-dimethylamino)-8-hydroxyphenazine-2-sulfonic acid, [(3-hydroxyphenazine-2-yl)(methyl)amino)]acetic acid, [(3-hydroxy-7-sulfophenazine-2-yl)(methyl)amino)]acetic acid, 2-[(3-hydroxy-1-methoxyphenazin-2-yl)(methyl)amino] ethane-1-sulfonic acid, 3-(benzylamino)phenazin-2-ol, 7-(benzylamino)-8-hydroxyphenazine-2-sulfonic acid, 7-[(2-hydroxyethyl)(methyl)amino]phenazine-2-sulfonic acid, 3-[(3-hydroxyphenazin-2-yl)oxy]propane-1-sulfonic acid, 3,3'-[phenazine-2,3-diylbis(oxy)]di(propane-1-sulfonic acid, 2-hydroxy-3-[(3-hydroxyphenazin-2-yl)oxy]-N,N,N-trimethylpropane-1-aminium, 7,9-dimethoxy-8-hydroxyphenazine-2-sulfonic acid, 7-methoxy-8-hydroxyphenazine-2-sulfonic acid, and 7,8-dihydroxyphenazine-2-formic acid. The above compounds are denoted according to IUPAC nomenclature. By using the alternative nomenclature (ring positions) as defined by Formulae (I)(a) and (I)(b), at least the substituent as defined by reference to position 7 of the phenazine core ring system is to be exchanged with position 8 (and vice versa) and to position 2 is to be exchanged with position 3 (and vice versa). Correspondingly, the substituent at position 9 becomes a substituent at position 6 of the phenazine core ring system according to the nomenclature defined by formulae (I)(a) and (I)(b).

More preferred phenazine compounds are selected from the group consisting of [(3-hydroxyphenazine-2-yl)(methyl) amino)]acetic acid, [(3-hydroxy-7-sulfophenazine yl)(methyl)amino)]acetic acid, 2-[(3-hydroxy-1-methoxyphenazin-2-yl)(methyl)amino]ethane-1-sulfonic acid, 3-(benzylamino)phenazin-2-ol, 7-(benzylamino)-8-hydroxyphenazine-2-sulfonic acid, 7-[(2-hydroxyethyl)(methyl)amino] phenazine-2-sulfonic acid, 3-[(3-hydroxyphenazin yl)oxy] propane-1-sulfonic acid, 3,3'-[phenazine-2,3-diylbis(oxy)]di (propane-1-sulfonic acid), 2-hydroxy-3-[(3-hydroxyphenazin-2-yl)oxy]-N,N,N-tri methyl propane-1-aminium, 7,9-dimethoxy-8-hydroxyphenazine-2-sulfonic acid, 7-methoxy-8-hydroxyphenazine-2-sulfonic acid, and 7,8-dihydroxyphenazine-2-formic acid. The above compounds are denoted according to IUPAC nomenclature. By using the alternative nomenclature (ring positions) as defined by Formulae (I)(a) and (I)(b), at least the substituent as defined by reference to position 7 of the phenazine ring system is to be exchanged with position 8 (and vice versa) and to position 2 is to be exchanged with position 3 (and vice versa).

More preferred phenazine compounds are selected from the group consisting of [(3-hydroxyphenazine-2-yl)(methyl)amino)]acetic acid, [(3-hydroxy-7-sulfophenazine-2-yl)(methyl)amino)]acetic acid, 2-[(3-hydroxy-1-methoxy-phenazin-2-yl)(methyl)amino]ethane-1-sulfonic acid, 3-(benzylamino)phenazin-2-ol, 7-(benzylamino)-8-hydroxyphenazine-2-sulfonic acid, 7-[(2-hydroxyethyl)(methyl)amino]phenazine-2-sulfonic acid, 2-hydroxy-3-[(3-hydroxyphenazin-2-yl)oxy]-N,N,N-trimethylpropane-1-aminium, 7,9-di methoxy-8-hydroxyphenazine-2-sulfonic acid, and 7-methoxy-8-hydroxyphenazine-2-sulfonic acid. The above compounds are denoted according to IUPAC nomenclature. By using the alternative nomenclature (ring positions) as defined by Formulae (I)(a) and (I)(b), at least the substituent definded by reference to position 7 (of the phenazine core ring system) is to be exchanged with position 8 (and vice versa) and to position 2 is to be exchanged with position 3 (and vice versa).

More preferred phenazine compounds are selected from the group consisting of [(3-hydroxyphenazine-2-yl)(methyl)amino)]acetic acid, [(3-hydroxy-7-sulfophenazine-2-yl)(methyl)amino)]acetic acid, 2-[(3-hydroxy-1-methoxy-phenazin-2-yl)(methyl)amino]ethane-1-sulfonic acid, 3-(benzylamino)phenazin-2-ol, 7-(benzylamino)-8-hydroxyphenazine-2-sulfonic acid, 7-[(2-hydroxyethyl)(methyl)amino]phenazine-2-sulfonic acid, and 2-hydroxy-3-[(3-hydroxyphenazin-2-yl)oxy]-N,N,N-tri methylpropane-1-aminium. The above compounds are denoted according to IUPAC nomenclature. By using the alternative nomenclature (ring positions) as defined by Formulae (I)(a) and (I)(b), at least the substituent with reference to position 7 is to be exchanged with position 8 (and vice versa) and to position 2 is to be exchanged with position 3 (and vice versa).

Preferred are also 3-[(3-hydroxyphenazin-2-yl)oxy]propane-1-sulfonic acid and/or 3,3'-[phenazine-2,3-diylbis(oxy)]di(propane-1-sulfonic acid. The above compounds are denoted according to IUPAC nomenclature. By using the alternative nomenclature (ring positions) as defined by Formulae (I)(a) and (I)(b), at least the substituent with reference to position 7 is to be exchanged with position 8 (and vice versa) and to position 2 is to be exchanged with position 3 (and vice versa).

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Unless denoted otherwise,

The term "alkyl" refers to the radical of saturated hydrocarbon groups, including linear (i.e. straight-chain) alkyl groups, branched-chain alkyl groups, cyclo-alkyl (alicyclic) groups, alkyl-substituted cyclo-alkyl groups, and cyclo-alkyl-substituted alkyl groups.

The term "linear or branched, saturated or unsaturated $C_1$-$C_8$ hydrocarbon group" relates to a linear or branched, saturated or unsaturated hydrocarbon group comprising 1, 2, 3, 4, 5, 6, 7, 8 or 9 carbon atoms. The term "linear or branched, saturated or unsaturated $C_1$-$C_5$ hydrocarbon group" relates to a linear or branched, saturated or unsaturated hydrocarbon group comprising 1, 2, 3, 4 or 5 carbon atoms.

Preferably, an alkyl group contains less than 30 carbon atoms, more preferably from 1 to 10 carbon atoms ("$C_{116}$, alkyl"), from 1 to 9 carbon atoms ("$C_{1-9}$ alkyl"), from 1 to 8 carbon atoms ("$C_{1-8}$ alkyl"), from 1 to 7 carbon atoms ("$C_{1-7}$ alkyl"), or from 1 to 6 carbon atoms ("$C_{1-6}$ alkyl"). In some embodiments, an alkyl group has 1 to 5 carbon atoms ("$C_{1-5}$ alkyl"). In some embodiments, an alkyl group may contain 1 to 4 carbon atoms ("$C_{1-4}$ alkyl"), from 1 to 3 carbon atoms ("$C_{1-3}$ alkyl"), or from 1 to 2 carbon atoms ("$C_{1-2}$ alkyl").

Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like.

Unless otherwise specified, each instance of an alkyl group is independently unsubstituted (an "unsubstituted alkyl") or substituted (a "substituted alkyl") with one or more substituents (e.g., halogen, such as F).

In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. Compounds described herein contemplates any and all such combinations in order to arrive at a stable compound. Heteroatoms such as nitrogen may have hydrogen substituents and/or any suitable substituent as described herein which satisfy the valencies of the heteroatoms and results in the formation of a stable moiety. Compounds described herein are not intended to be limited in any manner by the exemplary substituents described herein.

In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tent-butyl (tent-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

Exemplary substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety, or a $G^a$ group as defined herein.

Substituents may themselves be substituted. For instance, the substituents of a "substituted alkyl" may include both substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls may be further substituted with alkyls, alkenyls, alkoxys, alkylthios, aminoalkyls, carbonyl-substituted alkyls, —$CF_3$, —CN, and the like.

The term "haloalkyl" refers a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group as defined herein, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent hydrocarbon chain. Unless otherwise specified, each instance of a heteroalkyl group is independently unsubstituted (an "unsubstituted heteroalkyl") or substituted (a "substituted heteroalkyl") with one or more substituents as defined herein.

The term "carbocyclyl" or "carbocyclic" refers to a radical of a non-aromatic cyclic hydrocarbon group having preferably from 3 to 14 ring carbon atoms ("$C_{3-14}$ carbocyclyl") and zero heteroatoms in the non-aromatic ring system. Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents as defined herein.

The term "heterocyclyl" or "heterocyclic" refers to a radical of a preferably 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment may be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and may be saturated or may contain one or more carbon-carbon double or triple bonds. Heterocyclyl polycyclic ring systems may include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents as defined herein.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4] diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b] pyranyl, 5,7-dihydro-4H-thieno[2,3-c]pyranyl, 2,3-dihydro-1H-pyrrolo[2,3b]pyridinyl, 2,3-dihydrofuro[2,3-b] pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) preferably having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents as defined herein.

The term "heteroaryl" refers to a radical of a preferably 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment may be a carbon or nitrogen atom, as valency permits. Heteroaryl polycyclic ring systems may include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

A group is optionally substituted unless expressly provided otherwise. The term "optionally substituted" refers to a group which may be substituted or unsubstituted as defined herein.

The term "aliphatic group" refers to a straight-chain, branched-chain, or cyclic non-aromatic saturated or unsaturated hydrocarbon group and includes as alkyl groups, alkenyl groups, and alkynyl groups.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to group of formula —OR, wherein R is an alkyl group, as defined herein. Exemplary alkoxyl groups include methoxy, ethoxy, propyloxy, tert-butoxy and the like.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" refers to a group which contains a carbon atom connected with a double bond to an oxygen or a sulfur atom. Examples of moieties which contain a carbonyl include aldehydes, ketones, carboxylic acids, amides, esters, anhydrides, etc.

The term "ester" refers to groups or molecules which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "carbonyl" includes groups such as "alkylcarbonyl" groups where an alkyl group is covalently bound to a carbonyl group, "alkenylcarbonyl" groups where an alkenyl group is covalently bound to a carbonyl group, "alkynylcarbonyl" groups where an alkynyl group is covalently bound to a carbonyl group, "arylcarbonyl" groups where an aryl group is covalently attached to the carbonyl group. Furthermore, the term also refers to groups where one or more heteroatoms are covalently bonded to the carbonyl moiety. For example, the term includes moieties such as, for example, aminocarbonyl moieties, (where a nitrogen atom is bound to the carbon of the carbonyl group, e.g., an amide), aminocarbonyloxy moieties, where an oxygen and a nitrogen atom are both bond to the carbon of the carbonyl group (e.g., also referred to as a "carbamate"). Furthermore, aminocarbonylamino groups are also included as well as other combinations of carbonyl groups bound to heteroatoms (e.g., nitrogen, oxygen, sulfur, etc. as well as carbon atoms), such as thiocarbonyl, thiocarboxylic acid and thiolformate. Furthermore, the heteroatom can be further substituted with one or more alkyl, alkenyl, alkynyl, aryl, aralkyl, acyl, etc. moieties.

The term "ether" refers to groups or molecules which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "thioether" refers to groups or molecules which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties where an alkyl, alkenyl, or alkynyl group is bonded to a sulfur atom which is covalently bonded to an alkynyl group.

The term "amine" or "amino" includes compounds where a nitrogen atom is covalently bonded to at least one carbon atom or heteroatom. The term "alkyl amino" includes groups and compounds where the nitrogen is bound to at least one additional alkyl group. The term "dialkyl amino" includes groups where the nitrogen atom is bound to at least two additional alkyl groups. The term "arylamino" and "diarylamino" include groups where the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amine" or "amino" in particular refers to a —$NH_2$ group, preferably including any of its protonation states, such as —$NH_3^+$.

The term "amide" or "aminocarboxy" includes compounds or moieties which contain a nitrogen atom which is bound to the carbon atom of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties where alkyl, alkenyl, alkynyl and aryl moieties, respectively, are bound to a nitrogen atom which is in turn bound to the carbon of a carbonyl group.

The term "nitro" refers to a —$NO_2$ group.

The term "halo" or "halogen" refers to fluorine (fluoro, —F), chlorine (chloro, —Cl), bromine (bromo, —Br), or iodine (iodo, —I) groups.

The term "thiol" or "sulfhydryl" refers to a —SH group.

The term "hydroxyl" refers to a —OH group, preferably including all of its protonation states, such as —$O^+$.

The term "sulfonyl" refers to a —$SO_3H$ group, preferably including all of its protonation states, such as —$SO_3$.

The term "phosphoryl" refers to a —$PO_3H_2$ group, preferably including all of its protonation states, such as —$PO_3H^-$ and —$PO_3^{2-}$.

The term "phosphonyl" refers to a —$PO_3R_2$ group, wherein each R is H or alkyl, provided that at least one R is alkyl, as defined herein, preferably including all of its protonation states, such as —$PO_3R^-$.

The term "oxo" refers to a =O group.

The term "carboxyl" refers to a —COOH group, preferably including all of its protonation states, such as —COO—.

The term "oxy" refers to a —O group.

The term "quinone" refers to a class of cyclic organic compounds that include fully conjugated —C(=O)— groups and carbon-carbon double bonds. In one example, the term "quinone" refers to organic compounds that are formally derived from aromatic compounds by replacement of an even number of —CH= groups with —C(=O)— groups with the double bonds rearranged as necessary to provide a fully conjugated cyclic dione, tetra-one, or hexa-one structure. The term inter alia covers substituted and unsubstituted quinones derived from mono-, di- and trihydroaromatic systems comprising 1 to 3 fused carbon cyclic rings in both their oxidized ("quinone") and reduced ("hydroquinone") forms.

The term "conjugated" when referring to two functional groups (having a double bond) means that the two groups are part of a connected system of p-orbital delocalized electrons with alternating single and multiple bonds. The two groups also include a degree of unsaturation. For example, conjugated groups may include multiple double bonds or aromatic groups (e.g., phenyl) between the groups. Moreover, if the two groups adjacent, the groups are also conjugated.

The term "standard electrode potential" means the electrical potential (i.e., the voltage developed) of a reversible electrode at standard state in which solutes are at an effective concentration of 1 mol/liter, the activity for each pure solid, pure liquid, or for water (solvent) is 1, the pressure of each gaseous reagent is 1 atm., and the temperature is 25° C. Standard electrode potentials are reduction potentials.

Redox Active Compounds and Compositions

The present invention provides the above-described novel phenazine compounds and compositions comprising the same. Said compounds and compositions are preferably redox active. Preferably, the term "redox active" refers to the capability of a compound (or a composition comprising the same) to participate in a redox reaction. Such "redox active" compounds typically have energetically accessible levels that allow redox reactions to alter their charge state, whereby electrons are either removed (oxidation—yielding an oxidized form of the compound) from atoms of the compound being oxidized or transferred to the compound being reduced (reduction—yielding a reduced from of the compound). A "redox active" compound may thus be understood as a chemical compound, which may form a pair of an oxidizing and a reducing agent, i.e. a redox pair. The redox pair of the phenazine compounds according to the invention is depicted by formula (I)'s "oxidized" and "reduced" state. Accordingly, the present invention may typically provide a composition as defined above, comprising at least one compound according to Formula (I)(b) (reduced state) and/or at least one corresponding compound of Formula (I)(a) (oxidized state).

The term "redox active species" preferably relates to a compound or component that is capable of forming redox pairs having different oxidation and reduction states. In a redox flow battery an electrochemically active component refers to the chemical species that participate in the redox reduction during the charge and discharge process.

The present invention further provides a composition comprising at least one or at least two substituted phenazine compounds as described above as redox active species and a solvent.

According to a preferred embodiment the present invention provides a composition as defined above, wherein the composition comprises as a solvent water and/or an organic water-miscible (co)solvent, e.g. by defining a solvent of a vol % of at least 70, 80, 90 or 95 vol % water content and the remainder being the organic water-miscible solvent. The organic water-miscible (co)solvent may be selected from ethanol, DMSO, methanol, 1,4-dioxane, tetrahydrofurane, an ether (e.g. ethylene glycol dimethylether, diethylene glycol dimethylether and/or triethylene glycol dimethylether), fat alcohol ethoxylates having a C12 to C18 hydrocarbon chain and a degree of ethoxylation of between 2 to 30, acetonitrile, anisol, acetone and/or glycol (e.g. ethylene glycol, diethylene glycol and/or triethylene glycol) etc. It may also be foreseen two combine more than one, e.g. two organic water-miscible (co)solvents with water as the basic solvent. Preferred as organic co-solvents are monoalcohols according to formula HO—$R^3$, wherein R3 is a saturated or partially unsaturated linear or branched C1 to C5 hydrocarbon chain, DMSO, ethylene glycol and/or glycerin. Preferably, the solvent is water without any organic (co)solvent.

According to a further preferred embodiment the present invention provides a substituted phenazine compound as defined above, wherein the composition has a pH value from 6 to 13.5, preferably from 8 to 12.5, more preferably from 9 to 12, e.g. from 11 to 12.

According to another preferred embodiment the present invention provides a composition as defined above, wherein the composition contains from 0.2 to 3 M, preferably from 0.35 to 2 M, more preferably from 0.5 to 1.5 M of at least one substituted phenazine compound. Accordingly, one or more phenazine compounds as defined by formula (I) may be present in the composition in their reduced and/or oxidized state, e.g. 2 to 5 different phenazine compounds.

As mentioned, the present invention relates to a composition, preferably an aqueous composition, comprising or (essentially) consisting of the inventive phenazine compounds as defined herein. The compositions may comprise or (essentially) consist of at least 1, or a plurality of at least 2, 3, 4, 5 or more of the inventive compounds as defined herein. Unless denoted otherwise, e.g. "two" of the inventive compounds comprised by an inventive composition may represent the oxidized and the reduced from of the (structurally otherwise identical) inventive compound or may represent two structurally distinct inventive compounds.

A composition "comprising" the inventive compounds as defined herein may comprise, in addition to the at least 1, or a plurality of at least 2, 3, 4, 5 or more of the inventive compounds any suitable additive, e.g. solvents, stabilizers, or the like.

A composition "essentially consisting of" the inventive compounds as defined herein may comprise at least 1, or a plurality of at least 2, 3, 4, 5 or more of the inventive compounds with a minor amount of by-products, impurities or contaminants, preferably in an amount of less than 10%, more preferably less than 5% the overall composition by dry content mass. Said by-products, impurities or contaminants are not compounds as defined herein.

A composition "consisting of" the inventive compounds as defined herein may consist of at least 1, or a plurality of at least 2, 3, 4, 5 or more of the inventive compounds and does not comprise any additives, by-products, impurities or contaminants as defined above. It may be preferred that a composition "consisting of" the inventive compounds is composed exclusively from a plurality of at least 2, 3, 4, 5 or more of the inventive compounds.

It may be preferred that the compositions according to the invention exhibit a purity of 100%. Put differently, it may be preferred that the compositions according to the invention do not contain any by-products, impurities or contaminants. Such compositions may be particularly useful as redox flow battery electrolytes when before the onset of the battery operation.

According to a preferred embodiment, the present invention relates to the use of a phenazine compound according to the present invention as a redox active species, preferably as a negolyte, or the use of a composition according to the present invention as a battery electrolyte, preferably as a negolyte, more preferably as redox flow battery electrolyte or, preferably, redox flow battery negolyte.

In a further aspect, the present invention provides compositions as described above comprising at least one phenazine compound according to the present invention as described above and at least one further organic compound other than the phenazine compounds according to formula (I) above, which are characterized by any one of General Formulae (1)-(6) or salts thereof:

General Formula (1):

(a)

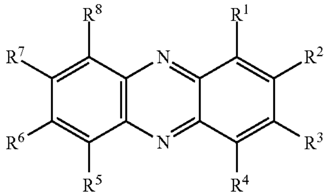

(b)

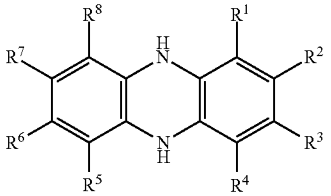

General Formula (2):

(a)

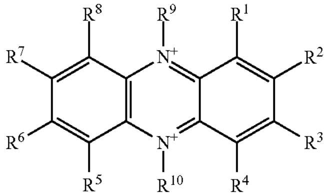

(b)

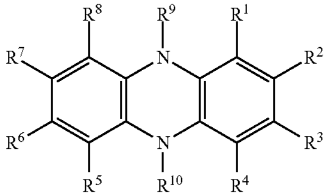

General Formula (3):

(a)

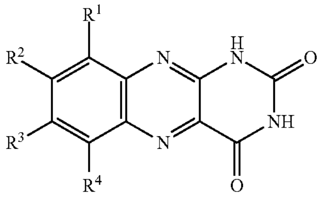

(b)

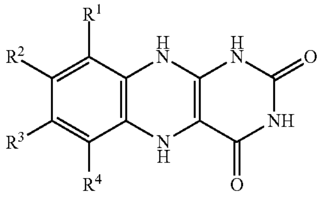

General Formula (4):

(a)

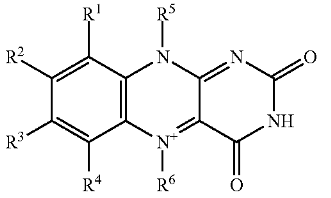

-continued (b)

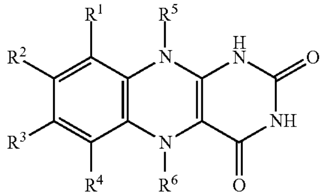

General Formula (5):

(a)

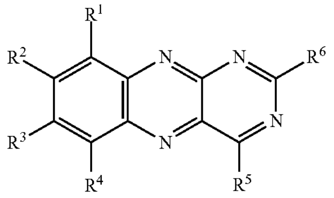

(b)

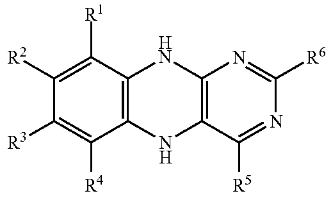

General Formula (6):

(a)

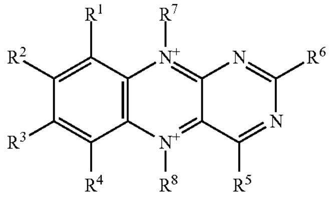

(b)

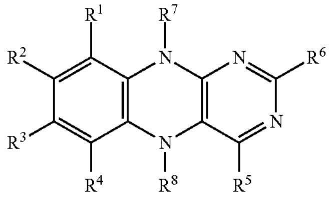

wherein, each $R^1$-$R^8$ in General Formula (1),
each $R^1$-$R^{10}$ in General Formula (2),
each $R^1$-$R^4$ in General Formula (3),
each $R^1$-$R^6$ in General Formula (4),
each $R^1$-$R^6$ in General Formula (5), and
each $R^1$-$R^8$ in General Formula (6)

is independently selected from —H, -Alkyl, -Alkyl$G^a$, -Aryl, —$SO_3H$, —$SO_3^-$, —$PO_3H_2$, —OH, —$OG^a$, —SH, -Amine, —$NH_2$, —CHO, —COOH, —$COOG^a$, —CN, —$CONH_2$, —$CONHG^a$, —$CONG^{a2}$, -Heteroaryl, -Heterocycyl, —$NOG^a$, —$N^+OG^a$, —F, —Cl, and —Br, or are joined together to form a saturated or unsaturated carbocycle;

wherein each $G^a$ is independently selected from

—H, -Alkyl, -Alkyl$G^b$, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —$NHG^b$, —$NG^b_2$, -$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+OAlkyl$, —F, —Cl, and —Br;

wherein each $G^b$ is independently selected from

—H, -Alkyl, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —CHO, —COOH, —COOAlkyl, —CN, —$CONH_2$, —CONHAlkyl, —$CONAlkyl_2$, -Heteroaryl, -Heterocycyl, —$N^+OAlkyl$, —F, —Cl, and —Br.

Preferably, each $R^1$-$R^8$ in General Formula (1), each $R^1$-$R^{10}$ in General Formula (2), each $R^1$-$R^4$ in General Formula (3), each $R^1$-$R^6$ in General Formula (4), each $R^1$-$R^6$ in General Formula (5), and each $R^1$-$R^8$ in General Formula (6)

may be independently selected from —H, -Alkyl, -$AlkylG^a$, —$SO_3H$, —$SO_3$, —$OG^a$, and —COOH, wherein each $G^a$ is independently selected from —H, -Alkyl, -$AlkylG^b$, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —$NHG^b$, —$NG^b_2$, -$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+OAlkyl$, —F, —Cl, and —Br;

wherein each $G^b$ is independently selected from

—H, -Alkyl, -Aryl, —$SO_3H$, —$SO_3$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —CHO, —COOH, —COOAlkyl, —CN, —$CONH_2$, —CONHAlkyl, —$CONAlkyl_2$, -Heteroaryl, -Heterocycyl, —$N^+OAlkyl$, —F, —Cl, and -Br.

Alternatively,

"alkyl" is selected from linear, branched or cyclic —$C_nH_{2n-o}$ and —$C_nH_{2n-o-m}G^a{}_m$;

"aryl" is selected from —$C_6H_5$, —$C_{10}H_7$, —$C_{13}H_8$, —$C_{14}H_9$, —$C_6H_{5-m}G^a{}_m$, —$C_{10}H_{7-m}G^a{}_m$, —$C_{13}H_{8-m}G^a{}_m$, —$C_{14}H_{9-m}G^a{}_m$;

"heteroaryl" is selected from —$C_{5-p}N_pH_{5-p-q}G^a{}_q$, —$C_{6-p}N_pH_{5-p-q}G^a{}_q$, —$C_{7-p}N_pH_{7-p-q}G^a{}_q$, —$C_{8-p}N_pH_{6-p-q}G^a{}_q$, —$C_{9-p}N_pH_{7-p-q}G^a{}_q$, —$C_{10-p}N_pH_{7-p-q}G^a{}_q$, —$C_4OH_{3-q}G^a{}_q$, —$C_6OH_{5-q}G^a{}_q$, —$C_7OH_{4-q}G^a{}_q$, —$C_6O_2H_{3-q}G^a{}_q$, —$C_8OH_{5-q}G^a{}_q$, —$C_4SH_{3-q}G^a{}_q$, —$C_6SH_{5-q}G^a{}_q$, —$C_7SH_{4-q}G^a{}_q$, —$C_6S_2H_{3-q}G^a{}_q$, —$C_8SH_{5-q}G^a{}_q$, —$C_3ON_pH_{3-p-q}G^a{}_q$, —$C_6ON_pH_{5-pq}G^a{}_q$, —$C_7ON_pH_{4-p-q}G^a{}_q$, —$C_6O_2N_pH_{3-p-q}G^a{}_q$, —$C_8ON_pH_{5-p-q}G^a{}_q$, —$C_3SN_pH_{3-p-q}G^a{}_q$, —$C_6SN_pH_{5-p-q}G^a{}_q$, —$C_7SN_pH_{4-p-q}G^a{}_q$, —$C_6S_2N_pH_{3-p-q}G^a{}_q$, —$C_6OSN_pH_{3-p-q}G^a{}_q$, —$C_8SN_pH_{5-p-q}G^a{}_q$, —$C_{8-p}N_p{}^+H_{6-p-q}G^a{}_q$, —$C_{6-p}N_p{}^+H_{6-p-q}G^a{}_q$, —$C_{7-p}N_p{}^+H_{8-p-q}G^a{}_q$, —$C_{8-p}N_p{}^+H_{7-p-q}G^a{}_q$, —$C_{9-p}N_p{}^+H_{8-p-q}G^a{}_q$, —$C_{10-p}N_p{}^+H_{8-p-q}G^a{}_q$, —$C_3ON_p{}^+H_{4-p-q}G^a{}_q$, —$C_6ON_p{}^+H_{6-p-q}G^a{}_q$, —$C_7ON_p{}^+H_{5-p-q}G^a{}_q$, —$C_6O_2N_p{}^+H_{4-p-q}G^a{}_q$, —$CON_p{}^+H_{6-p-q}G^a{}_q$, —$C_3SN_p{}^+H_{4-p-q}G^a{}_q$, —$C_6SN_p{}^+H_{6-p-q}G^a{}_q$, —$C_7SN_p{}^+H_{5-p-q}G^a{}_q$, —$C_6S_2N_p{}^+H_{4-p-q}G^a{}_q$, —$C_6OSN_p{}^+H_{4-p-q}G^a{}_q$, —$C_8SN_p{}^+H_{6-p-q}G^a{}_q$, "heterocyclyl" is selected from —$C_{5-p}N_pH_{8-o-p-q}G^a{}_q$, —$C_{6-p}N_pH_{10-o-p-q}G_q$, —$C_{7-p}N_pH_{12-o-p-q}G^a{}_q$, —$C_{8-p}N_pH_{14-o-p-q}G^a{}_q$, —$C_{9-p}N_pH_{16-o-p-q}G^a{}_q$, —$C_{10-p}N_pH_{18-o-p-q}G^a{}_q$, —$C_{5-p}O_pH_{8-o-2p-q}G^a{}_q$, —$C_{6-p}O_pH_{10-o-2p-q}G^a{}_q$, —$C_{7-p}O_pH_{12-o-2p-q}G^a{}_q$, —$C_{8-p}O_pH_{14-o-2p-q}G^a{}_q$, —$C_{9-p}O_pH_{16-o-2p-q}G^a{}_q$, —$C_{10-p}O_pH_{18-o-2p-q}G^a{}_q$, —$C_{5-p}S_pH_{8-o-2p-q}G^a{}_q$, —$C_{6-p}S_pH_{10-o-2p-q}G^a{}_q$, —$C_{7-p}S_pH_{12-o-2p-q}G^a{}_q$, —$C_{8-p}S_pH_{14-o-2p-q}G^a{}_q$, —$C_{9-p}S_pH_{16-o-2p-q}G^a{}_q$, —$C_{10-p}S_pH_{18-o-2p-q}G^a{}_q$, —$C_{5-p}O_lN_pH_{8-o-p-2l-q}G^a{}_q$, —$C_{6-p}O_lN_pH_{10-o-p-2l-q}G^a{}_q$, —$C_{7-p}O_lN_pH_{12-o-p-2l-q}G^a{}_q$, —$C_{8-p}O_lN_pH_{14-o-p-2l-q}G^a{}_q$, —$C_{9-p}O_lN_pH_{16-o-p-2l-q}G^a{}_q$, —$C_{10-p}O_lN_pH_{18-o-p-2l-q}G^a{}_q$, —$C_{5-p}S_lN_pH_{8-o-p-2l-q}G^a{}_q$, —$C_{6-p}S_lN_pH_{10-o-p-2l-q}G^a{}_q$, —$C_{7-p}S_lN_pH_{12-o-p-2l-q}G^a{}_q$, —$C_{8-p}S_lN_pH_{14-o-p-2l-q}G^a{}_q$, —$C_{9-p}S_lN_pH_{16-o-p-2l-q}G^a{}_q$, —$C_{10-p}S_lN_pH_{18-o-p-2l-q}G^a{}_q$; and/or "amine" is selected from —$C_sH_{2s}$—$NH_2$, —$C_sH_{2s}$—$NHG^a$, —$C_nH_{2s}$-$NG^a{}_2$, —$C_sH_{2s}$—$NG^a{}_3{}^+$, wherein l=1, 2, 3, 4, n=1, 2, 3, 4, 5, 6, 7, 8, 9, 10, more preferably n=1, 2, 3, 4, 5, 6, most preferably n=1, 2, 3 or 4, m=1, 2, 3, 4, 5, 6, 7, 8, 9, 10, more preferably m=1, 2, 3, 4, most preferably m=1 or 2, o=1, 2, 3, 5, 7, 9, p=1, 2, 3, 4, 5, 6, more preferably p=3, 4, 5 or 6, q=1, 2, 3, 4, 5, more preferably q=1, 2 or 3, s=1, 2, 3, 4, 5 or 6;

wherein $G^a$ is independently selected from

—H, -Alkyl, -Aryl, —$SO_3H$, —$SO_3^-$, —$PO_3H_2$, —OH, —OAlkyl, —OOH, —OOAlkyl, —SH, -SAlkyl, —$NH_2$, —NHAlkyl, —$NAlkyl_2$, —$NAlkyl_3^+$, —$NHG^b$, -$NG^b_2$, -$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+OAlkyl$, —F, —Cl, and —Br;

wherein each $G^b$ is independently selected from

—H, -Alkyl, -Aryl, —$SO_3H$, —$SO_3^-$, —$PO_3H_2$, —OH, —OAlkyl, —OOH, —OOAlkyl, —SH, -SAlkyl, —$NH_2$, —NHAlkyl, —$NAlkyl_2$, —$NAlkyl_3^+$, —CHO, —COOH, —COOAlkyl, —CN, —$CONH_2$, —CONHAlkyl, —$CONAlkyl_2$, -Heteroaryl, -Heterocycyl, —$N^+OAlkyl$, —F, —Cl, and -Br.

In some embodiments, each $R^1$-$R^8$ in General Formula (1), each $R^1$-$R^{10}$ in General Formula (2), each $R^1$-$R^4$ in General Formula (3), each $R^1$-$R^6$ in General Formula (4), each $R^1$-$R^6$ in General Formula (5), and each $R^1$-$R^8$ in General Formula (6) is each independently not selected from —SH, —$NOG^a$ and —$N^+OG^a$.

In some embodiments, each $G^a$ in any one of General Formulae (1)-(6) is each independently not selected from —OOH, —OOAlkyl, —SH, —$NOG^b$ and —$N^+OAlkyl$, wherein $G^b$ is as defined above.

In some embodiments, each $G^b$ in any one of General Formulae (1)-(6) is each independently not selected from —OOH, —OOAlkyl, —SH, and —$N^+OAlkyl$.

The compounds according to General Formula (1) may preferably be generally classified as "phenazines". The compounds according to General Formula (2) may preferably be classified as "N-substituted phenazines". The compounds according to General Formula (3) may preferably be classified as "alloxazines". The compounds according to General Formula (4) may preferably be classified as "N-substituted alloxazines". The compounds according to General Formula (5) may preferably be classified as "benzopteridines". The compounds according to General Formula (6) may preferably be classified as "N-substituted benzopteridines".

Particularly preferred compounds may be characterized by General Formula (1), (3) or (4) as defined above.

The compounds of General formulae (1) to (6) are preferably substituted and include one or more substituents as described herein below. The presence of certain substituents may, e.g., improve the solubility, electrochemical properties and/or stability of the inventive compounds.

The compounds may include at least one substituent selected from:

—H, -Alkyl, -$AlkylG^a$, -Aryl, —$SO_3H$, —$SO_3^-$, —$PO_3H_2$, —OH, —$OG^a$, —SH, -Amine, —$NH_2$, —CHO, —COOH, —$COOG^a$, —CN, —$CONH_2$, —$CONHG^a$, —$CONG^a{}_2$, -Heteroaryl, -Heterocycyl, —$NOG^a$, —$N^+OG^a$, —F, —Cl, and —Br, or may be joined together to form a saturated or unsaturated carbocycle;

wherein each $G^a$ is independently selected from

—H, -Alkyl, -Alkyl$G^b$, -Aryl, —$SO_3H$, —$SO_3^-$, —$PO_3H_2$, —OH, —OAlkyl, —OOH, —OOAlkyl, —SH, -SAlkyl, —$NH_2$, —NHAlkyl, —$NAlkyl_2$, —$NAlkyl_3$, —$NHG^b$, -$NG^b_2$, —$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+$OAlkyl, —F, —Cl, and —Br;

wherein each $G^b$ is independently selected from

—H, -Alkyl, -Aryl, —$SO_3H$, —$SO_3^-$, —$PO_3H_2$, —OH, —OAlkyl, —OOH, —OOAlkyl, —SH, -SAlkyl, —$NH_2$, —NHAlkyl, —$NAlkyl_2$, —$NAlkyl_3{}^+$, —CHO, —COOH, —COOAlkyl, —CN, —$CONH_2$, —CONHAlkyl, —CON-$Alkyl_2$, -Heteroaryl, -Heterocycyl, —$N^+$OAlkyl, —F, —Cl, and -Br.

More preferably, the compounds may include at least one substituent selected from —H, -Alkyl, -Alkyl$G^a$, —$SO_3H$/—$SO_3$, —$OG^a$, and —COOH, wherein each $G^a$ is independently selected from —H, -Alkyl, -Alkyl$G^b$, -Aryl, —$SO_3H$, —$SO_3^-$, —$PO_3H_2$, —OH, —OAlkyl, —OOH, —OOAlkyl, —SH, -SAlkyl, —$NH_2$, —NHAlkyl, —$NAlkyl_2$, —$NAlkyl_3{}^+$, —$NHG^b$, -$NG^b_2$, —$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+$OAlkyl, —F, —Cl, and —Br;

wherein each $G^b$ is independently selected from

—H, -Alkyl, -Aryl, —$SO_3H$, —$SO_3^-$, —$PO_3H_2$, —OH, —OAlkyl, —OOH, —OOAlkyl, —SH, -SAlkyl, —$NH_2$, —NHAlkyl, —$NAlkyl_2$, —$NAlkyl_3{}^+$, —CHO, —COOH, —COOAlkyl, —CN, —$CONH_2$, —CONHAlkyl, —CON-$Alkyl_2$, -Heteroaryl, -Heterocycyl, —$N^+$OAlkyl, —F, —Cl, and -Br.

In some embodiments, the substituents may each independently not be —SH, —$NOG^a$ and —$N^+OG^a$, wherein $G^a$ is as defined above. In some embodiments, in the above substituent definitions, each $G^a$ is independently not selected from —OOH, —OOAlkyl, —SH, —$NOG^b$ and —$N^+$OAlkyl, wherein $G^b$ is as defined above. In some embodiments, in the above substituent definitions, each $G^b$ is independently not selected from —OOH, —OOAlkyl, —SH, and —$N^+$OAlkyl.

Preferably, "alkyl", "aryl", "heteroaryl", "heterocyclyl" and "amine" are as defined above.

Alternatively,

"alkyl" may be selected from linear, branched or cyclic —$C_nH_{2n-o}$ and —$C_nH_{2n-o-m}G^a_m$;

"aryl" may be selected from —$C_6H_5$, —$C_{10}H_7$, —$C_{13}H_8$, —$C_{14}H_9$, —$C_6H_{5-m}G^a_m$, —$C_{10}H_{7-m}G^a_m$, —$C_{13}H_{8-m}G^a_m$, —$C_{14}H_{9-m}G^a_m$;

"heteroaryl" may be selected from —$C_{5-p}N_pH_{5-p-q}G^a_q$, —$C_{6-p}N_pH_{5-p-q}G^a_q$, —$C_{7-p}N_pH_{7-p-q}G^a_q$, —$C_{8-p}N_pH_{6-p-q}G^a_q$, —$C_{9-p}N_pH_{7-p-q}G^a_q$, —$C_{10-p}N_pH_{7-p-q}G^a_q$, —$C_4OH_{3-q}G^a_q$, —$C_6OH_{5-q}G^a_q$, —$C_7OH_{4-q}G^a_q$, —$C_6O_2H_{3-q}G^a_q$, —$C_8OH_{5-q}G^a_q$, —$C_4SH_{3-q}G^a_q$, —$C_6SH_{5-q}G^a_q$, —$C_7SH_{4-q}G^a_q$, —$C_6S_2H_{3-q}G^a_q$, —$C_8SH_{5-q}G^a_q$, —$C_3ON_pH_{3-p-q}G^a_q$, —$C_6ON_pH_{5-p-q}G^a_q$, —$C_7ON_pH_{4-p-q}G^a_q$, —$C_6O_2N_pH_{3-p-q}G^a_q$, —$C_8ON_pH_{5-p-q}G^a_q$, —$C_3SN_pH_{3-p-q}G^a_q$, —$C_6SN_pH_{5-p-q}G^a_q$, —$C_7SN_pH_{4-p-q}G^a_q$, —$C_6S_2N_pH_{3-p-q}G^a_q$, —$C_6OSN_pH_{3-p-q}G^a_q$, —$C_8SN_pH_{5-p-q}G^a_q$, —$C_{5-p}N_p{}^+H_{6-p-q}G^a_q$, —$C_{6-p}N_p{}^+H_{6-p-q}G^a_q$, —$C_{7-p}N_p{}^+H_{8-p-q}G^a_q$, —$C_{8-p}N_p{}^+H_{7-p-q}G^a_q$, —$C_{9-p}N_p{}^+H_{8-p-q}G^a_q$, —$C_{10-p}N_p{}^+H_{8-p-q}G^a_q$, —$C_3ON_p{}^+H_{4-p-q}G^a_q$, —$C_6ON_p{}^+H_{6-p-q}G^a_q$, —$C_7ON_p{}^+H_{5-p-q}G^a_q$, —$C_6O_2N_p{}^+H_{4-p-q}G^a_q$, —$CON_p{}^+H_{6-p-q}G^a_q$, —$C_3SN_p{}^+H_{4-p-q}G^a_q$, —$C_6SN_p{}^+H_{6-p-q}G^a_q$, —$C_7SN_p{}^+H_{5-p-q}G^a_q$, —$C_6S_2N_p{}^+H_{4-p-q}G^a_q$, —$C_6OSN_p{}^+H_{4-p-q}G^a_q$, —$C_8SN_p{}^+H_{6-p-q}G^a_q$;

"heteroaryl" may be selected from —$C_{5-p}N_pH_{8-o-p-q}G^a_q$, —$C_{6-p}N_pH_{10-o-p-q}G_q$, —$C_{7-p}N_pH_{12-o-p-q}G^a_q$, —$C_{8-p}N_pH_{14-o-p-q}G^a_q$, —$C_{9-p}N_pH_{16-o-p}G^a_q$, —$C_{10-p}N_pH_{18-o-p-q}G^a_q$, —$C_{5-p}O_pH_{8-o-2p-q}G^a_q$, —$C_{6-p}O_pH_{10-o-2p-q}G^a_q$, —$C_{7-p}O_pH_{12-o-2p-q}G^a_q$, —$C_{8-p}O_pH_{14-o-2p-q}G^a_q$, —$C_{9-p}O_pH_{16-o-2p-q}G^a_q$, —$C_{10-p}O_pH_{18-o-2p-q}G^a_q$, —$C_{5-p}S_pH_{8-o-2p-q}G^a_q$, —$C_{6-p}S_pH_{10-o-2p-q}G^a_q$, —$C_{7-p}S_pH_{12-o-2p-q}G^a_q$, —$C_{8-p}S_pH_{14-o-2p-q}G^a_q$, —$C_{9-p}S_pH_{16-o-2p-q}G^a_q$, —$C_{10-p}S_pH_{18-o-2p-q}G^a_q$, —$C_{5-p}O_lN_pH_{8-o-p-2l-q}G^a_q$, —$C_{6-p}O_lN_pH_{10-o-p-2l-q}G^a_q$, —$C_{7-p}O_lN_pH_{12-o-p-2l-q}G^a_q$, —$C_{8-p}O_lN_pH_{14-o-p-2l-q}G^a_q$, —$C_{9-p}O_lN_pH_{16-o-p-2l-q}G^a_q$, —$C_{10-p}O_lN_pH_{18-o-p-2l-q}G^a_q$, —$C_{5-p}S_lN_pH_{8-o-p-2l-q}G^a_q$, —$C_{6-p}S_lN_pH_{10-o-p-2l-q}G^a_q$, —$C_{7-p}S_lN_pH_{12-o-p-2l-q}G^a_q$, —$C_{8-p}S_lN_pH_{14-o-p-2l-q}G^a_q$, —$C_{9-p}S_lN_pH_{16-o-p-2l-q}G^a_q$, —$C_{10-p}S_lN_pH_{18-o-p-2l-q}G^a_q$; and/or "amine" may be selected from —$C_nH_{2n}$—$NH_2$, —$C_nH_{2n}$—$NHG^a$, —$C_nH_{2n}$-$NG^a_2$, —$C_nH_{2n}$-$NG^a_3{}^+$, wherein l=1, 2, 3, 4 n=1, 2, 3, 4, 5, 6, 7, 8, 9, 10, more preferably n=1, 2, 3, 4, 5, 6, most preferably n=1, 2, 3 or 4 m=1, 2, 3, 4, 5, 6, 7, 8, 9, 10, more preferably m=1, 2, 3, 4, most preferably m=1 or 2 o=1, 2, 3, 5, 7, 9 p=1, 2, 3, 4, 5, 6, more preferably p=3, 4, 5 or 6 q=1, 2, 3, 4, 5, more preferably q=1, 2 or 3, s=1, 2, 3, 4, 5 or 6;

each $G^a$ is independently selected from

—H, -Alkyl, -Alkyl$G^b$, -Aryl, —$SO_3H$, —$SO_3^-$, —$PO_3H_2$, —OH, —OAlkyl, —OOH, —OOAlkyl, —SH, -SAlkyl, —$NH_2$, —NHAlkyl, —$NAlkyl_2$, —$NAlkyl_3{}^+$, —$NHG^b$, -$NG^b_2$, —$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+$OAlkyl, —F, —Cl, and —Br;

wherein each $G^b$ is independently selected from

—H, -Alkyl, -Aryl, —$SO_3H$, —$SO_3^-$, —$PO_3H_2$, —OH, —OAlkyl, —OOH, —OOAlkyl, —SH, -SAlkyl, —$NH_2$, —NHAlkyl, —$NAlkyl_2$, —$NAlkyl_3{}^+$, —CHO, —COOH, —COOAlkyl, —CN, —$CONH_2$, —CONHAlkyl, —CON-$Alkyl_2$, -Heteroaryl, -Heterocycyl, —$N^+$OAlkyl, —F, —Cl, and -Br.

In some embodiments, in the above substituent definitions, each $G^a$ is independently not selected from —OOH, —OOAlkyl, —SH, —$NOG^b$ and —$N^+$OAlkyl, wherein $G^b$ is as defined elsewhere herein. In some embodiments, in the above substituent definitions, each $G^b$ is independently not selected from —OOH, —OOAlkyl, —SH, and —$N^+$OAlkyl.

Preferably, the compounds of General formulae (1) to (6) comprise 2-5 substituents as defined above, wherein said 2-5 substituents are preferably not selected from —H. More preferably, the compounds according to the present invention comprise 3-4 substituents as defined above, wherein said 3-4 substituents are preferably not selected from —H.

In some embodiments, 2-5 or 1-5, more preferably 1, 3 or 4 or 3-4 of $R^1$-$R^8$ in General Formula (1), $R^1$-$R^{10}$ in General Formula (2), $R^1$-$R^4$ in General Formula (3), $R^1$-$R^6$ in General Formula (4), $R^1$-$R^6$ in General Formula (5), and $R^1$-$R^8$ in General Formula (6)

are independently selected from -Alkyl, -Alkyl$G^a$, -Aryl, —$SO_3H$, —$SO_3$, —$PO_3H_2$, —OH, —$OG^a$, —SH, -Amine, —$NH_2$, —CHO, —COOH, —$COOG^a$, —CN, —$CONH_2$, —$CONHG^a$, —$CONG^a_2$, -Heteroaryl, -Heterocycyl, —$NOG^a$, —$N^+OG^a$, —F, —Cl, and —Br, or are joined together to form a saturated or unsaturated carbocycle, more preferably from —H, -Alkyl, -AlkylG$^a$, —$SO_3H$/—$SO_3^-$, —$OG^a$, and —COOH;

wherein each $G^a$ is independently selected from —H, -Alkyl, -AlkylG$^b$, -Aryl, —$SO_3H$, —$SO_3^-$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —$NHG^b$, -$NG^b_2$, -$NG^b_3{}^+$, —CHO, —COOH, —COOAlkyl, —CN, —$CONH_2$, —CONHAlkyl, —$CONAlkyl_2$, -Heteroaryl, -Heterocycyl, —$NOG^b$, —$N^+$OAlkyl, —F, —Cl, and —Br;

wherein each $G^b$ is independently selected from —H, -Alkyl, -Aryl, —$SO_3H$, —$SO_3^-$, —$PO_3H_2$, —OH, —OAlkyl, —OOH, —OOAlkyl, —SH, -SAlkyl, —$NH_2$, —NHAlkyl, —$NAlkyl_2$, —$NAlkyl_3^+$, —CHO, —COOH, —COOAlkyl, —CN, —$CONH_2$, —CONHAlkyl, —$CONAlkyl_2$, -Heteroaryl, -Heterocycyl, —$N^+$OAlkyl, —F, —Cl, and -Br.

In some embodiments, each $R^1$-$R^8$ in General Formula (1), each $R^1$-$R^{10}$ in General Formula (2), each $R^1$-$R^4$ in General Formula (3), each $R^1$-$R^6$ in General Formula (4), each $R^1$-$R^6$ in General Formula (5), and each $R^1$-$R^8$ in General Formula (6) is independently not selected from —SH, —$NOG^a$ and —$N^+OG^a$, wherein $G^a$ is as defined above.

In some embodiments, each $G^a$ in any one of General Formulae (1)-(6) is independently not selected from —OOH, —OOAlkyl, —SH, —$NOG^b$ and —$N^+$OAlkyl, wherein $G^b$ is as defined above.

In some embodiments, each $G^b$ in any one of General Formulae (1)-(6) is independently not selected from —OOH, —OOAlkyl, —SH, and —$N^+$OAlkyl.

In some embodiments, the compounds of General Formulae (1)-(6) may preferably comprise at least one —$SO_3H$/—$SO_3^-$ group.

In some embodiments, the compounds of General Formulae (1)-(6) may preferably comprise at least one hydroxyl group. If more than one hydroxyl group is represented, they are preferably located at adjacent positions of the ring system.

In some embodiments, the compounds of General Formulae (1)-(6) may preferably comprise at least one alkyl group.

In some embodiments, the compounds of General Formulae (1)-(6) may preferably comprise at least one alkyoxy (alkoxy) group.

In some embodiments, the compounds of General Formulae (1)-(6) may preferably comprise at least one carboxyl group.

In some embodiments, the compounds of General Formulae (1)-(6) may preferably comprise at least one amine group.

Preferred compounds of General Formulae (1)-(6) to be combined with the phenazine compounds of the present invention according to formula (I) for providing the composition according to the invention are e.g. selected from the following compounds (or their reduced counterparts) (formulae presented on the right hand side reflect the same compound, however, presented upon rotation about the compounds' N-N axis, thereby representing the sulfonyl group at position 3 of the ring system (according to the nomenclature as defined by formulae (I)(a) and (I)(b))):

(i)

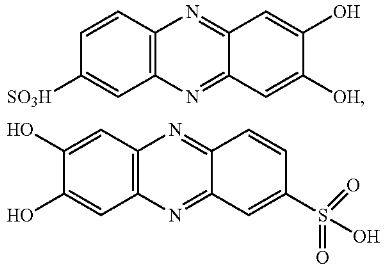

(ii)

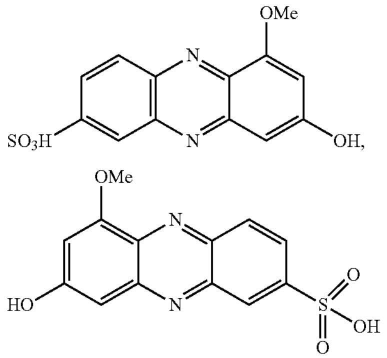

(iii)

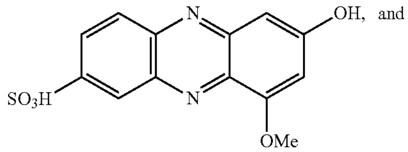

and (iv)

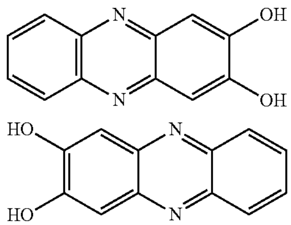

or any combination of two or more of the above. The —OMe and —OH substituents may be positioned at any of positions 1, 2, 3 and 4 of the phenazine ring system.

Other specifically preferred compounds of General Formulae (1)-(6) (or their reduced counterparts) to be contained by the composition according to the invention are selected from (v)

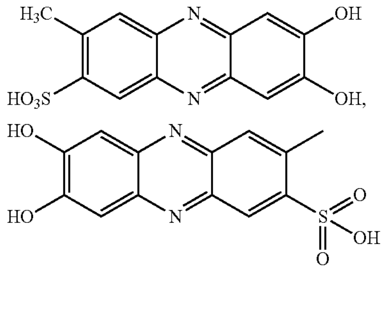

-continued (vi)

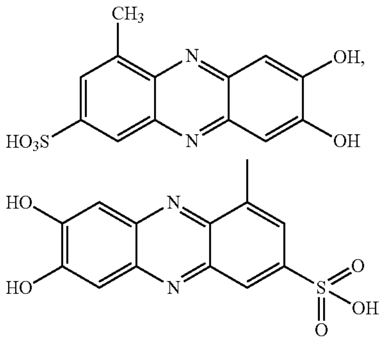

and (vii)

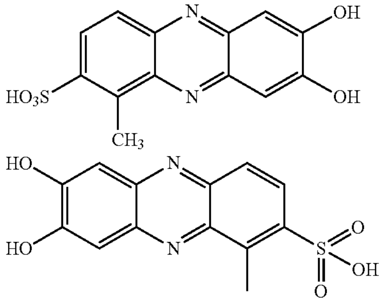

or any combination thereof, in particular a combination of all of the above three compounds each having a methyl group at another position of the phenazine ring system.

Other preferred compounds of General Formulae (1)-(6) (or their reduced counterparts) are selected from (viii)

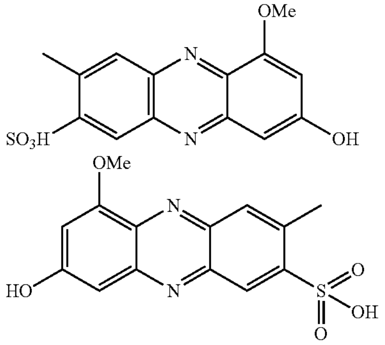

and (ix)

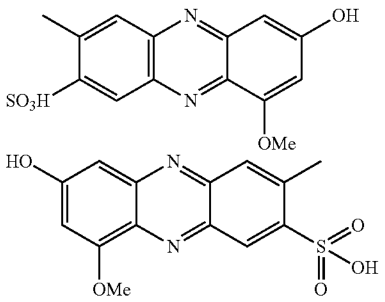

or a combination thereof.

By a specific embodiment, above compounds (i) to (ix) or any combination thereof are excluded as "substituted phenazine compounds" according to the present disclosure.

The composition according to the present invention may preferably comprise or (essentially) consist of at least 1, or a plurality of at least 2, 3, 4, 5 or more compounds of the present invention as defined above and in addition at least one compound according to any one of General Formulae (1)-(6) as defined above.

The compounds of General Formulae (1)-(6) may typically cycle between their reduced and oxidized form, as indicated by Sub-Formulae (a) and (b) of each General Formula (1)-(6). By way of example, a composition comprising a compound according to General Formula (1) will typically comprise the compound in its reduced and oxidized form, as indicated by Sub-Formulae (1) (a) and (1) (b). The amount and ratio of oxidized versus reduced forms typically depends on the redox conditions.

Preferably, the inventive composition may comprise or (essentially) consist of a plurality of at least 2, 3, 4, 5 or more compounds of the present invention, each of which is present in its oxidized and reduced form.

The inventive composition may further comprise at least 1 or a plurality of at least 2, 3, 4, 5 or more compounds according to General Formula (1), (2), (3), (4), (5) or (6). Each of the aforementioned compounds may be present in its reduced and/or oxidized form.

The compositions according to the present invention may exhibit favorable electrochemical properties and be particularly useful as, e.g., redox flow battery electrolytes. This is advantageous as it may preferably obviate the need for purification steps after the substitution reaction has been performed. Rather, the inventive compositions comprising mixtures of the compounds according to the invention may be "ready to use" (e.g., as redox flow battery electrolytes") after "batch" substitution reactions.

The compounds according to formula (I) or the compounds according to any of General Formulae (1) to (6) all represent a phenazine ring skeleton as their basic structural element.

The synthesis of phenazine core structures is well established and extensively described in the art. Exemplary synthetic routes are summarized, however, a person skilled in the art will be able to use known reaction protocols to synthesize structurally similar phenazine cores. Phenazines can be condensation products of o-amino-anilines with quinone based coupling partners, which can be either conducted in solution (as e.g. described by WO 2018/231926 A1) or in melt (see J. S. Morley, J. Chem. Soc. (1952), p. 4008-4014). Alternatively, 2-nitrophenylendiamines can be cycled with the aid of basic metal alcoholates (see e.g. JP 47-144440). A person skilled in the art will understand that desired substitution patterns at the phenazine core can be realized by the choice of reaction partners with suitable substituents for the desired phenazine compound synthesis.

To fine-tune the properties of phenazines, the substituted phenazine cores can be further functionalized by a number of synthetic methods of which certain exemplary routes are shown below. A person skilled in the art will understand that multiple synthetic pathways to a target molecule exist; thus, the following methods are representative without summarizing all available synthetic routes.

Some embodiments of the disclosed phenazines compounds are synthesized employing a nucleophilic substitution with amino- or alcohol-functionalized phenazines as nucleophilic reaction partners.

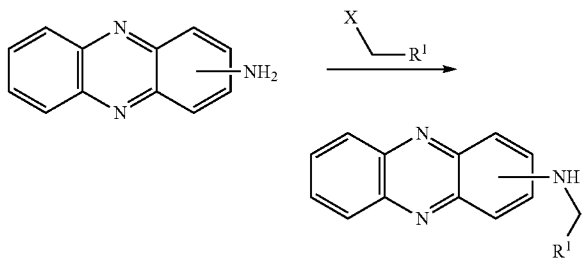

Some other embodiments of the disclosed phenazine compounds are synthesized by nucleophilic ring-opening of cyclic sulfonates (sultones) and cyclic ethers (e.g. epoxides) by amino- or alcohol-functionalized phenazines

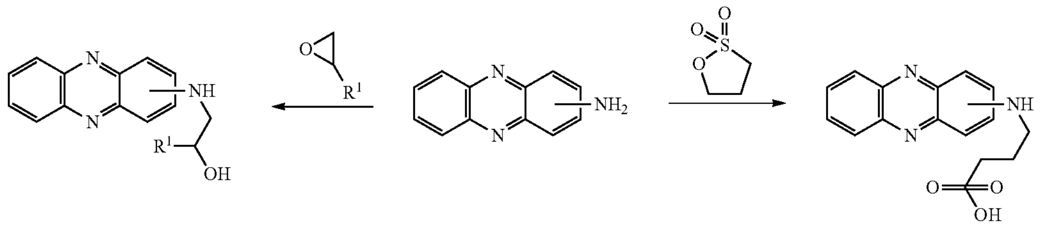

A person skilled in the art will understand that these reactions can be combined or employed in subsequent sequences.

The compounds and compositions according to the present invention are usable or used as redox flow battery electrolytes according to the present invention.

A "(redox flow battery) electrolyte" refers to a substance that is capable of conducting electrical currents via electron transfer in a redox flow battery. Said redox flow battery electrolytes are typically provided as electrolyte solutions. Said "electrolyte solution" may preferably comprises at least one target compound or composition according to the present invention acting as an electrolyte, and at least one solvent. The at least one compound or composition according to the present invention is dissolved or suspended in a suitable solvent. The solvent may preferably be selected from water and an organic solvent which is preferably miscible with water such as, e.g. methanol, ethanol, dimethylsulfoxide, acetonitrile, acetone and glycol. The electrolyte solution may comprise further additives, including acids, bases, buffers, ionic liquids, stabilizers, and the like.

Compounds and compositions according to the present invention may be used as catholytes (posolytes) and/or anolytes (negolytes). The term "catholytes" refers to the part or portion of an electrolyte, which is on the cathode side of a redox-flow battery half-cell, whereas the term "anolyte" refers to the part or portion of an electrolyte, which is on the anode side of a redox-flow battery half-cell. It is conceivable to employ the inventive phenazine compounds both as catholytes and anolytes in each half-cell (i.e. anode side and cathode side) of the same redox flow battery, thereby providing an "all-organic" redox flow battery. It is, however, preferred to provide the phenazine compounds or compositions according to the invention as either catholytes or anolytes in a "half-organic" redox flow battery. Therein, phenazine compounds or compositions according to the invention are utilized either as anolytes (catholytes), whereas the catholyte (anolyte) comprises an inorganic redox active species. Examples for such inorganic redox active species include transition metal ions and halogen ions, such as $VCl_3/VCl_2$, $Br/ClBr_2$, $Cl_2/Cl^-$, $Fe^{2+}/Fe^{3+}$, $Cr^{3+}/Cr^{2+}$, $Ti^{3+}/Ti^{2+}$, $V^{3+}/V^{2+}$, $Zn/Zn^{2+}$, $Br_2/Br^-$, $I^{3-}/I^-$, $VBr_3/VBr_2$, $Ce^{3+}/Ce^{4+}$, $Mn^{2+}/Mn^{3+}$, $Ti^{3+}/Ti^{4+}$, $Cu/Cu^+$, $Cu^+/Cu^{2+}$, in particular $Fe^{2+}/Fe^{3+}$ and others. It may be preferred to employ transition metal complexes, e.g. $Fe^{2+}/Fe^{3+}$ complexes.

Generally, a catholyte is charged when a redox couple is oxidized to a higher one of two oxidation states, and is discharged when reduced to a lower one of the two oxidation state:

Cathode:

(C: Catholyte/Posolyte)

$$C^n \xrightarrow{\text{yields}} C^{n-z} + ze^- \text{ (Charge)}$$

$$C^{n-z} + ze^- \xrightarrow{\text{yields}} C^n \text{ (Discharge)}$$

In contrast, an anolyte is charged when a redox couple is reduced to a lower one of two oxidation states, and is discharged when oxidized to a higher one of the two oxidation states:

Anode:

(A: Anolyte/Negolyte)

$$A^{n-x} + xe^- \xrightarrow{\text{yields}} A^n \text{ (Charge)}$$

$$A^n \xrightarrow{\text{yields}} A^{n-x} + xe^- \text{ (Discharge)}$$

The standard (redox flow battery) cell potential ($E°_{cell}$) is the difference in the standard electrode potentials (against the standard hydrogen electrode (SHE)) of the two half-cell reactions of the catholyte and anolyte.

$$E_{cell}^0 = E_{cat}^0 - E_{an}^0 \qquad \text{eq.1}$$

($E°_{cell}$=(redox flow battery) cell potential under standard conditions, $E°_{cat}$: standard reduction potential for the reduction half reaction occurring at the cathode, $E°_{an}$: standard reduction potential for the oxidation half reaction occurring at the anode).

The Nernst Equation (eq. 2) enables the determination of cell potential under non-standard conditions. It relates the measured cell potential to the reaction quotient and allows the accurate determination of equilibrium constants (including solubility constants).

$$E_{cell} = E^0_{cell} - \frac{RT}{nF}\ln Q \qquad \text{eq. 2}$$

($E_{cell}$=(redox flow battery) cell potential under non-standard conditions, n=number of electrons transferred in the reaction, F=Faraday constant (96,500 C/mol), T=Temperature and Q=reaction quotient of the redox reaction).

The redox flow battery cell potential thus depends on the concentration and types of reactants (which determines the number of transferred electrons and the reaction quotient). It will be understood that a redox flow battery employing the target compounds or compositions according to the invention as a catholyte and/or anolyte preferably exhibit high (standard) cell potentials. Preferably, the redox flow battery employing (a) target compound(s) or compositions as catholytes and/or anolytes exhibits a cell potential of at least +0.5 V, preferably at least +0.8 V, more preferably at least +1.0 V, or more, typically between +0.5 and +1.5 V, preferably between +0.8 and +1.2 V for the open circuit voltage (OCV) in the fully charged state. Suitable stabilizers can enhance the cell potential to a range typically between +0.5 V and +2.5 V against SHE.

Compounds and compositions according to the present invention, which are envisaged for use as catholytes (accepting electrons in a reduction reaction during discharge) thus preferably exhibit standard reduction potentials (against SHE) $E^0_{cat}$ that are more positive (less negative) than the standard reduction potential for the employed anolyte ($E^0_{an}$). Preferably, target compounds or compositions intended for use as catholytes exhibit positive standard reduction potentials $E^0_{cat}$ of more than 0 V, more preferably of at least +0.5 V, most preferably at least +0.7 V against SHE.

Compounds and compositions according to the present invention, which are envisaged for use as anolytes/negolytes (donating electrons in an oxidation reaction during discharge) thus preferably exhibit standard reduction potentials (against SHE) $E^0_{an}$ that are more negative (less positive) than the standard reduction potential for the employed catholyte/posolyte ($E^0_{cat}$). Preferably, target compounds or compositions intended for use as anolytes exhibit standard reduction potentials of less than +0.3 V, preferably +0.1 V or less against SHE.

The standard reduction potential of the redox couple is characteristic of the molecule and its specific substituent groups and is inter alia related to the electronic energy of the molecular orbitals. For instance, $—SO_3H/—SO_3^-$ groups may increase the standard reduction potential, which is consistent with the lowering of molecular orbital energies by electro-withdrawing groups.

While the equilibrium potentials of electrolytes in the cathodic and anodic half-cells determines the cell voltage, its capacity depends on the effective electrolyte concentration, which is the solubility multiplied by the number of electrons transferred in the redox reactions. Highly soluble electrolytes therefore preferably increase the energy capacity of the redox flow battery and are therefore preferred.

For instance, $—SO_3H/—SO_3^-$ and amine groups are preferably capable of increasing the solubility of the substituted compound(s) in water, which preferably provides for an electrolyte solution usable in redox flow batteries exhibiting a high capacity. The compounds or compositions according to the invention are preferably soluble in concentrations of at least 0.3 M, preferably at least 0.6 M, more preferably at least 1.0 M at 25° C.

The compounds or compositions according to the present invention are typically redox active. The compounds or compositions according to the present invention are envisaged as electrolytes. Preferably, said compounds or compositions are thus provided in the form of an electrolyte solution for redox flow battery applications. Compounds and compositions according to the present invention may preferably be dissolved or suspended in a suitable solvent (e.g. water) to yield an electrolyte solution for use in redox flow batteries. Compounds and compositions according to the present invention may be provided in solid or liquid form.

Preferably, compounds and compositions according to the present invention, which are preferably provided as redox flow battery electrolytes, may be dissolved or suspended in aqueous solution, e.g. an aqueous solvent system, thereby forming an electrolyte solution.

The term "aqueous solvent system" refers to a solvent system comprising preferably at least about 20% by weight of water, relative to total weight of the solvent. In some applications, soluble, miscible, or partially miscible (emulsified with surfactants or otherwise) co-solvents may also be usefully present which, for example, extend the range of water's liquidity (e.g., alcohols/glycols). In addition to the redox active electrolytes described herein, the electrolyte solutions may contain additional buffering agents, supporting electrolytes, viscosity modifiers, wetting agents, and the like, which may be part of the solvent system.

Thus, the term "aqueous solvent system" may generally include those comprises at least about 50 or 55%, at least about 60 wt %, at least about 70 wt %, at least about 75 wt %, at least about 80%, at least about 85 wt %, at least about 90 wt %, at least about 95 wt %, or at least about 98 wt % water, relative to the total solvent. Sometimes, the aqueous solvent may consist essentially of water, and be substantially free or entirely free of co-solvents or other (non-target compound) species. The solvent system may be at least about 90 wt %, at least about 95 wt %, or at least about 98 wt % water, or may be free of co-solvents or other (non-target compound) species.

One or both electrolyte solutions may be characterized as having a pH of between about $<0$ and about $>14$. The pH of the electrolyte solution may be maintained by a buffer. Typical buffers include salts of phosphate, borate, carbonate, silicate, trisaminomethane (Tris), 4-(2-hydroxyethyl)-1-piperazineethanesulfonic acid (HEPES), piperazine-N,N'-bis (ethanesulfonic acid) (PIPES), and combinations thereof. A user may add an acid (e.g., HCl, $HNO_3$, $H_2SO_4$ and the like), a base (NaOH, KOH, and the like), or both to adjust the pH of a given electrolyte solution as desired.

The pH of the first and second electrolyte solutions may be equal or substantially similar; or the pH of the two electrolytes differ by a value in the range of about 0.1 to about 2 pH units, about 1 to about 10 pH units, about 5 to about 12 pH units, about 1 to about 5 pH units, about 0.1 to about 1.5 pH units, about 0.1 to about 1 pH units, or about 0.1 to about 0.5 pH units. In this context, the term "substantially similar," without further qualification, is intended to connote that the difference in pH between the two electrolytes is about 1 pH unit or less, such as about 0.4 or less, about 0.3 or less, about 0.2 or less, or about 0.1 pH units or less.

Redox Flow Battery

In a further aspect, the present invention provides a redox flow battery comprising at least one compound or composition according to the present invention.

The present invention further provides a redox flow battery comprising a first half cell comprising an electrolyte solution comprising a composition according to the present invention; and a second half-cell comprising an electrolyte solution comprising another redox active species.

Typically, the redox-active compounds of the half-cells of the redox flow battery represent a distinct electrochemical potential. The larger the difference of the electrochemical potential of the redox active species of each half cell, the higher is the battery energy storage capacity. The second half cell has typically a standard potential of ≥0V vs. SHE, more preferably >0.2V vs. SHE.

According to a preferred embodiment, the present invention provides a redox flow battery as described above, wherein said redox flow battery comprises

- a first (optionally aqueous) electrolyte solution comprising a first (redox active) compound;
- a first electrode in contact with said first (optionally aqueous) electrolyte solution;
- a second (optionally aqueous) electrolyte solution comprising a second (redox active) electrolyte;
- a second electrode in contact with said second (optionally aqueous) electrolyte solution;

wherein at least one of the first and second (redox active) electrolyte solutions is selected from a composition according to the present invention; and

- a separator, preferably a polymer membrane interposed between the first and the second electrode, which may preferably be a cation exchange membrane.

According to a further preferred embodiment, the present invention provides a redox flow battery as described above, wherein said Redox Flow Battery comprises at least one flow-by electrode.

According to a moreover preferred embodiment, the present invention provides a redox flow battery as described above, wherein said redox flow battery comprises at least one carbon-based electrode, preferably at least one of the electrodes of the redox flow battery is coated with a carbon-based active layer.

According to a further preferred embodiment, the present invention provides a redox flow battery as described above, wherein said redox flow battery comprises a carbon-based electrode other than carbon felt, carbon cloth and carbon paper.

According to a moreover preferred embodiment, the present invention provides a redox flow battery as described above, wherein

- the first (optionally aqueous) electrolyte solution comprises, preferably as the negolyte, a composition according to the present invention; and
- the second (optionally aqueous) electrolyte solution comprises, preferably as the posolyte, a composition comprising at least one inorganic redox active species, preferably a metal ion salt, more preferably an Fe ion salt.

According to a further preferred embodiment, the present invention provides a redox flow battery as described above, wherein the second (optionally aqueous) electrolyte solution comprises a salt of $Fe(CN)_6^{3-}$, $Fe(CN)_6^{4-}$ and/or combinations thereof, preferably an alkali salt or a combination of alkali salts, more preferably a $Na^+$ and/or $K^+$ salt. The second (optionally aqueous) electrolyte solution comprises a salt, in particular an alkali salt, of $Fe(CN)_6^{3-}$, $Fe(CN)_6^{4-}$ and/or combinations thereof, wherein the total molarity of the salt, in particular the alkali salt, of $Fe(CN)_6^{3-}$, $Fe(CN)_6^{4-}$ and/or combinations thereof is 1.0 M or less. Preferably, the second (optionally aqueous) electrolyte solution comprises a combination of alkali salts and a combination of $Fe(CN)_6^{3-}$ and $Fe(CN)_6^{4-}$, more preferably with a total molarity of about 1.0 M or less.

Redox flow batteries typically comprise two parallel electrodes separated by a suitable separator, such as an ion exchange membrane, forming two half-cells. Preferably, redox flow batteries according to the invention thus comprise (1) a first half-cell comprising a first or negative electrode contacting a first (optionally aqueous) electrolyte solution comprising the first electrolyte; (2) a second half-cell comprising a second or positive electrode contacting a second (optionally aqueous) electrolyte solution comprising the second electrolyte; and (3) a separator (or "barrier") disposed between the first and second electrolytes. Preferably, the electrolytes are provided in liquid form, either in pure liquid form or dissolved in a suitable solvent, i.e. as electrolyte solutions. The electrolyte, which is in contact with the negative electrode, may also be referred to as the "negolyte". The electrolyte, which is in contact with the positive electrode, may also be referred to as the "posolyte".

The redox flow battery cell typically comprises of a first redox flow battery half-cell harbouring the positive electrode in contact with the first electrolyte solution and—separated therefrom by a suitable separator or barrier—a second half-cell harbouring a negative electrode in contact with the second electrolyte solution. Preferably, the half-cells are configured as separate reservoirs (or chambers) within the redox flow battery cell, through which the first and/or second electrolyte solutions flow so as to contact the respective electrodes disposed in the electrolyte solution, and the separator.

The negative electrode reservoir ("negolyte chamber") comprises the negative electrode immersed within the negative electrode electrolyte in a container and forms a first redox flow battery half-cell; and the positive electrode chamber ("posolyte chamber") comprises the positive electrode immersed within the positive electrode electrolyte in a container and forms the second redox flow battery half-cell. Each container and its associated electrode and electrolyte solution thus defines its corresponding redox flow battery half-cell. The containers of each redox flow battery half-cell may be composed of any preferably chemically inert material suitable to retain the respective electrolyte solutions. Each electrolyte preferably flows through its corresponding redox flow battery half-cell flow so as to contact the respective electrode disposed within the electrolyte, and the separator. The electrochemical redox reactions of the employed electrolytes occur within the redox flow battery half-cells.

Specifically, the current invention thus provides a redox flow battery comprising: a first (optionally aqueous) electrolyte solution comprising a first (redox active) electrolyte; a first electrode in contact with said first (optionally aqueous) electrolyte solution; a second (optionally aqueous) electrolyte solution comprising a second (redox active) electrolyte; a second electrode in contact with said second (optionally aqueous) electrolyte solution; wherein one or both of the first and second (redox active) electrolytes comprise at least one inventive phenazine compound as defined herein, or a composition comprising or (essentially) consisting of the same as defined herein.

The posolyte and negolyte chamber defining the corresponding redox flow battery half-cells are preferably connected to a power source. Further, each chamber may be connected, preferably via suitable ducts, to at least one separate storage tank comprising the respective electrolyte solution flowing through said chamber. The storage tank volume determines the quantity of energy stored in the system, which may be measured in kWh. The ducts may comprise transportation means (e.g. pumps, openings, valves, ducts, tubing) for transporting the electrolyte solutions from the storage tanks through the corresponding half-cell chamber.

The redox flow battery cell may further comprise control software, hardware, and optional safety systems such as sensors, mitigation equipment, meters, alarms, wires, circuits, switches, signal filters, computers, microprocessors, control software, power supplies, load banks, data recording equipment, power conversion equipment, and other devices and other electronic/hardware controls and safeguards to ensure safe, autonomous, and efficient operation of the redox flow battery. Such systems are known to those of ordinary skill in the art.

Typically, the first redox flow battery half-cell is separated from the second redox flow battery half-cell by a separator (also referred to as a "membrane" or "barrier" herein). Said separator preferably functions to (1) (substantially) prevent mixing of first and second electrolyte, i.e. physically separates the posolyte and negolyte from each other; (2) reduces or prevents short circuits between the positive and negative electrodes; and (3) enables ion (typically $H^+$) transport between the positive and negative electrolyte chambers, thereby balancing electron transport during charge and discharge cycles. The electrons are primarily transported to and from an electrolyte through the electrode contacting that electrolyte.

Suitable separator materials may be chosen by the skilled artisan from separator materials known in the art as long as they are (electro-)chemically inert and do not, for example, dissolve in the solvent or electrolyte. Separators are preferably cation-permeable, .e. allow the passage of cations such as $H^+$ (or alkali ions, such as sodium or potassium), but is at least partially impermeable to the redox active compounds. The separator may for instance be selected from an ion conducting membrane or a size exclusion membrane.

Separators are generally categorized as either solid or porous. Solid separators may comprise an ion-exchange membrane, wherein an ionomer facilitates mobile ion transport through the body of the polymer which constitutes the membrane. The facility with which ions conduct through the membrane can be characterized by a resistance, typically an area resistance in units of ohm-$cm^2$. The area resistance is a function of inherent membrane conductivity and the membrane thickness. Thin membranes are desirable to reduce inefficiencies incurred by ion conduction and therefore can serve to increase voltage efficiency of the redox flow battery cell. Active material crossover rates are also a function of membrane thickness, and typically decrease with increasing membrane thickness. Crossover represents a current efficiency loss that must be balanced with the voltage efficiency gains by utilizing a thin membrane.

Such ion-exchange membranes may also comprise or consist of membranes, which are sometimes referred to as polymer electrolyte membranes (PEMs) or ion conductive membranes (ICMs). The membranes according to the present disclosure may comprise any suitable polymer, typically an ion exchange resin, for example comprising a polymeric anion or cation exchange membrane, or combination thereof. The mobile phase of such a membrane may comprise, and/or is responsible for the primary or preferential transport (during operation of the battery) of at least one mono-, di-, tri-, or higher valent cation and/or mono-, di-, tri-, or higher valent anion, other than protons or hydroxide ions.

Additionally, substantially non-fluorinated membranes that are modified with sulfonic acid groups (or cation exchanged sulfonate groups) may also be used. Such membranes include those with substantially aromatic backbones, e.g., poly-styrene, polyphenylene, bi-phenyl sulfone (BPSH), or thermoplastics such as polyetherketones or polyethersulfones. Examples of ion-exchange membranes comprise NAFION®.

Porous separators may be non-conductive membranes that allow charge transfer between two electrodes via open channels filled with conductive electrolyte solution. Porous membranes are typically permeable to liquid or gaseous chemicals. This permeability increases the probability of chemicals (e.g. electrolytes) passing through porous membrane from one electrode to another causing cross-contamination and/or reduction in cell energy efficiency. The degree of this cross-contamination depends on, among other features, the size (the effective diameter and channel length), and character (hydrophobicity/hydrophilicity) of the pores, the nature of the electrolyte, and the degree of wetting between the pores and the electrolyte solution. Because they contain no inherent ionic conduction capability, such membranes are typically impregnated with additives in order to function. These membranes are typically comprised of a mixture of a polymer, and inorganic filler, and open porosity. Suitable polymers include those chemically compatible with the electrolytes and electrolyte solutions described herein, including high density polyethylene, polypropylene, polyvinylidene difluoride (PVDF), or polytetrafluoroethylene (PTFE). Suitable inorganic fillers include silicon carbide matrix material, titanium dioxide, silicon dioxide, zinc phosphide, and ceria and the structures may be supported internally with a substantially non-ionomeric structure, including mesh structures such as are known for this purpose in the art.

Separators may feature a thickness of about 500 microns or less, about 300 microns or less, about 250 microns or less, about 200 microns or less, about 100 microns or less, about 75 microns or less, about 50 microns or less, about 30 microns or less, about 25 microns or less, about 20 microns or less, about 15 microns or less, or about 10 microns or less, for example to about 5 microns.

In a more preferred embodiment, the separator may a membrane containing at least two layers, wherein one layer is a porous polymer carrier layer and another layer being preferably a membrane. The polymer carrier layer may be preferably a micro-porous polyethylene carrier layer, the other layer may be preferably a PEEK layer, which may be sulfonated. While, as indicated above, the separator in general has a thickness of about 5 to 500 microns and, more preferably, 10 to 100 microns, a double layer separator may more preferably have a thickness of between 10 to 50 or 10 to 30 microns.

The negative and positive electrodes of the inventive redox flow battery provide a surface for electrochemical reactions during charge and discharge. As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to the reversible hydrogen electrode. The negative electrode is associated with the first aqueous electrolyte and the positive electrode is associated with the second electrolyte, as described herein.

The inventive redox flow battery comprises a first (positive) and second (negative) electrode (cathode and anode, respectively).

The negative and positive electrodes of the inventive redox flow battery provide a surface for electrochemical reactions during charge and discharge. The first and second electrode may comprise or consist of the same or a different material(s).

Suitable electrode materials may be selected from any electrically conductive material that is chemically and electrochemically stable (i.e., inert) under the desired operating conditions. Electrodes may comprise more than one material as long as their surface is preferably covered by an electrically conductive and (electro)chemically inert material.

Exemplary electrode materials for use in the inventive redox flow battery may be selected, without limitation, from a metal, such as titanium, platinum, copper, aluminum, nickel or stainless steel; preferably a carbon material, such as glassy carbon, carbon black, activated carbon, amorphous carbon, graphite, graphene, carbon mesh, carbon paper, carbon felt, carbon foam, carbon cloth, carbon paper, or carbon nanotubes; and an electroconductive polymer; or a combination thereof. The term “carbon material” refers to materials which are primarily composed of the element carbon, and typically further contain other elements, such as hydrogen, sulfur, oxygen, and nitrogen. Carbon materials containing a high surface area carbon may be preferred due to their capability of improving the efficiency of charge transfer at the electrode.

The electrodes may take the form of a plate, which may preferably exhibit an increased surface area, such as a perforation plate, a wave plate, a mesh, a surface-roughened plate, a sintered porous body, and the like. Electrodes also may be formed by applying any suitable electrode material onto the separator.

Preferably, the electrolytes within the inventive redox flow battery are provided in liquid form, either in pure liquid form or dissolved in a suitable solvent, e.g. e.g. water, methanol, ethanol, dimethylsulfoxide, acetonitrile, acetone, glycol or mixtures thereof, i.e. as electrolyte solutions as described in greater detail elsewhere herein.

Accordingly, the redox flow battery according to the invention may comprise (1) a first half-cell comprising a first (redox active) electrolyte, optionally dissolved or suspended in suitable solution, e.g. an aqueous solution, in contact with the first electrode and (2) a second half-cell comprising a phenazine compound as disclosed herein as a second (redox active) electrolyte, which is preferably dissolved or suspended in aqueous solution, in contact with the second electrode, or vice versa.

Optionally, the redox flow battery according to the invention may comprise, as a first redox active electrolyte, an inorganic material, e.g. a chlorine, bromine, iodine, oxygen, vanadium, chromium, cobalt, iron, manganese, cobalt, nickel, copper, or lead, in particular, bromine or a manganese oxide, a cobalt oxide or a lead oxide, e.g. as ligand complexes, e.g. metal (e.g. Fe) complexes, e.g. iron based ligand complexes like $K_4[Fe(CN)_6]$, and, as the second redox active electrolyte, a phenazine compound as described herein, or vice versa.

Alternatively, both the first and the second electrolyte may be selected from a substituted phenazine compound as described herein. The first (redox active) electrolyte may function as the anolyte, and the second (redox active) electrolyte may function as the catholyte, or vice versa.

The disclosed redox flow battery may also be characterized in terms of its half-cell reduction potentials. Both the negative and positive electrode preferably exhibit a half-cell standard reduction potential. A redox flow battery cell according to the present disclosure may exhibit a half-cell potential for the negative electrode less than about +0.3 V vs. SHE, preferably less than about +0.1 V vs. SHE. A redox flow battery cell according to the present disclosure, specifically when employing substituted target compounds as described herein as redox flow battery electrolytes, may exhibit a half-cell potential for the positive electrode at least about +0 V vs. SHE, preferably at least +0.5 V vs. SHE, most preferably at least about 0.7 V vs. SHE.

The disclosed redox flow batteries may also be characterized in terms of their energy density. Flow batteries of the present disclosure may operate with an energy density of, at least between about 10 Wh/L per side and about 20 Wh/L per side, preferably between about 20 Wh/L per side and about 50 Wh/L per side, most preferably between about 50 Wh/L per side and about 100 Wh/L per side.

Operation

In a charging cycle, electrical power is applied to the system. Thereby, the redox active electrolyte contained in the one (for instance the second) electrolyte solution undergoes one-or-more electron oxidation and the redox active electrolyte in the other (for instance the first) electrolyte solution undergoes one-or-more electron reduction. Similarly, in a discharge cycle one (for instance the second) electrolyte is reduced and the other (for instance the first) electrolyte is oxidized producing electrical power.

As indicated above, it is conceivable to employ different phenazine compounds as the first and the second electrolyte in the redox flow batteries according to the invention. Accordingly, the invention thus features a redox flow battery including first and second electrodes separated by a separator, wherein in its charged state, the redox flow battery includes a first substituted target compound in its reduced form at the first electrode and a second substituted target compound in its oxidized form at the second electrode, wherein during discharge, the first target compound is oxidized, and the second target compound is reduced. Specifically, the phenazine compounds may be dissolved or suspended in aqueous solution.

Redox Flow Battery Stacks

In some cases, a user may desire to provide higher charge or discharge voltages than available from a single battery. In such cases, and in certain embodiments, then, several batteries are connected in series such that the voltage of each cell is additive. An electrically conductive, but non-porous material (e.g., a bipolar plate) may be employed to connect adjacent battery cells in a bipolar stack, which allows for electron transport but prevents fluid or gas transport between adjacent cells. The positive electrode compartments and negative electrode compartments of individual cells are suitably fluidically connected via common positive and negative fluid manifolds in the stack. In this way, individual electrochemical cells can be stacked in series to yield a desired operational voltage.

Several redox flow batteries may be connected in series via electrically conductive, preferably non-porous material which allows for electron transport but prevents fluid or gas transport between adjacent cells (e.g., a bipolar plate) in a bipolar redox flow battery stack. Positive and negative electrode compartments of each cell are preferably connected via common positive and negative fluid manifolds in the stack. Thereby, individual electrochemical cells can be stacked in series to yield a desired operational voltage.

The term “bipolar plate” refers to an electrically conductive, substantially nonporous material that may serve to separate electrochemical cells in a cell stack such that the cells are connected in series and the cell voltage is additive across the cell stack. The bipolar plate has two surfaces such that one surface of the bipolar plate serves as a substrate for the positive electrode in one cell and the negative electrode in an adjacent cell. The bipolar plate typically comprises carbon and carbon containing composite materials.

Energy Storage Systems

Redox flow battery cells, cell stacks, or redox flow batteries as described herein comprising the phenazine compounds of the present invention may be incorporated in larger energy storage systems, suitably including piping and controls useful for operation of these large units. Piping, control, and other equipment suitable for such systems are known in the art, and include, for example, piping and pumps in fluid communication with the respective electrochemical reaction chambers for moving electrolytes into and out of the respective chambers and storage tanks for holding charged and discharged electrolytes.

The storage tanks contain the redox active materials; the tank volume determines the quantity of energy stored in the system, which may be measured in kWh. The control software, hardware, and optional safety systems suitably include sensors, mitigation equipment and other electronic/hardware controls and safeguards to ensure safe, autonomous, and efficient operation of the flow battery energy storage system. Such systems are known to those of ordinary skill in the art. A power conditioning unit may be used at the front end of the energy storage system to convert incoming and outgoing power to a voltage and current that is optimal for the energy storage system or the application. For the example of an energy storage system connected to an electrical grid, in a charging cycle the power conditioning unit would convert incoming AC electricity into DC electricity at an appropriate voltage and current for the electrochemical stack. In a discharging cycle, the stack produces DC electrical power and the power conditioning unit converts to AC electrical power at the appropriate voltage and frequency for grid applications.

The energy storage and generation systems described herein may also include electrolyte circulation loops, which may comprise one or more valves, one or more pumps, and optionally a pressure equalizing line. Hence, the energy storage system according to the invention may comprise at least one redox flow battery, a first chamber containing the first (preferably aqueous) electrolyte and a second chamber containing the second (preferably aqueous) electrolyte; at least one electrolyte circulation loop in fluidic communication each electrolyte chamber, said at least one electrolyte circulation loop comprising storage tanks and piping for containing and transporting the electrolytes; control hardware and software (which may include safety systems); and an optional power conditioning unit.

The energy storage and generation systems of this disclosure can also include an operation management system. The operation management system may be any suitable controller device, such as a computer or microprocessor, and may contain logic circuitry that sets operation of any of the various valves, pumps, circulation loops, and the like.

The energy storage systems of the present disclosure are preferably suited to sustained charge or discharge cycles of several hour durations. For example, redox flow batteries comprising the phenazine compounds of the present invention may be capable of retaining at least about 70% efficiency when subjected to 10 charge/discharge cycles. As such, the systems of the present disclosure may be used to smooth energy supply/demand profiles and provide a mechanism for stabilizing intermittent power generation assets (e.g., from renewable energy sources). It should be appreciated, then, that various embodiments, of the present disclosure include those electrical energy storage applications where such long charge or discharge durations are valuable. For example, non-limiting examples of such applications include those where systems of the present disclosure are connected to an electrical grid include, so as to allow renewables integration, peak load shifting, grid firming, baseload power generation consumption, energy arbitrage, transmission and distribution asset deferral, weak grid support, and/or frequency regulation. Cells, stacks, or systems according to the present disclosure may be used to provide stable power for applications that are not connected to a grid, or a micro-grid, for example as power sources for remote camps, forward operating bases, off-grid telecommunications, or remote sensors.

FIGURES

FIG. 1: Galvanostatic charge and discharge cycle (voltage as a function of time) with phenazine compound (III) (see Table 1) in a FT Cell.

Figure 2:
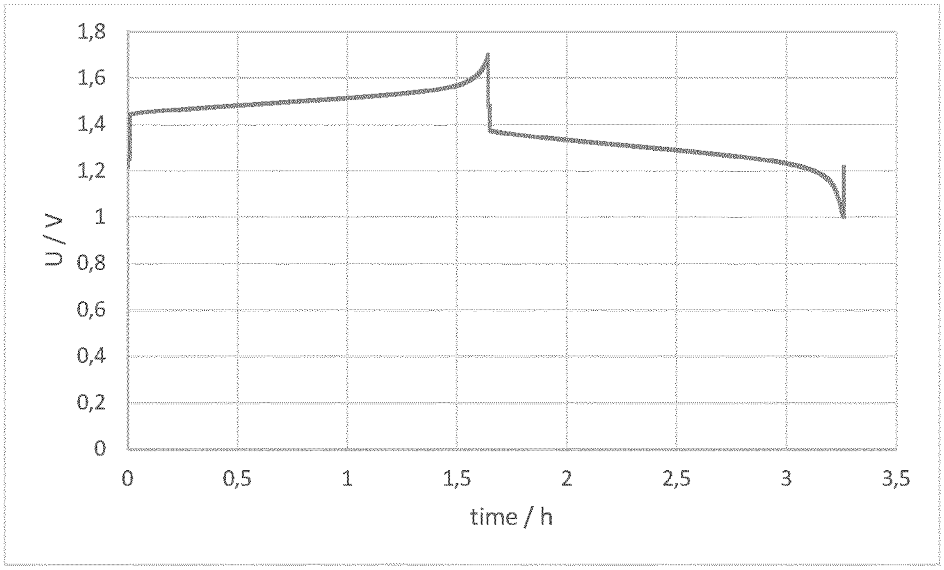

FIG. 2: Galvanostatic charge and discharge cycle (voltage as a function of time) of phenazine compound (II) (see Table I) in a FT-Cell.

Figure 3:
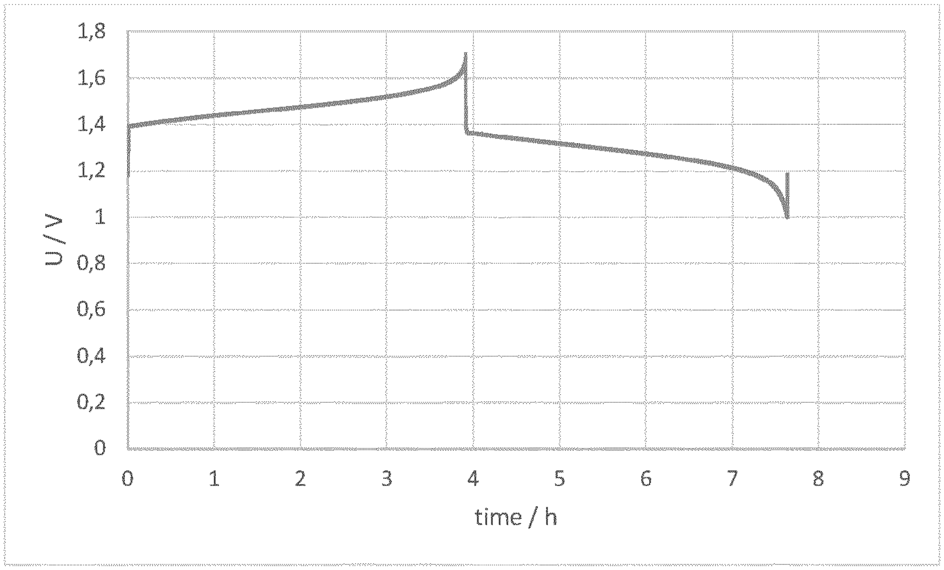

FIG. 3: Galvanostatic charge and discharge cycle (voltage as a function of time) of phenazine compound (II) (see Table I) in a FB-Cell.

EXAMPLES

The examples shown in the following are merely illustrative and shall describe the present invention in a further way. These examples shall not be construed to limit the present invention thereto. The following preparations and examples are given to enable those skilled in the art to more clearly understand and to practice the present invention. The present invention, however, is not limited in scope by the exemplified embodiments, which are intended as illustrations of single aspects of the invention only, and methods, which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

In the following example section, the alternative nomenclature of the synthesized compounds, in particular, considering the denotation of the ring positions according to Formula (I)(a) and (I)(b) is provided below by the terms set in brackets (" . . . ").

I. Synthesis of Phenazine Compounds According to the Present Invention

Example 1: [(3-hydroxyphenazin-2-yl)(methyl)amino]acetic acid ("[(7-hydroxyphenazin-8-yl)(methyl)amino]acetic acid")]

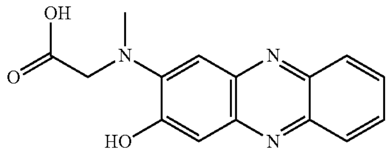 [SMILES: CN(CC(=O)O)c1cc2nc3ccccc3nc2cc1O]

Methoxybenzoquinone (MBQ) (2-Methoxy-1,4-benzoquinone) was first converted to 2-[2-(methylamino)acetic acid]-1,4-benzoquinone by reacting MBQ (2.44 g, 20 mmol, 1 eq) with 2-(methylamino)acetic acid (3.56 g, 40 mmol, 2 eq) in methanol (30 ml) in a 100 ml round bottom flask. After stirring at 60° C. for 40 hours the reaction mixture was filtered, and the mother liquor was concentrated on the rotary evaporator to dryness. The resulting dark-red product 2-[2-(methylamino)acetic acid]-1,4-benzoquinone was used after analysing by HPLC without further purification. 2-[2-(methylamino)acetic acid]-1,4-benzoquinone (0.49 g, 2.5 mmol, 1 eq) was dissolved in methanol (15 ml) and o-phenylenediamine (0.27 g, 2.5 mmol, 1 eq) was added to the reaction mixture. Stirring for 50 hours at room temperature gave a dark-red suspension which was filtered off and concentrated under vacuum. The crude product was diluted in DI water (10 ml) and filtered again. The obtained solid was dried at 60 C to give the final product [(3-hydroxyphenazin-2-yl)(methyl)amino]acetic acid ("[(7-hydroxyphenazin-8-yl)(methyl)amino]acetic acid") (0.25 g, 0.9 mmol) in 36% yield which was analysed by HPLC.

Example 2: [(3-hydroxy-7-sulfophenazin-2-yl)(methyl)amino]acetic acid ("[(7-hydroxy-3-sulfophenazin-8-yl)(methyl)amino]acetic acid")

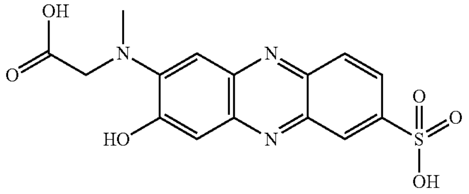 [SMILES: CN(CC(=O)O)c1cc2nc3ccc(S(=O)(=O)O)cc3nc2cc1O]

2-[2-(Methylamino)acetic acid]-1,4-benzoquinone (0.49 g, 2.5 mmol, 1 eq) was dissolved in methanol (15 ml) and 3,4-diaminobenzene-sulfonic acid (65 wt %; 0.72 g, 3.8 mmol, 1.5 eq) was added to the reaction mixture. The purple coloured reaction mixture was stirred for 3 hours at 60° C. before it was concentrated on the rotary evaporator. To the obtained crude product isopropanol (40 ml) was added, suspended and filtered off. The alcohol was evaporated under vacuum to give [(3-hydroxy-7-sulfophenazin-2-yl)(methyl)amino]acetic acid ("[(7-hydroxy-3-sulfophenazin-8-yl)(methyl)amino]acetic acid") which was analysed by HPLC.

Example 3: 2-[(3-hydroxy-1-methoxyphenazin-2-yl)(methyl)amino]ethane-1-sulfonic acid ("2-[(7-hydroxy-9-methoxyphenazin-8-yl)(methyl)amino]ethane-1-sulfonic acid")

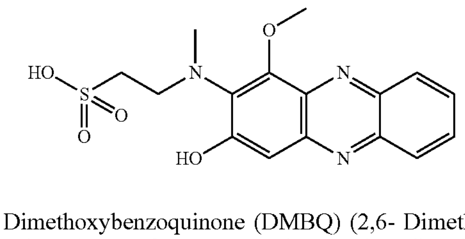

Dimethoxybenzoquinone (DMBQ) (2,6- Dimethoxybenzoquinone) was first converted to 2-[(2,4-dimethoxy-3,6-dioxocyclohexa-1,4-dien-1-yl)(methyl)amino]ethane-1-sulfonic acid by reacting DMBQ (1.85 g, 10 mmol, 1 eq), in methanol (20 ml), with N-methyltaurine sodium salt (62-66% in water) (3.2 g, 4.1 ml, 13 mmol, 1.3 eq). The amine was dissolved in methanol (15 ml) too and added slowly to the DMBQ slurry. After heating for 23 hours at 60° C. the reaction mixture was concentrated on the rotary evaporator to dryness and washed with acetone (2×20 ml). The resulting purple-red product 2-[(2,4-dimethoxy-3,6-dioxocyclohexa-1,4-dien-1-yl)(methyl)amino]ethane-1-sulfonic acid (3.6 g, 9.4 mmol, 94%) was used after analysing by HPLC without further purification. O-Phenylenediamine (0.31 g, 2.86 mmol, 1 eq) was weighed into a 100 ml round bottom flask, dissolved in methanol (15 ml) and 2-[(2,4-dimethoxy-3,6-dioxocyclohexa-1,4-dien-1-yl)(methyl)amino]ethane-1-sulfonic acid (0.83 g, 2.86 mmol, 1 eq) was added. After stirring for 16 hours at room temperature gave a brown suspension which was filtered off. The solid was washed with methanol (2×5 ml) and analysed by HPLC. Upon drying the brown solid the final product 2-[(3-hydroxy-1-methoxyphenazin-2-yl)(methyl)amino]ethane-1-sulfonic acid ("2-[(7-hydroxy-9-methoxyphenazin-8-yl)(methyl)amino]ethane-1-sulfonic acid") (0.10 g, 0.28 mmol) was obtained. Yield: 10%.

Example 4: 3-(benzylamino)phenazin-2-ol ("8-(benzylamino)phenazin-7-ol")

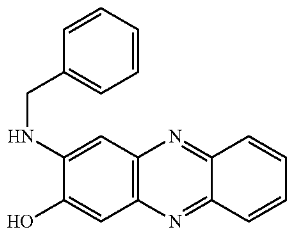 [SMILES: Oc1cc2nc3ccccc3nc2cc1NCc1ccccc1]

O-Phenylenediamine (0.20 g, 2.0 mmol, 1 eq) was weighed into a 100 ml round bottom flask, dissolved in DI water (15 ml) and 2-benzylamino-1,4-benzoquinone (0.43 g, 2.0 mmol, 1 eq) was added. After stirring for 26 hours at 60° C. the reaction mixture was concentrated on rotary evaporator. Suspended in methanol (15 ml) filtered and the filtrate was dried under vacuum to obtain 3-(benzylamino)phenazin-2-ol ("8-(benzylamino)phenazin-7-ol") as product (0.42 g, 1.4 mmol) as a brown solid in 70% yield. Analytic followed by HPLC.

Example 5: 7-(benzylamino)-8-hydroxyphenazine-2-sulfonic acid ("8-(benzylamino)-7-hydroxyphenazine-3-sulfonic acid")

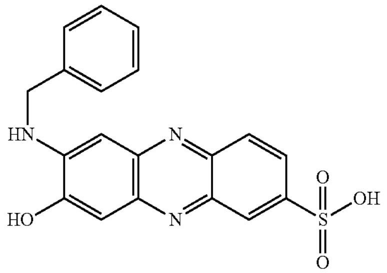 [SMILES: O=S(=O)(O)c1ccc2nc3cc(NCc4ccccc4)c(O)cc3nc2c1]

7-(benzylamino)-8-hydroxyphenazine-2-sulfonic acid ("8-(benzylamino)-7-hydroxyphenazine-3-sulfonic acid") was prepared from 2-benzylamino-1,4-benzoquinone (0.43 g, 2 mmol, 1 eq) and 3,4-diaminobenzenesulfonic acid (65 wt %; 0.78 g, 4.2 mmol, 1 eq) in methanol (15 ml) at 60° C. After 16 hours stirring the reaction mixture was filtered and the filtrate was dried under vacuum to obtain 7-(benzylamino)-8-hydroxyphenazine-2-sulfonic acid ("8-(benzylamino)-7-hydroxyphenazine-3-sulfonic acid") as brown-red product (0.66 g, 1.7 mmol) in 85% yield. Product identity was verified by HPLC.

Example 6: 7-[(2-hydroxyethyl)(methyl)amino]-8-hydroxyphenazine-2-sulfonic acid ("8-[(2-hydroxyethyl)(methyl)amino]-7-hydroxyphenazine-3-sulfonic acid") (IV)

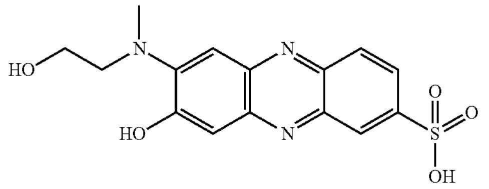 [SMILES: CN(CCO)c1cc2nc3ccc(S(=O)(=O)O)cc3nc2cc1O]

Synthesis of the precursor 2-[(2-hydroxyethyl)(methyl)amino]cyclohexa-2,5-diene-1,4-dione occurred by treating Methoxybenzoquinone (MBQ) (2-methoxy-1,4-benzoquinone) (2.01 g, 14.6 mmol, 1 eq) with the amine 2-Methylaminoethanol (3.27 g, 43.5 mmol, 3 eq), dissolved in ethyl acetate (15 ml), at room temperature. After stirring for 18 h the reaction mixture was filtered off and the obtained solid was characterised by HPLC as 2-[(2-hydroxyethyl)(methyl)amino]cyclohexa-2,5-diene-1,4-dione (2.56 g, 14.6 mmol, 100%). For the preparation of 7-[(2-hydroxyethyl)(methyl)amino]-8-hydroxyphenazine-2-sulfonic acid ("8-[(2-hydroxyethyl)(methyl)amino]-7-hydroxyphenazine-3-sulfonic acid"), the starting materials 2-[(2-hydroxyethyl)(methyl)amino]cyclohexa-2,5-diene-1,4-dione (2.65 g, 14.6 mmol, 1 eq) and 3,4-diaminobenzenesulfonic acid (65 wt %; 3.71 g, 19.7 mmol, 1 eq) were both weighed into a round bottom flask and suspended in DI water (15 ml). Stirring for 3 hours at room temperature gave a purple red suspension which was filtered off. Filtrate was disposed and the solid dried at 60° C. to give 7-[(2-hydroxyethyl)(methyl)amino]phenazine-2-sulfonic acid ("8-[(2-hydroxyethyl)(methyl)amino]-7-hydroxyphenazine-3-sulfonic acid") as product (5.37 g, 16 mmol, >100%) that was analysed by HPLC.

Example 7: 8-hydroxy-7-(methylamino)phenazine-2-sulfonic acid ("7-hydroxy-8-(methylamino)phenazine-3-sulfonic acid")

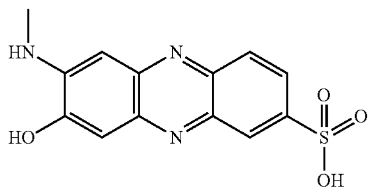 [SMILES: CNc1cc2nc3ccc(S(=O)(=O)O)cc3nc2cc1O]

The precursor 2-methoxy-5-(methylamino)cyclohexa-2,5-diene-1,4-dione (5a) was synthesised by adding Methylamine (33 wt % in ethanol; 1.03 g, 33.0 mmol, 3 eq) to a stirred solution of Methoxybenzoquinone (MBQ) (2-methoxy-1,4-benzoquinone) (0.50 g, 3.6 mmol, 1 eq) in ethyl acetate (10 ml) at 60° C. After 15 min stirring the reaction mixture was filtered off and the solid was washed with ethyl acetate (2×10 ml) to give 2-methoxy-5-(methylamino)cyclohexa-2,5-diene-1,4-dione (0.25 g, 1.5 mmol) as a red solid in 42% yield. For the preparation of 8-hydroxy-7-(methylamino)phenazine-2-sulfonic acid ("7-hydroxy-8-(methylamino)phenazine-3-sulfonic acid"), the starting material 2-methoxy-5-(methylamino)cyclohexa-2,5-diene-1,4-dione (0.25 g, 1.5 mmol, 1 eq) was diluted in methanol (15 ml) and under stirring at room temperature 3,4-diaminobenzenesulfonic acid (65 wt %; 0.38 g, 1.8 mmol, 1 eq) was added. The reaction mixture was heated up to 60° C. and after 48 hours filtered off. The obtained red solid was washed with methanol (2×10 ml) and characterised by HPLC as 8-hydroxy-7-(methylamino)phenazine-2-sulfonic acid ("7-hydroxy-8-(methylamino)phenazine-3-sulfonic acid") (0.14 g, 0.46 mmol, 34%).

Example 8: 7-(dimethylamino)-8-hydroxyphenazine-2-sulfonic acid ("8-(dimethylamino)-7-hydroxyphenazine-3-sulfonic acid") (I)

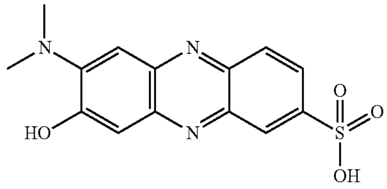 [SMILES: CN(C)c1cc2nc3ccc(S(=O)(=O)O)cc3nc2cc1O]

The starting material 2-(dimethylamino)-5-methoxycyclohexa-2,5-diene-1,4-dione was prepared by adding dimethylamine (7.74 ml, 43.4 mmol, 1 eq) to a stirred solution of Methoxybenzoquinone (MBQ) (2-methoxy-1,4-benzoquinone) (6.0 g, 43.4 mmol, 1 eq) in ethyl acetate (100 ml) at room temperature. After 45 min stirring the reaction mixture was filtered off. The filtrate was concentrated on a rotary evaporator till dryness to obtain the product 2-(dimethylamino)-5-methoxycyclohexa-2,5-diene-1,4-dione (6.0 g, 33.1 mmol) as a purple red solid in 76% yield and analysed by HPLC. For the preparation of 7-(dimethylamino)-8-hydroxyphenazine-2-sulfonic acid ("8-(dimethylamino)-7-hydroxyphenazine-3-sulfonic acid"), both starting materials 2-(dimethylamino)-5-methoxycyclohexa-2,5-diene-1,4-dione (2.0 g, 11.1 mmol, 1 eq) and 3,4-diaminobenzene-sulfonic acid (97 wt %; 2.08 g, 11.05 mmol, 1 eq) were weighed into a 100 ml round bottom flask and suspended in methanol (40 ml). The reaction mixture was heated up to 60° C. for 3 days. Filtration of the suspension and washing the solid with methanol (2×10 ml) the product was air dried. Isolation of the red solid led to 7-(dimethylamino)-8-hydroxyphenazine-2-sulfonic acid ("8-(dimethylamino)-7-hydroxyphenazine-3-sulfonic acid") (2.47 g, 7.72 mmol, 70%).

Example 9: 2-hydroxy-3-[(3-hydroxyphenazin-2-yl)oxy]-N,N,N-trimethylpropane-1-aminium ("2-hydroxy-3-[(7-hydroxyphenazin-8-yl)oxy]-N,N,N-trimethylpropane-1-aminium")

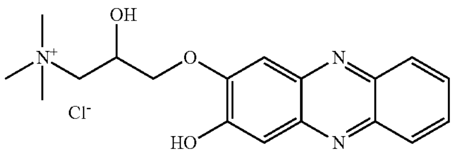 [SMILES: C[N+](C)(C)CC(O)COc1cc2nc3ccccc3nc2cc1O ; [Cl-]]

2,3-Dihydroxyphenazine ("7,8-Dihydroxyphenazine") (51 wt %; 6.24 g, 29.4 mmol, 1 eq) was placed in a 250 ml round bottom flask and suspended in acetone (70 ml). Under vigorously stirring potassium carbonate (4.77 g, 34.5 mmol, 2 eq) was added and stirred for 5 min at 50° C. Afterwards glycidyltrimethylammonium chloride (76 wt % in water; 5.64 g, 37.2 mmol, 2 eq) was added and the vigorously stirring at 50° C. continued for 24 hours. The solvent was decanted, and the residue dissolved in DI water (15 ml) which was acidified with concentrated hydrochloric acid (37 wt %, 3 ml). Cooling the acidic solution in ice bath lead to a brown precipitation that was vacuum filtrated and washed the brown solid once with diluted hydrochloric acid (20 ml) and DI water (20 ml). Drying the solid at 60 C gave 2-hydroxy-3-[(3-hydroxyphenazin-2-yl)oxy]-N,N,N-trimethylpropan-1-aminium ("2-hydroxy-3-[(7-hydroxyphenazin-8-yl)oxy]-N,N,N-trimethylpropan-1-aminium") (4.61 g, 12.8 mmol, 85%) as green-brown powder.

Example 10: Mixture of 3-[(3-hydroxyphenazin-2-yl)oxy]propane-1-sulfonic acid ("3-[(7-hydroxyphenazin-8-yl)oxy]propane-1-sulfonic acid") and 3,3'-[phenazine-2,3-diylbis(oxy)]di(propane-1-sulfonic acid) ("3,3'-[phenazine-7,8-diylbis(oxy)]di(propane-1-sulfonic acid)") (III)

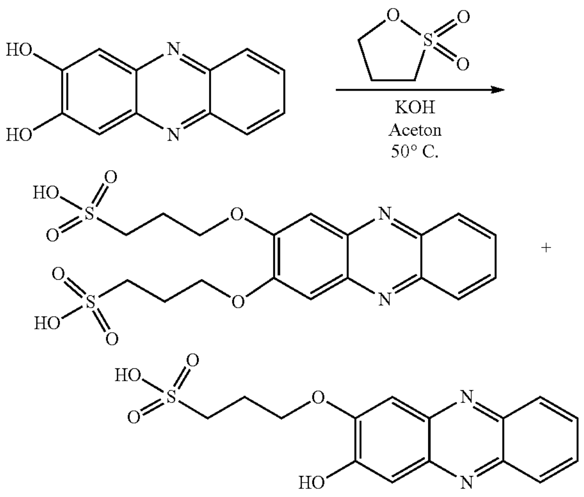

2,3-Dihydroxyphenazine ("7,8-Dihydroxyphenazine") (51 wt %; 5.12 g, 35.9 mmol, 1 eq) was placed in a 250 ml round bottom flask and suspended in acetone (70 ml). Under vigorously stirring potassium hydroxide (85 wt %; 3.58 g, 55.4 mmol, 2 eq) was added and stirred for 5 min at 50° C. before propane-1,3-sulton (4.3 mL, 48.2 mmol, 2 eq) was added. The vigorously stirring at 50° C. continued for 24 hours and was filtered off. The residue was washed with acetone (2×20 ml) and dried on air. Afterwards the crude product was placed in a 250 ml beaker and dissolved in DI water (70 ml) and acidified with concentrated hydrochloric acid (37 wt %, 3 ml). The green suspension was left for 12 hours at room temperature then vacuum filtrated. The acidic filtrate contained 3-[(3-hydroxyphenazin-2-yl)oxy]propane-1-sulfonic acid ("3-[(7-hydroxyphenazine-8-yl)oxy]propane-1-sulfonic acid") and 3,3'-[phenazine-2,3-diylbis(oxy)]di(propane-1-sulfonic acid) ("3,3'-[phenazine-7,8-diylbis(oxy)]di(propane-1-sulfonic acid") as products which were isolated as a green solid after washing the solid with diluted hydrochloric acid (20 ml) and DI water (20 ml). After drying at 60 C the desired molecule mixture (2.9 g, 8.67 mmol) was obtained in 36% yield.

Example 11: 7,8-Dihydroxy-3-methylphenazine-2-sulfonic acid ("7,8-Dihydroxy-2-methylphenazine-3-sulfonic acid")

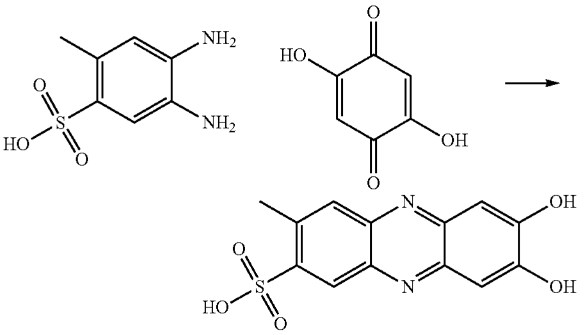

Structural formulae presented below according to the alternative nomenclature as defined by (" . . . "):

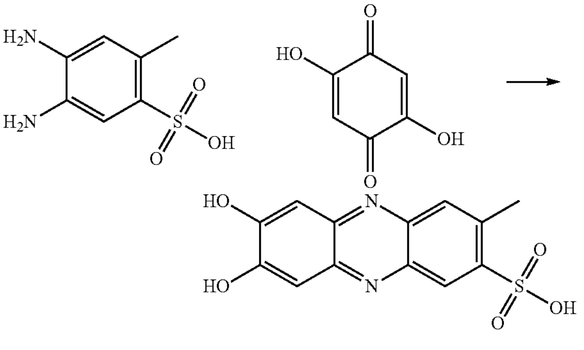

2,5-Dihydroxy-1,4-benzoquinone (3.12 g, 22 mmol, 1 eq) and 4,5-diamino-2-methylbenzene-1-sulfonic acid (4.5 g, 22 mmol, 1 eq) were suspended in 110 mL water in a 250 mL round-bottom flask at room temperature. The mixture was heated under stirring to 70° C. and a complete conversion of the starting material was observed after 19 hours. After three days the brown precipitate was vacuum filtered at room temperature, washed with 20 mL water and dried under reduced pressure. The product was analyzed by HPLC. Final yield: 5.43 g, 79.5%.

Example 12: 7,8-Dihydroxy-4-methylphenazine-2-sulfonic acid ("7,8-Dihydroxy-1-methylphenazine-3-sulfonic acid")

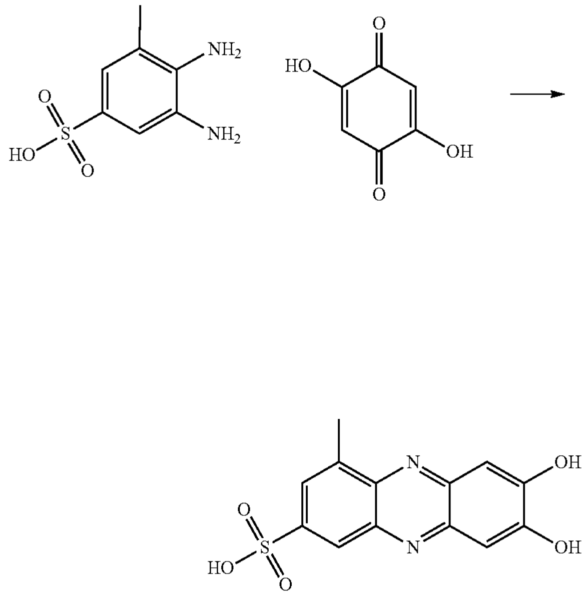

Structural formulae presented below according to the alternative nomenclature as defined by (" . . . "):

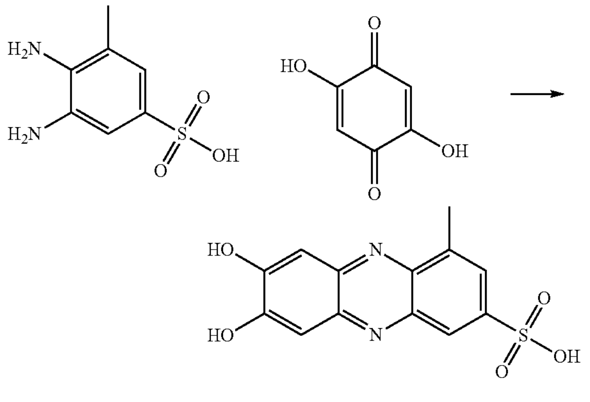

3,4-Diamino-5-methylbenzene-1-sulfonic acid (3.5 g, 17 mmol, 1 eq) was dissolved in 150 mL hot water and filtered prior to its use. The hot filtrate of the sulfonic acid was added to 2,5-dihydroxy-1,4-benzoquinone (2.0 g, 14 mmol, 0.8 eq) and in a 250 mL round-bottom flask and stirred for one hour. The mixture was heated to 60° C. for 26 hours and the brown precipitate vacuum filtrated. The solid was washed with 30 mL acetone and dried under ambient atmosphere. The product was analyzed by HPLC. Final yield: 3.7 g, 86%.

Example 13: Mixture of 7,8-Dihydroxy-3-methylphenazine-2-sulfonic acid ("7,8-Dihydroxy-2-methylphenazine-3-sulfonic acid") and 7,8-Dihydroxy-4-methylphenazine-2-sulfonic acid ("7,8-Dihydroxy-1-methylphenazine-3-sulfonic acid") (II)

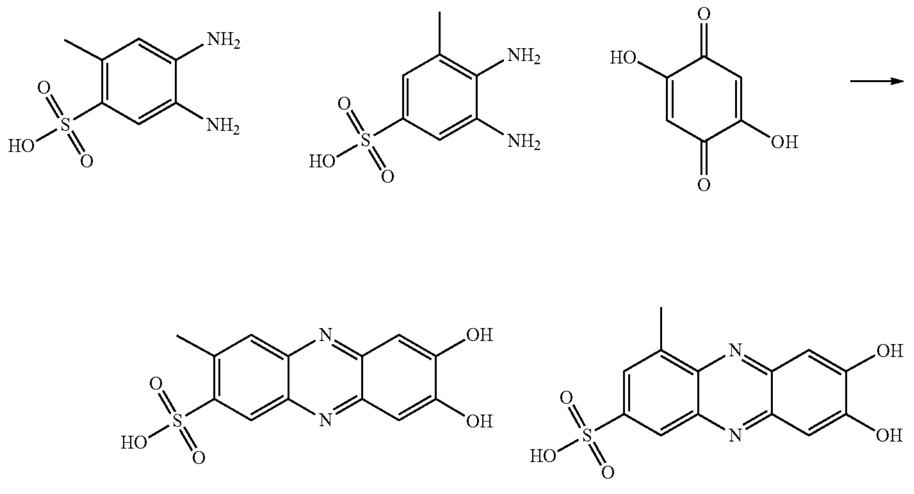 [SMILES: Cc1cc(N)c(N)cc1S(=O)(=O)O ; Cc1cc(S(=O)(=O)O)cc(N)c1N ; O=C1C=C(O)C(=O)C=C1O ; Cc1cc2nc3cc(O)c(O)cc3nc2cc1S(=O)(=O)O ; Cc1cc(S(=O)(=O)O)cc2nc3cc(O)c(O)cc3nc12]

Structural formulae presented below according to the alternative nomenclature as defined by (" . . . "):

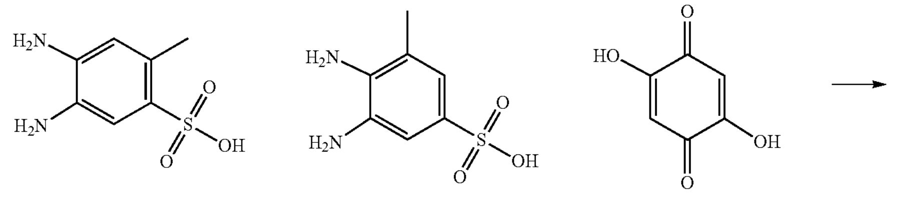

-continued

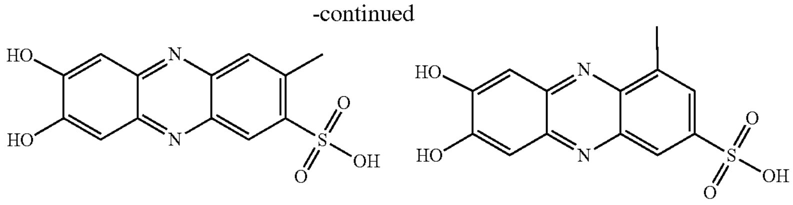

A mixture of and 4,5-diamino-2-methylbenzene-1-sulfonic acid and 3,4-diamino-5-methylbenzene-1-sulfonic acid (18.8 g, 93 mmol, 1 eq) was suspended in 400 mL water and heated to 70° C. Under vigorous stirring 2,5-dihydroxy-1,4-benzoquinone (13.0 g, 93 mmol, 1 eq) was added portionwise. After one hour the reaction mixture was vacuum filtrated and the obtained solid dried under ambient atmosphere. The product was analyzed by HPLC. Final yield: 14.1 g, 49%.

Example 14: 4,4'-(phenazine-2,3-diyldiazanediyl)bis(4-oxobutanoic acid) ("4,4'-(phenazine-7,8-diyldiazanediyl)bis(4-oxobutanoic acid)")

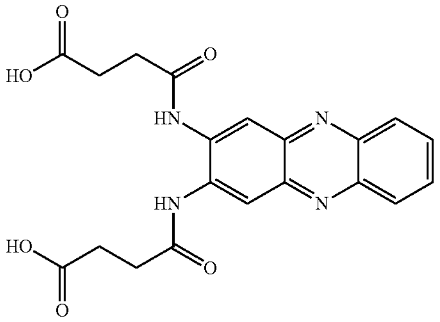 [SMILES: O=C(O)CCC(=O)Nc1cc2nc3ccccc3nc2cc1NC(=O)CCC(=O)O]

2,3-Diaminophenazine ("7,8-Diaminophenazine") (5.00 g, 23.3 mmol) was dissolved in pyridine (30 mL) and succinic anhydride (5.95 g, 58.3 mmol, 2.5 eq) was added in portions. After complete addition, the reaction mixture was stirred for 4 h at 50° C. Then, the solvent was removed under reduced pressure and the residue was extracted using an aqueous solution of KOH (1 M, 300 mL) and EtOAc (3×100 mL). The aqueous layer was acidified with aqueous citric acid solution (10% w/w). The acidic aqueous layer was extracted with EtOAc (3×100 mL). The combined organic layers were dried over $Na_2SO_4$, filtered, and concentrated under reduced pressure. The product was obtained as a red solid (2.90 g, 7.07 mmol, 30%).

II. Synthesis of Compounds of General Formulae (1) to (6)

Example 1: Synthesis of 7,8-Dihydroxyphenazine-2-sulfonic acid ("7,8-Dihydroxyphenazine-3-sulfonic acid") (DHPS)

2,5-Dihydroxy-1,4-benzoquinone (8.1 g, 57.4 mmol) was added to 150 mL boiling water, then 3,4-diaminobenezene-sulfonic acid (10.8 g, 57.4 mmol) was added within a few minutes. The brown suspension was stirred at 95° C. for 18 h, cooled to room temperature and 150 mL acetone were added to the reaction mixture. After filtration the product was obtained as a brown solid (14.1 g, 84%).

Example 2: Synthesis of 7,8-Dihydroxyphenazine-2-carboxylic acid ("7,8-Dihydroxyphenazine-3-carboxylic acid")

2,5-Dihydroxy-1,4-benzoquinone (2.8 g, 20 mmol) was added to 100 mL boiling water, then 3,4-diaminobenzoic acid (3.1 g, 20 mmol) acid was added within a few minutes. The brown suspension was stirred at 95° C. for 18 h, cooled to room temperature and 150 mL acetone was added to the reaction mixture. After filtration the product was obtained in a quantitative yield.

Example 3: Synthesis of 2,3-Dihydroxyphenazine ("7,8-Dihydroxyphenazine")

2,5-Dihydroxy-1,4-benzoquinone (4.0 g, 28.5 mmol) was added to 100 mL boiling water, then 1,2-phenylenediamine (3.1 g, 28.5 mmol) was added within a few minutes. The brown suspension was stirred at 80° C. for 18 h, cooled to room temperature and 130 mL acetone were added to the reaction mixture. After filtration the product was obtained in a quantitative yield.

Example 4: Synthesis of Phenazine and 2,3-Dihydroxyphenazine ("7,8-Dihydroxyphenazine")

1,2-Dihydroxybenzene (0.3 g, 2.8 mmol) and 1,2-phenylenediamine (0.3 g, 2.8 mmol) were heated in a microwave vial to 210° C. for 15 minutes. The melt solidified, was cooled to room temperature and washed several times with water. The insoluble product (0.2 g) contained phenazine and 2,3-dihydroxyphenazine ("7,8-Dihydroxyphenazine") according to HPLC and absorption spectroscopy. Washing the product mixture with 2 M aqueous sodium hydroxide (with an aqueous solution of sodium hydroxide (2 M)) yielded the desired phenazine.

By a specific embodiment, the "substituted phenazine compound" is not one of the compounds presented above resulting from the synthesis according to nay of Examples 1 to 4.

III. Flow Cell Experiments

FT-Cells ("Flow Through"):

For electrochemical characterization, a small laboratory cell was used. A graphite felt (with an area of 6 $cm^2$, 6 mm in thickness, supplier: SGL Sigracell GFA 6EA) in combination with a bipolar plate (4.1 cm×4.1 cm, SGL Sigracell TF6) was employed as both the positive and negative electrode. A cation exchange membrane (630K or 620PE, supplier: fumatech) was used to separate the positive and negative electrolytes. The membrane was conditioned in 0.5 M Base (KOH/NaOH=50 mol %/50 mol %) for at least 150 h prior to each test. An anolyte volume of 12 mL was used for every experiment while the pH of the anolyte solution is adjusted using a 1:1 mixture of KOH/NaOH or solely KOH. The catholyte compositions are listed in table 1 and the catholyte was always employed in at least 1.05 fold stoichiometric excess in order to obtain charge limitation solely due to the phenazine electrolyte (see table 1). The catholyte volume for (IV) is 60 mL (0.4 M KOH; 0.4 M NaOH), for (III) 30 mL (0.2 M KOH and 0.2 M NaOH), and for (I) 20 mL (0.3 M KOH and 0.3 M NaOH). Both electrolytes were pumped by peristaltic pumps (Drifton BT100-1L, Cole Parmer Ismatec MCP and BVP Process IP 65) at a rate of 24 mL/min to the corresponding electrodes, respectively. The electrolyte reservoirs were purged with $N_2$ gas for 1 h before start of charging and the inert atmosphere was maintained during the course of the experiments.

FB-Cells ("Flow By"):

For electrochemical characterization, a small laboratory cell was used. A cell assembly with pressed carbon electrodes (80% graphite-20% PP electrodes with carbon black surface, 41 mm×41 mm×0.72 mm, regularly rhombus shaped surface pattern with maximal height of structures of 1.4 mm) as both the positive and negative electrode was employed. The gap between the base electrode surface and membrane was 1.5 mm on each side of the cell. A cation exchange membrane (620PE, supplier: fumatech) was used to separate the positive and negative electrolytes. The membrane was conditioned in 0.5 M Base (KOH/NaOH=50 mol %/50 mol %) for at least 150 h prior to each test. An anolyte volume of 25 mL was used for every experiment while the pH of the anolyte solution was adjusted using a 1:1 mixture of KOH/NaOH or solely KOH. The catholyte composition is listed in table 1 and the catholyte was always employed in at least 1.05 fold stoichiometric excess in order to obtain charge limitation solely due to the phenazine electrolyte (see table 1). The catholyte volume for (IV) is 60 mL (0.4 M KOH; 0.4 M NaOH), for (III) 30 mL (0.2 M KOH and 0.2 M NaOH), and for (I) 20 mL (0.3 M KOH and 0.3 M NaOH). Alternatively, 25 mL of 0.5 M Phenazine (0.25M NaOH, 0.25M KOH) solution is used on the negative half-cell and 37 mL of a catholyte (0.34 M $K_4Fe(CN)_6$, 0.34 M $Na_4Fe(CN)_6$, 0.125 M NaOH, 0.125 M KOH) is used on the positive half-cell. The electrolytes were circulated by peristaltic pumps (Drifton BT100-1 L, Cole Parmer Ismatec MCP and BVP Process IP 65) at a rate of 72 mL/min, respectively. The electrolyte reservoirs were purged with $N_2$ gas for 1 h before start of charging and the inert atmosphere was maintained during the experiments.

Electrochemical Tests:

Electrochemical testing was performed on a BaSyTec (BaSyTec GmbH, 89176 Asselfingen, Germany) or a Bio-Logic (Bio-Logic Science Instruments, Seyssinet-Pariset 38170, France) battery test system. For galvanostatic cycling, the cell was charged at a current density of or 20 mA/cm$^2$ and discharged at the same current density with the in table 1 listed voltage cut-offs. A full potentiostatic cycle with voltage limitations of 1.7 (up to 1.7 V) or 1.5 V for charging and 1.0 or 0.8 or 0.7 V for discharging with <1.5 mA/cm$^2$ current limitation was conducted in order to get maximum electrolyte exploitation and to calculate the accessible maximum charge per volume of used Phenazine electrolyte. The results are summarized in table 1.

| Phenazine | Charge plateau [V] | Discharge plateau [V] | RTE [%] | OCV [V] at SOC = 100% | Used voltage cut-offs [V] | Catholyte composition | Anolyte composition |
|---|---|---|---|---|---|---|---|
| DHPS | 1.47-1.60 | 1.31-1.15 | 75 | 1.52 | 1.7-1.0 | 0.54M $K_2Na_2Fe(CN)_6$<br>pH = 13.1 | 0.50M Phenazine<br>pH = 13. |
| IV | 1.15-1.25 | 1.05-0.90 | 76 | 1.19 | 1.5-0.7 | 0.2M $K_4Fe(CN)_6$<br>0.2M $Na_4Fe(CN)_6$<br>pH = 13.9 | 0.5M Phenazine<br>2M KOH<br>pH > 14 |
| III | 1.20-1.45 | 1.30-0.90 | 84 | 1.48 | 1.7-0.8 | 0.25M $K_4Fe(CN)_6$<br>0.25M $Na_4Fe(CN)_6$<br>pH = 13.6 | 0.5M Phenazine<br>0.75M NaOH<br>0.75M KOH<br>pH > 14 |
| II | 1.45-1.60 | 1.37-1.15 | 84 | 1.51 | 1.7-1.0 | 0.2M $K_4Fe(CN)_6$<br>0.2M $Na_4Fe(CN)_6$<br>pH = 13.9 | 0.5M Phenazine<br>0.25M NaOH<br>0.25M KOH |
| II | 1.42-1.55 | 1.46-1.28 | 91 | 1.60 | 1.7-1.0 | 1.00M<br>$K_{1.6}Na_{2.4}Fe(CN)_6$<br>pH = 14.0 | 0.87M Phenazine<br>pH = 13.9 |
| I | 1.30-1.41 | 1.26-1.14 | 82 | 1.45 | 1.5-0.7 | 0.3M $K_4Fe(CN)_6$<br>0.3M $Na_4Fe(CN)_6$<br>pH = 13.8 | 0.7M Phenazine<br>1.0M KOH<br>1.0M NaOH<br>pH = 14 |

Table 1: Cell tests of Phenazines Flow-Through Cells. RTE=Round Trip Efficiency, OCV=Open Circuit Voltage, SOC=State-of-charge.

The difference in plateaus [V] (range defined by (i) and (ii) as the lower and upper value: (i) difference of the upper (ultimate) charging value and initial discharging value (and (ii): initial charging value and the ultimate discharging value)) for DHPS is 0.29-0.32, which is advantageously low. Even lower "difference in plateaus" range values are observed for compounds (IV), (III), (II), and (I), respectively, all exhibiting a lower difference in plateaus of the following value ranges: 0.20-0.25 (IV), 0.15-0.30 (III) (which is characterized by a broader range due to its character as a mixture of structurally different compounds), 0.09-0.14 (II), 0.15-0.16 (I). The lower the value for the "difference in plateaus" range, the higher the energetic efficiency of the redox-active compound. The advantageous properties of the tested compounds, in particular of compounds (I), (II), (III) and (IV), is also represented by an RTE value of at least 75%. The RTE value is even higher for compounds (I), (II), (III), and (IV) than for DHPS.

The results of the flow cell experiments by using phenazine compound (II) and phenazine compound (III) are depicted by FIG. 1 (phenazine compound (III)), FIG. 2 and FIG. 3 (phenazine compound (II)). By these figures the initial charge plateau and the subsequent discharge plateau is presented.

The invention claimed is:

1. A redox flow battery, comprising a first half cell comprising an electrolyte solution comprising a composition comprising at least one or at least two substituted phenazine compounds of Formula (I)(a) or Formula (I)(b)

(I)

(a)

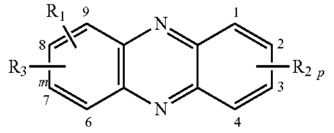

(I)

(b)

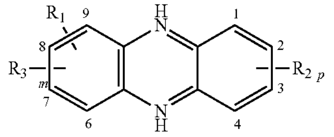

wherein:

$R_1$ is positioned at ring position 7 or 8 and is —$NHR_x$, —$NR_xR_y$, or —N(H)C(═O)$R_x$, wherein Rx and Ry independently represent $C_1$-$C_4$ alkyl optionally substituted with —$CO_2H$, ═O, —$SO_3H$, —OH, substituted or unsubstituted aryl, or —$NH_2$;

$R_2$ is —H, —OH, —$SO_3H$, alkyl, or —$CO_2H$;

$R_3$ is —H, —OH, —$NHR_x$, —$NR_xR_y$, or —N(H)C(═O)$R_x$ m is selected from any number of 0, 1, 2, and 3;

p is selected from any number of 0, 1, 2, 3, and 4;

or a salt thereof; and a solvent, and, optionally, at least one further substituted low molecular weight aromatic redox active compound other than the substituted phenazine compounds of Formula (I)(a) or Formula (I)(b); and a second half-cell comprising an electrolyte solution comprising a redox active species.

2. The redox flow battery of claim 1, wherein:

$R_1$ is —$NR_xR_y$ or —N(H)C(═O)$R_x$, and/or $R_2$ is —OH, —$SO_3H$, alkyl or —$CO_2H$.

3. The redox flow battery claim 1, wherein:

The redox flow battery of $R_1$ is —$NR_xR_y$.

4. The redox flow battery of claim 1, wherein:

$R_x$ and $R_y$ independently represent optionally substituted $C_1$-$C_3$ alkyl.

5. The redox flow battery of claim 1, wherein:

$R_x$ and $R_y$ independently represent optionally substituted methyl or optionally substituted ethyl.

6. The redox flow battery of claim 1, wherein:

$R_2$ is —OH, —$SO_3H$, methyl or —$CO_2H$.

7. The redox flow battery of claim 1, wherein:

m is 0 or 1.

8. The redox flow battery of claim 1, wherein p is 0, 1, 2 or 3.

9. The redox flow battery of claim 1, wherein m is 0 or 1; and p is 1, 2 or 3.

10. The redox flow battery of claim 1, wherein p is 1 or 2; and $R_2$ is positioned at positions 2 and/or 3.

11. The redox flow battery of claim 1, wherein m is 0 or 1; and when m is 1, $R_3$ is positioned at position 7 or position 8.

12. The redox flow battery of claim 1, wherein m is 1;

$R_3$ is positioned at ring position 7 or 8;

p is 2; and $R_2$ is positioned at ring positions 2 and 3.

13. The redox flow battery of claim 1, wherein m is 0;

p is 2; and $R_2$ is positioned at ring positions 2 and 3.

14. The redox flow battery of claim 1, wherein $R_2$ is —$SO_3H$.

15. The redox flow battery of claim 1, wherein m is 1;

$R_3$ is —OH and is positioned at ring position 7 or 8.

16. The redox flow battery of claim 1, wherein $R_1$ is —$NHR_x$ or —$NR_xR_y$;

wherein $R_x$ and $R_y$ independently represent $C_1$-$C_4$ alkyl optionally substituted with —$CO_2H$, ═O, —$SO_3H$, —OH, substituted or unsubstituted phenyl, or —$NH_2$;

p is 1 or 2 and $R_2$ is methyl, —$SO_3H$ or —$CO_2H$;

m is 1; and $R_3$ is positioned at position 7 or position 8, and is —$NHR_x$ or —$NR_xR_y$.

17. The redox flow battery of claim 1, wherein $R_1$ is —$NR_xR_y$ wherein $R_x$ is substituted $C_1$-$C_4$ alkyl; and $R_y$ is unsubstituted $C_1$-$C_4$ alkyl.

18. The redox flow battery of claim 1, wherein $R_1$ is —$NR_xR_y$ wherein $R_x$ is substituted methyl or ethyl; and $R_y$ is methyl.

19. The redox flow battery of claim 1, wherein $R_1$ is —$NR_xR_y$ wherein at least one of $R_x$ and $R_y$ is a substituted $C_1$-$C_4$ alkyl, and wherein the substituent on the $C_1$-$C_4$ alkyl is a terminal substituent.

20. The redox flow battery substituted phenazine compound of claim 19, wherein the $C_1$-$C_4$ alkyl is substituted with —$CO_2H$ or —$SO_3H$.

21. The redox flow battery substituted phenazine compound of claim 1, wherein m is 1;

$R_1$ and $R_3$ are the same and are —$NHR_x$, —$NR_xR_y$, or —N(H)C(═O)$R_x$.

22. The redox flow battery of claim 21, wherein $R_1$ is at position 7 and $R_3$ is at position 8; or $R_1$ is at position 8 and $R_3$ is at position 7.

23. The redox flow battery of claim 1, wherein $R_1$ is —N(H)C(═O)$R_x$, wherein $R_x$ is ethyl substituted on the terminal carbon with —C(═O)OH or —$SO_3H$.

24. The redox flow battery of claim 1, wherein $R_1$ is —N($CH_3$)—$CH_2$—C(═O)OH, —N($CH_3$)-$(CH_2)_2$—C(═O)OH, —N(H)-$(CH_2)_2$—C(═O) OH, —N($CH_3$)—$CH_2$—$SO_3H$, —N($CH_3$)-$(CH_2)_2$—$SO_3H$, —N(H)—$CH_2$—aryl, —N(H)—$CH_2$—$CH_2$—aryl, —N(H)—$CH_2OH$, —N(H)-$(CH_2)_2OH$, —N(H)—$CH_3$, —N(H)—$C_2H_5$, —N(H)C(═O)-$(CH_2)_2$—$CO_2H$, or —N(H)C(═O)-$(CH_2)_2$—$SO_3H$.

25. The redox flow battery substituted phenazine compound of claim 1, wherein $R_2$ is —$SO_3H$, and $R_2$ is positioned at ring position 2 and/or 3.

26. The redox flow battery of claim 1, wherein $R_3$ is —H or —OH.

27. The redox flow battery substituted phenazine compound of claim 26, wherein $R_3$ is selected from —OH and positioned at ring position 7 or 8.

28. The redox flow battery substituted phenazine compound of claim 1, wherein p is 2, and $R_2$ is selected from —$SO_3H$ and methyl.

29. The redox flow battery of claim 1, wherein p is 0, m is 1, and $R_1$ and $R_3$ are identical.

30. The redox flow battery of claim 1, wherein said redox flow battery comprises at least one carbon-based electrode.

31. The redox flow battery of claim 30, wherein the redox flow battery comprises a carbon-based electrode other than carbon felt, carbon cloth and carbon paper.

32. The redox flow battery of claim 1, wherein the redox active species comprised by the second half-cell comprises a salt of $Fe(CN)_6^{3-}$, $Fe(CN)_6^{4-}$or a combination thereof.

33. The redox flow battery of claim 1, wherein the solvent comprises water and/or an organic water-miscible solvent.

34. The redox flow battery of claim 1, wherein the composition has a pH value of from 6 to 13.5.

35. A substituted phenazine compound of Formula (I) (a) or Formula (I) (b)

(I)(a)

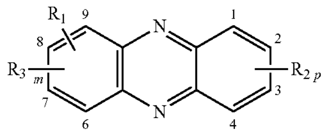

(I)(b)

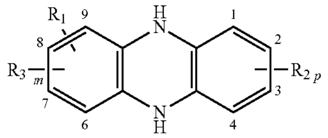

wherein:

$R_1$ is positioned at ring position 7 or 8 and is —$NHR_x$, —$NR_xR_y$, or —N(H)C(=O)$R_x$, wherein $R_x$ and $R_y$ independently represent $C_1$-$C_4$ alkyl optionally substituted with —$CO_2H$, =O, —$SO_3H$, —OH, substituted or unsubstituted aryl, or —$NH_2$;

$R_2$ is —H, —OH, —$SO_3H$, alkyl, or —$CO_2H$;

$R_3$ is —H, —OH, —$NHR_x$, —$NR_xR_y$, or —N(H)C(=O) $R_x$ m is selected from any number of 0, 1, 2, and 3;

p is selected from any number of 0, 1, 2, 3, and 4;

or a salt thereof; and wherein $R_2$ is —$SO_3H$, and $R_2$ is positioned at ring position 2 and/or 3.

36. A substituted phenazine compound of Formula (I) (a) or Formula (I) (b)

(I)(a)

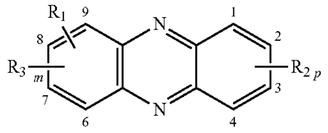

-continued (I)(b)

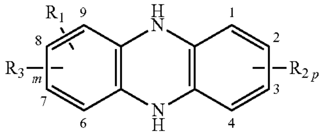

wherein:

$R_1$ is positioned at ring position 7 or 8 and is —$NHR_x$, —$NR_xR_y$, or —N(H)C(=O)$R_x$, wherein $R_x$ and $R_y$ independently represent $C_1$-$C_4$ alkyl optionally substituted with —$CO_2H$, =O, —$SO_3H$, —OH, substituted or unsubstituted aryl, or —$NH_2$;

$R_2$ is —H, —OH, —$SO_3H$, alkyl, or —$CO_2H$;

$R_3$ is —H, —OH, —$NHR_x$, —$NR_xR_y$, or —N(H)C(=O) $R_x$ m is selected from any number of 0, 1, 2, and 3;

p is selected from any number of 0, 1, 2, 3, and 4;

or a salt thereof; and wherein $R_3$ is selected from —OH and positioned at ring position 7 or 8.

37. A substituted phenazine compound of Formula (I) (a) or Formula (I) (b)

(I)(a)

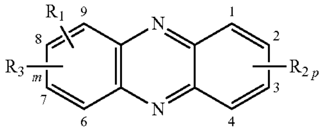

(I)(b)

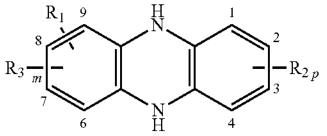

wherein:

$R_1$ is positioned at ring position 7 or 8 and is —$NHR_x$, —$NR_xR_y$, or —N(H)C(=O)$R_x$, wherein $R_x$ and $R_y$ independently represent $C_1$-$C_4$ alkyl optionally substituted with —$CO_2H$, =O, —$SO_3H$, —OH, substituted or unsubstituted aryl, or —$NH_2$;

$R_2$ is —H, —OH, —$SO_3H$, alkyl, or —$CO_2H$;

$R_3$ is —H,—OH, —$NHR_x$, —$NR_xR_y$, or —N(H)C(=O) $R_x$ m is selected from any number of 0, 1, 2, and 3;

p is selected from any number of 0, 1, 2, 3, and 4;

or a salt thereof; and wherein p is 2, and $R_2$ is selected from —$SO_3H$ and methyl.

* * * * *